US011857412B2

(12) United States Patent
Arcaro et al.

(10) Patent No.: US 11,857,412 B2
(45) Date of Patent: ***Jan. 2, 2024

(54) PROSTHETIC VALVE WITH EXPANDABLE FRAME AND ASSOCIATED SYSTEMS AND METHODS

(71) Applicant: EDWARDS LIFESCIENCES CORPORATION, Irvine, CA (US)

(72) Inventors: David J. Arcaro, Flagstaff, AZ (US); Kevin J. Derryberry, Flagstaff, AZ (US); Dustin V. Dienno, Flagstaff, AZ (US); Edwin W. Field, Flagstaff, AZ (US); Bill R. Finney, Flagstaff, AZ (US); Joshua C. Haarer, Flagstaff, AZ (US); Logan R. Hagaman, Flagstaff, AZ (US); Cody L. Hartman, Flagstaff, AZ (US); Russell L. Jacoby, Flagstaff, AZ (US); Roy Manygoats, Jr., Flagstaff, AZ (US); Stephen M. Probert, Flagstaff, AZ (US); Benjamin A. Smith, Flagstaff, AZ (US); Andrew P. Hilton, Flagstaff, AZ (US); Olga Baykova, Flagstaff, AZ (US); Jason T. Alger, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/333,620

(22) Filed: May 28, 2021

(65) Prior Publication Data
US 2021/0393399 A1    Dec. 23, 2021

Related U.S. Application Data

(63) Continuation of application No. 16/129,647, filed on Sep. 12, 2018, now Pat. No. 11,020,221.
(Continued)

(51) Int. Cl.
*A61F 2/24*     (2006.01)
*A61F 2/95*     (2013.01)

(52) U.S. Cl.
CPC .............. *A61F 2/2418* (2013.01); *A61F 2/24* (2013.01); *A61F 2/2433* (2013.01);
(Continued)

(58) Field of Classification Search
CPC ........ A61F 2/24; A61F 2/2418; A61F 2/2433; A61F 2/2463; A61F 2/246; A61F 2/2466;
(Continued)

(56) References Cited

U.S. PATENT DOCUMENTS

| | | | |
|---|---|---|---|
| 654,799 | A | 7/1900 | Levett. |
| 3,739,402 | A | 6/1973 | Kahn et al. |

(Continued)

FOREIGN PATENT DOCUMENTS

| | | |
|---|---|---|
| AU | 2013363172 A1 | 7/2015 |
| AU | 2017202405 A1 | 4/2017 |

(Continued)

OTHER PUBLICATIONS

Cardiac Surgery in the Adult, Third Edition, Chapter 2 2008.
(Continued)

*Primary Examiner* — Dinah Baria
(74) *Attorney, Agent, or Firm* — Edwards Lifesciences

(57) ABSTRACT

Aspects of the disclosure relate to prosthetic valves having a frame, a frame cover, and a leaflet construct. Some aspects are directed to a diametric taper for the prosthetic valve for achieving enhanced performance of the prosthetic valve under operational conditions, enhanced compressibility and delivery characteristics, and other additional or alternative advantages. Other aspects are directed toward unique assembly and attachment methods for securing leaflet constructs to support structures. Other aspects are directed toward fea-
(Continued)

tures for interacting with transcatheter delivery systems. Still other aspects are directed to such apparatuses, systems, and methods for valve replacement, such as cardiac valve replacement.

18 Claims, 26 Drawing Sheets

Related U.S. Application Data

(60) Provisional application No. 62/682,685, filed on Jun. 8, 2018, provisional application No. 62/579,759, filed on Oct. 31, 2017.

(52) U.S. Cl.
CPC .......... *A61F 2/2439* (2013.01); *A61F 2/2463* (2013.01); *A61F 2/246* (2013.01); *A61F 2/2436* (2013.01); *A61F 2/2466* (2013.01); *A61F 2002/9511* (2013.01); *A61F 2210/0014* (2013.01); *A61F 2210/0076* (2013.01); *A61F 2220/005* (2013.01); *A61F 2220/0016* (2013.01); *A61F 2220/0025* (2013.01); *A61F 2220/0033* (2013.01); *A61F 2220/0058* (2013.01); *A61F 2220/0075* (2013.01); *A61F 2230/0054* (2013.01); *A61F 2230/0067* (2013.01); *A61F 2230/0069* (2013.01); *A61F 2250/0039* (2013.01); *A61F 2250/0069* (2013.01)

(58) Field of Classification Search
CPC ............ A61F 2/2436; A61F 2250/0069; A61F 2220/0075; A61F 2220/005; A61F 2220/0016; A61F 2230/0069; A61F 2210/0014
See application file for complete search history.

(56) References Cited

U.S. PATENT DOCUMENTS

| | | | |
|---|---|---|---|
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B2 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |

(56) References Cited

U.S. PATENT DOCUMENTS

| | | |
|---|---|---|
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Apeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |

(56) References Cited

U.S. PATENT DOCUMENTS

| | | |
|---|---|---|
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |

(56) References Cited

U.S. PATENT DOCUMENTS

| | | |
|---|---|---|
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Lim et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |

(56) References Cited

FOREIGN PATENT DOCUMENTS

| | | |
|---|---|---|
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| NO | 2008/150529 A1 | 12/2008 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A2 | 2/2006 |
| WO | 2006/058322 A2 | 6/2006 |
| WO | 2006/108090 A1 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |

(56) References Cited

FOREIGN PATENT DOCUMENTS

| | | |
|---|---|---|
| WO | 2008/021006 A3 | 8/2008 |
| WO | 2008/097589 A1 | 8/2008 |
| WO | 2008/097592 A2 | 8/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2014/149319 A1 | 9/2014 |
| WO | 2014/181188 A2 | 11/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |
| WO | 2019/246268 A1 | 12/2019 |

OTHER PUBLICATIONS

International Search Report and Written Opinion issued in PCT/US2018/050764, dated Nov. 23, 2018, 13 pages.
International Search Report and Written Opinion issued in PCT/US2018/050766, dated Mar. 11, 2019, 16 pages.
International Search Report and Written Opinion issued in PCT/US2018/050778, dated Nov. 29, 2018, 11 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of GORE (Trademark) ePTFE Fibers (2007).
Opposition from EP17187595.8, filed Sep. 12, 2019, 50 pages.
Google Image Search Results, "S-Shaped", accessed Nov. 1, 2013.
International Preliminary Report on Patentability received for PCT Patent Application No. PCT/US15/50113, dated Mar. 30, 2017, 9 pages.
International Preliminary Report on Patentability received for PCT Patent Application No. PCT/US2020/027921, dated Oct. 21, 2021, 11 pages.
International Search Report and Written Opinion received for PCT Patent Application No. PCT/US2020/027921, dated Jul. 24, 2020, 16 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Forward citations for E12 obtained from: https://scholar.google.com/scholar?cites=5981833429320176658&assdt=2005&sciodt=0,5&hl=en.
International Preliminary Report on Patentability received for PCT Patent Application No. PCT/US2020/044603, dated Feb. 10, 2022, 9 pages.
International Search Report and Written Opinion received for PCT Patent Application No. PCT/US2020/044603, dated Oct. 20, 2020, 12 pages.
English translation of RU2434604 (C1), filed Apr. 30, 2010, translation powered by EPO and Google, 8 pages.
Opposition from EP16196687.4, mailed on Dec. 12, 2019, 38 pages.

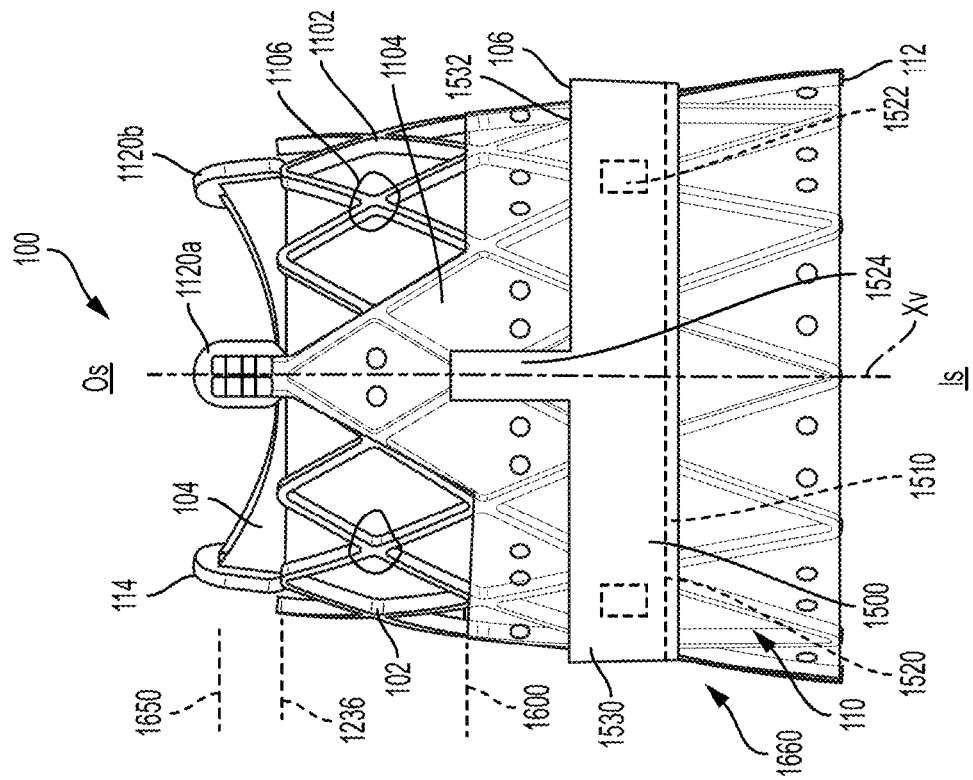
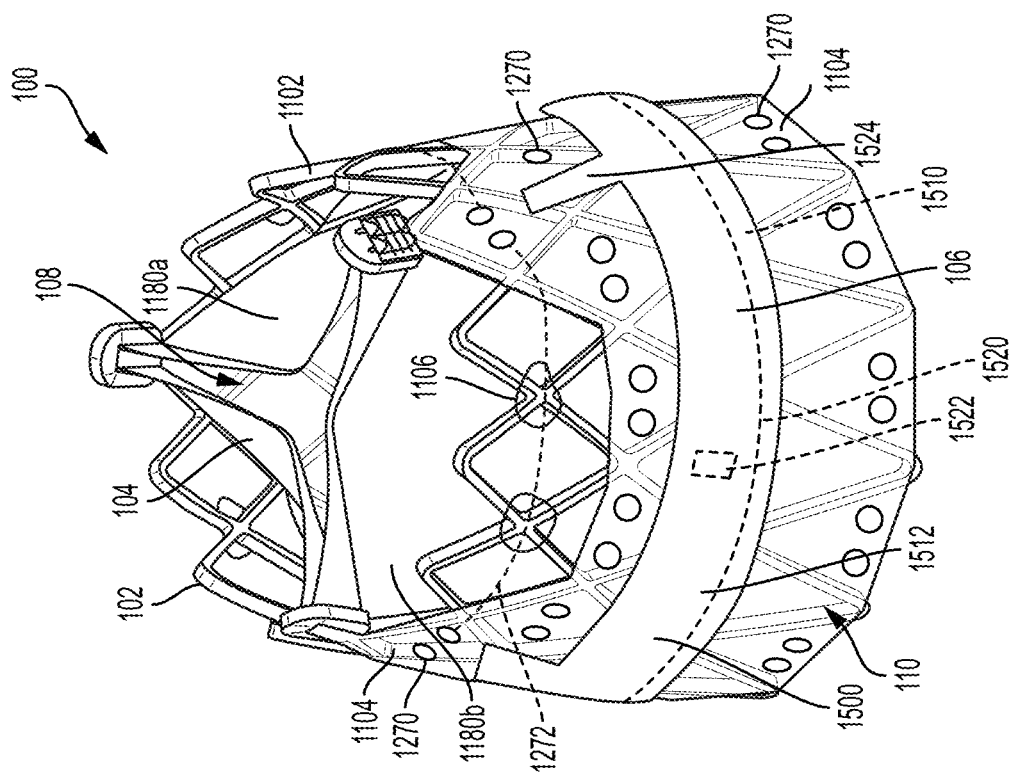

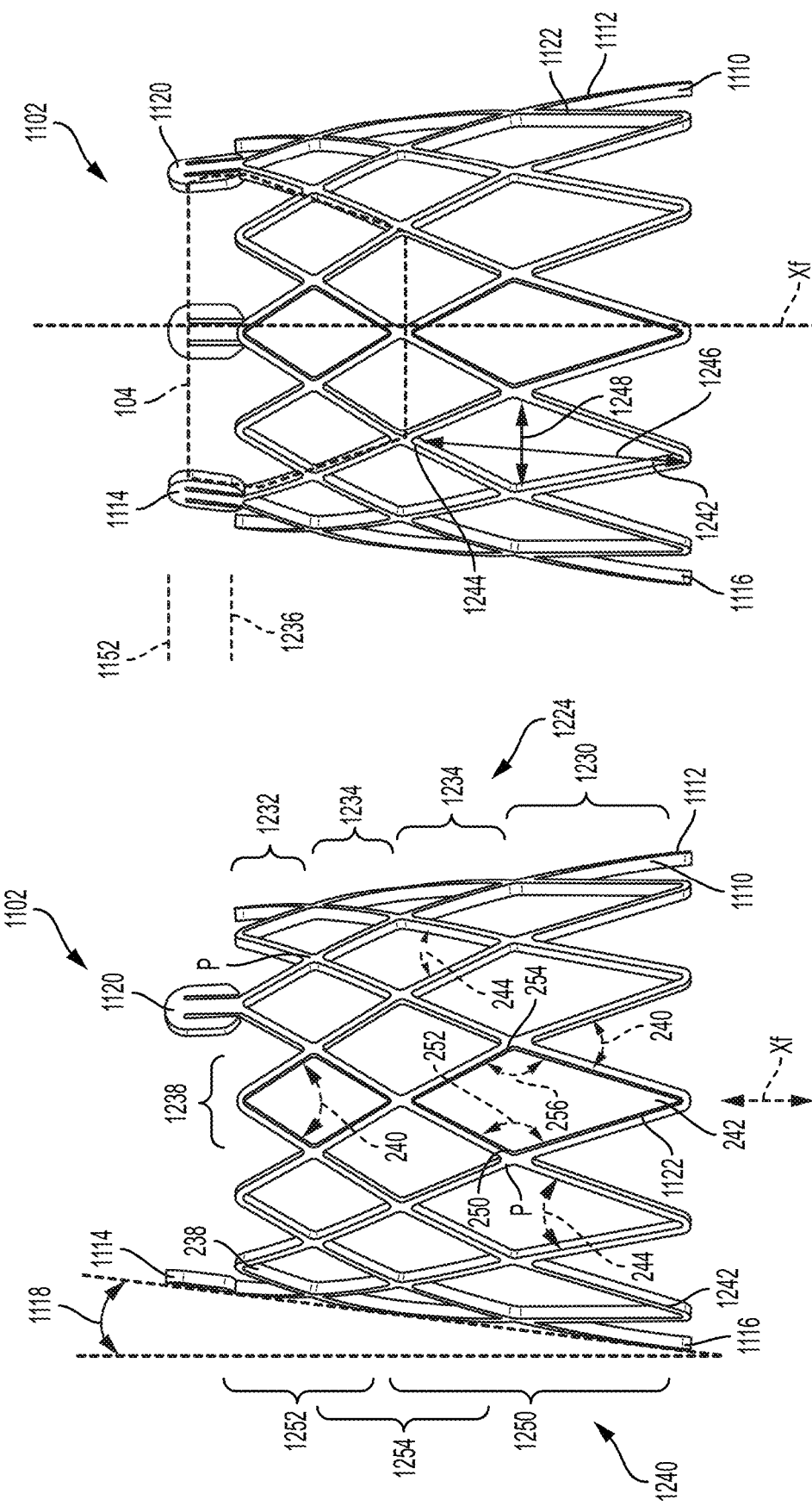

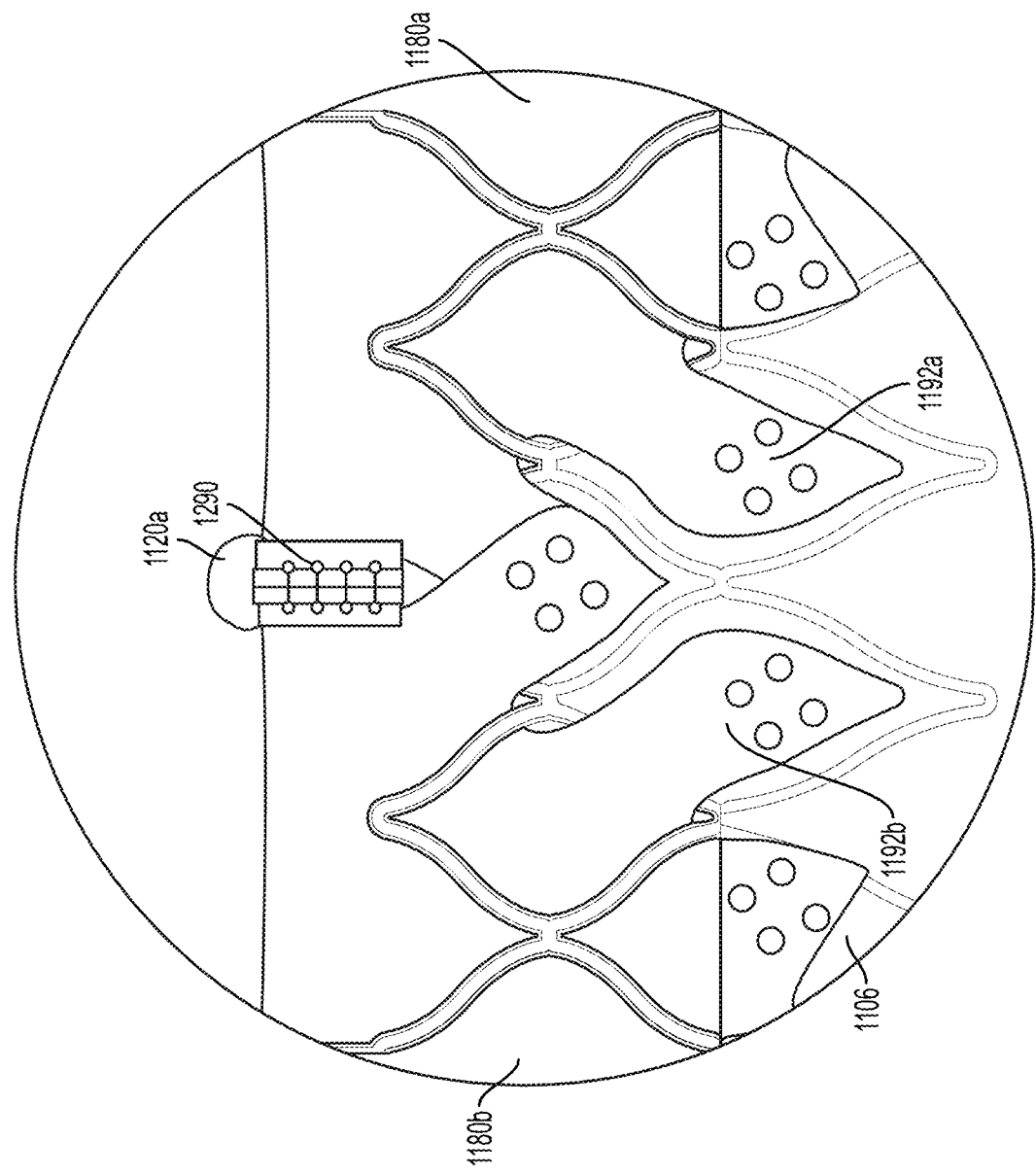

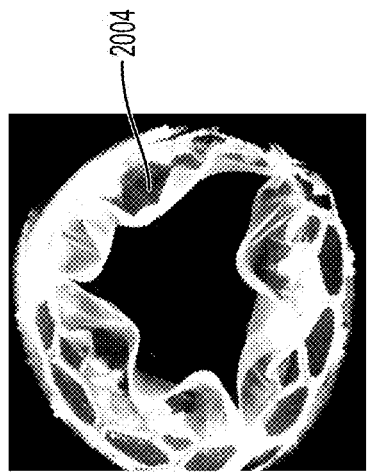
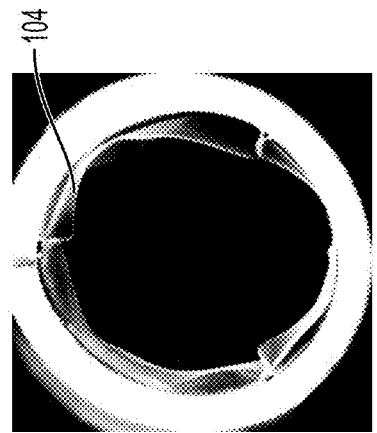
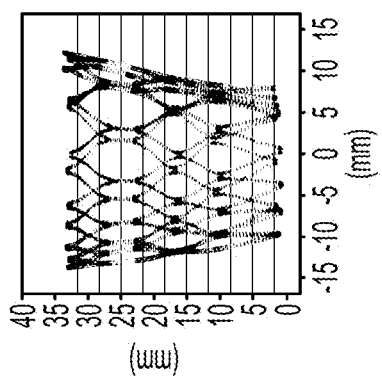
FIG. 15
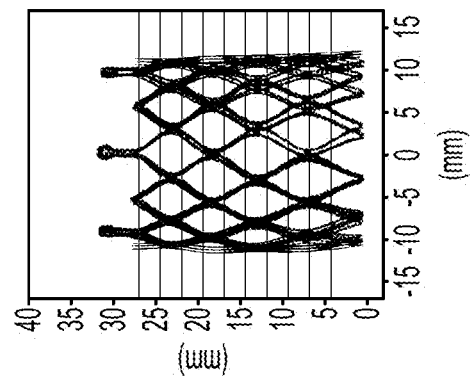
FIG. 16
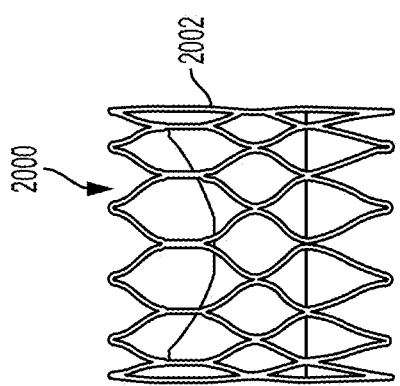
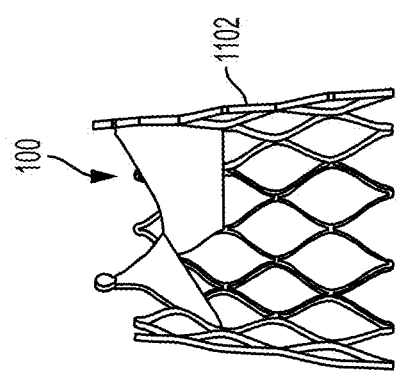

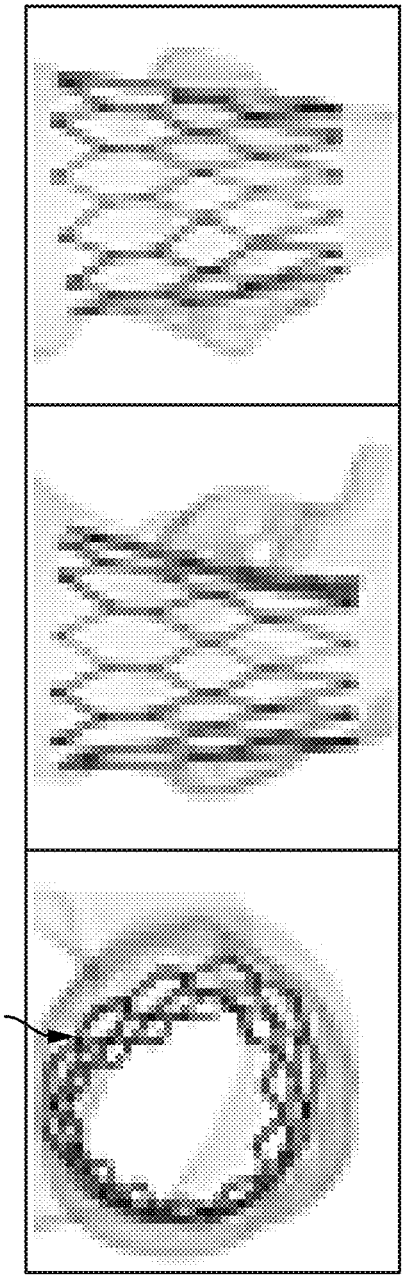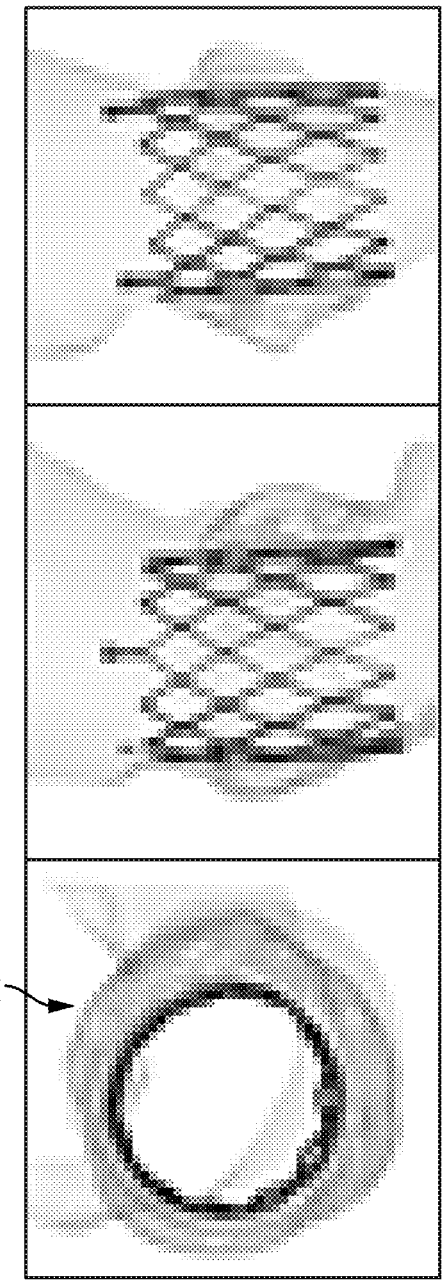

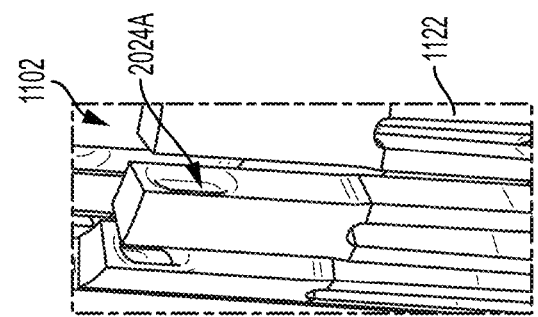
FIG. 20
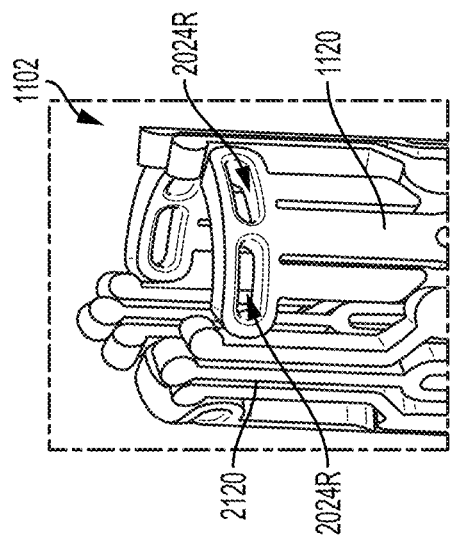
FIG. 23
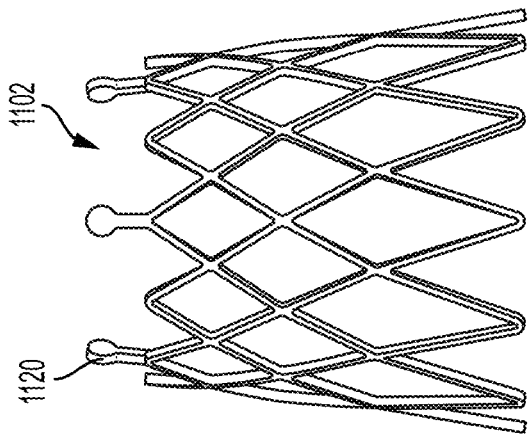
FIG. 19
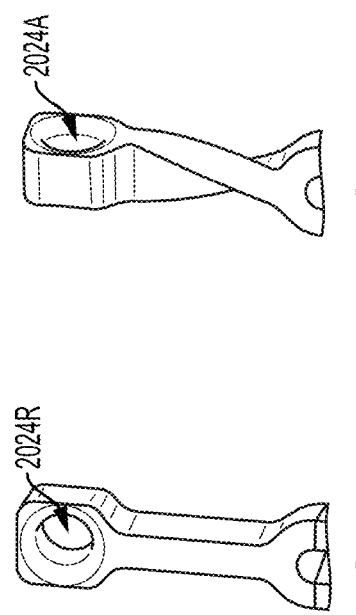
FIG. 22
FIG. 21

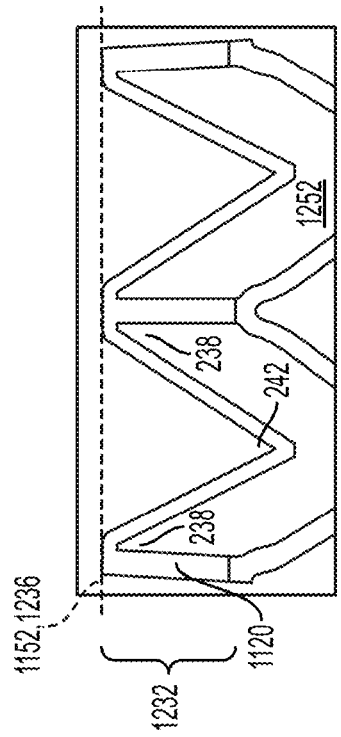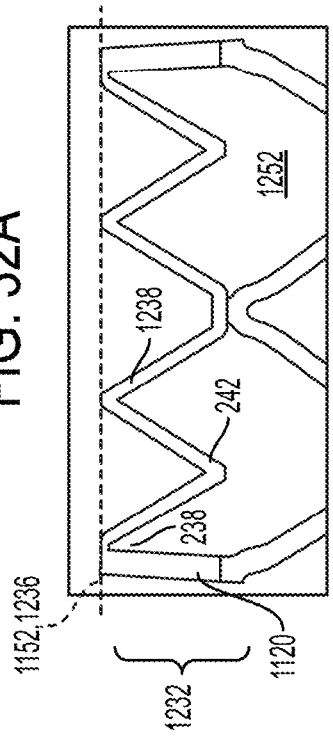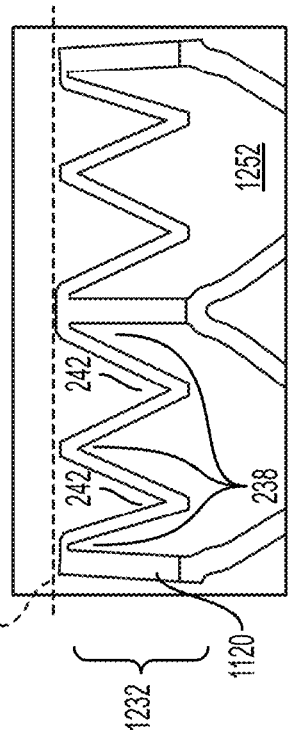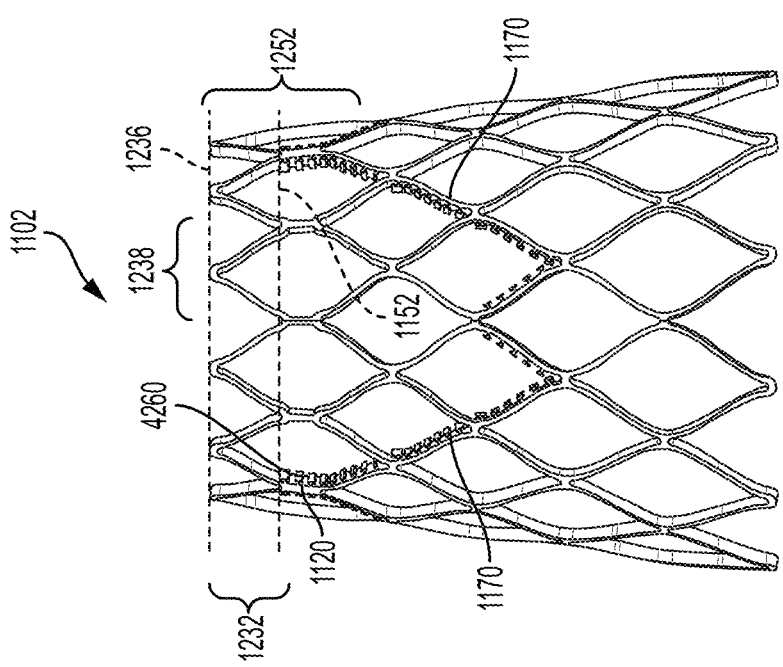

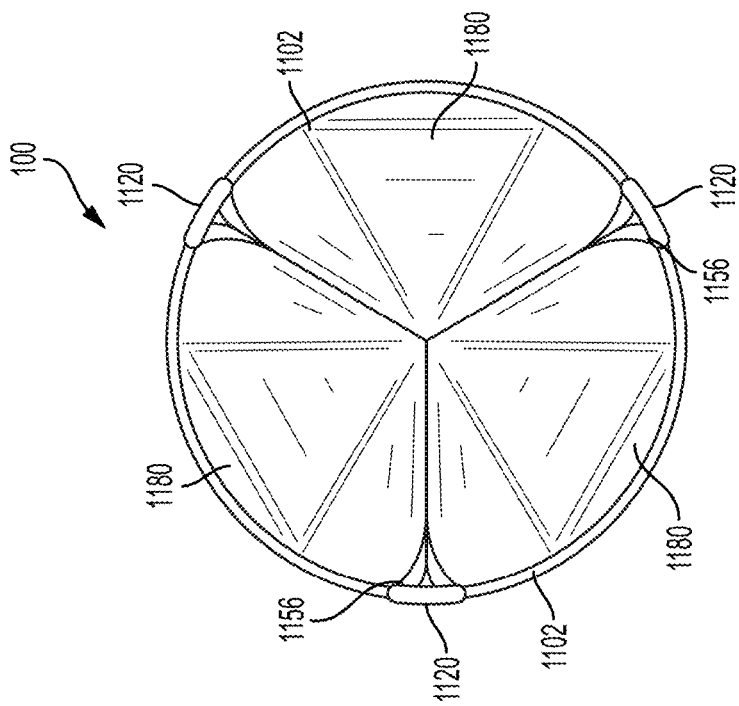
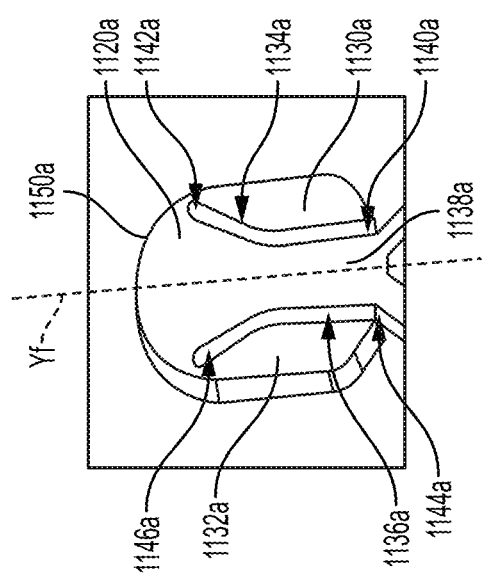
FIG. 42
FIG. 41

PROSTHETIC VALVE WITH EXPANDABLE FRAME AND ASSOCIATED SYSTEMS AND METHODS

CROSS-REFERENCE TO RELATED APPLICATION

This application is a continuation of U.S. application Ser. No. 16/129,647, filed Sep. 12, 2018, now U.S. Pat. No. 11,020,221, issued Jun. 1, 2021, which claims the benefit of U.S. Provisional Application No. 62/564,031, filed Sep. 27, 2017, U.S. Provisional Application No. 62/579,759, filed Oct. 31, 2017, and U.S. Provisional Application No. 62/682,685, filed Jun. 8, 2018, all of which are incorporated herein by reference in their entireties for all purposes.

FIELD

The present disclosure relates to prosthetic valves, including prosthetic heart valves, and transcatheter delivery systems and associated methods.

BACKGROUND

Prosthetic valves that are collapsible into a compact delivery configuration and expandable (e.g., self-expanding or expandable via application of an expansion force) are beneficial for various reasons, including the ability to deliver such devices with minimally invasive techniques. Such prosthetic valves typically include some type of support structure (e.g., an expandable frame) and a leaflet construct including one or more leaflets.

The term "leaflet" as used in the context of prosthetic valves is generally a flexible component operable to move between an open and closed position under the influence of pressure differentials. In an open position, the leaflet allows flow through the prosthetic valve. In a closed position, the leaflet at least partially blocks retrograde flow, and often fully blocks retrograde flow. In valves comprising multiple leaflets, each leaflet cooperates with at least one neighboring leaflet in blocking retrograde flow.

The pressure differential in the actuating the leaflets can be caused by a blood pressure differential, such as that exhibited following the contraction of a ventricle or atrium of the heart, for example. In such examples, the pressure differential typically results from a fluid pressure of blood building up on one side of the leaflets when closed. As the pressure on an inflow side of the prosthetic valve rises above the pressure on the outflow side of the prosthetic valve, the leaflets open and blood flows therethrough. As blood flows through the prosthetic valve into a neighboring chamber or blood vessel, the pressure on the inflow side equalizes with the pressure on the outflow side. As the pressure on the outflow side of the prosthetic valve raises above the blood pressure on the inflow side of the prosthetic valve, the leaflet returns to the closed position to partially or fully block retrograde flow of blood through the prosthetic valve.

Improvements in the reliability of collapsible and expandable prosthetic valve designs, including collapsibility, ease of expansion, and reliability in performance remain to be realized.

SUMMARY

Various embodiments are directed toward prosthetic valves having a frame, a frame cover, and a leaflet construct. Some aspects are directed to a diametric taper for the prosthetic valve for achieving enhanced performance of the prosthetic valve under operational conditions, enhanced compressibility and delivery characteristics, and other additional or alternative advantages. Other aspects are directed toward unique assembly and attachment methods for securing leaflet constructs to support structures. Other aspects are directed toward features for interacting with transcatheter delivery systems. Still other aspects are directed to apparatuses, systems, and methods for valve replacement, such as cardiac valve replacement, although a variety of applications are contemplated.

According to one example, ("Example 1"), a prosthetic valve configured to be diametrically collapsible into a compact delivery configuration, comprises a support structure and a leaflet construct. The support structure has an outer side and an inner side and a central longitudinal axis and includes a frame including a plurality of frame members and a plurality of commissure posts. The frame extends from a distal end to a proximal end, the distal end having a first diameter and the proximal end having a second larger diameter such that the frame has a diametric taper including a decreasing diameter in a distal direction between the distal end and the proximal end. The diametric taper defines a taper angle relative to the central longitudinal axis of the frame when the prosthetic valve is in an unloaded state. And, the leaflet construct includes a plurality of leaflets spaced circumferentially about the leaflet construct, the plurality of leaflets being operatively coupled to the frame.

According to another example ("Example 2"), further to Example 1, the taper angle is constant from the distal end to the proximal end.

According to another example ("Example 3"), further to Example 1, the taper angle varies from the distal end to the proximal end.

According to another example ("Example 4") further to any one of preceding Examples 1 to 3, the diametric taper includes a proximal taper, a distal taper, and an intermediate taper between the distal taper and the proximal taper, and further wherein the distal taper has a greater taper angle than a taper angle of the intermediate portion.

According to another example, ("Example 5"), further to any one of preceding Examples 1, 3, or 4, the diametric taper includes a proximal taper, a distal taper, and an intermediate taper between the distal taper and the proximal taper, and further wherein the intermediate taper has a greater taper angle than a taper angle of the proximal taper.

According to another example, ("Example 6"), further to any one of preceding Examples 1 or 3 to 5, the diametric taper includes a proximal taper, a distal taper, and an intermediate taper between the distal taper and the proximal taper, and further wherein a taper angle of the distal taper is greater than a taper angle of the proximal taper.

According to another example, ("Example 7"), further to any one of preceding Examples 4 to 6, the plurality of commissure posts defines the distal taper of the diametric taper.

According to another example, ("Example 8"), further to any one of preceding Examples 1 to 7, the plurality of frame members extend distally to a frame member distal boundary and the plurality of commissure posts extend distally to a commissure post distal boundary, and further wherein the commissure post distal boundary is located distal to the frame member distal boundary.

According to another example, ("Example 9"), further to any one of preceding Examples 1 to 8, the plurality of frame members extend distally to a frame member distal boundary and the plurality of leaflets extend distal to the frame member distal boundary.

According to another example, ("Example 10"), further to any one of preceding Examples 1 to 9, the plurality of frame members define a plurality of rows of closed cells, including a distal row of closed cells and a proximal row of closed cells located proximal to the distal row of closed cells, wherein each of the closed cells of the distal row of closed cells defines a cell height between a distal end and a proximal end of the closed cell, wherein each of the closed cells of the proximal row of closed cells defines a cell height between a distal end and a proximal end of the closed cell, and further wherein the cell heights of the distal row of closed cells are each less than the cell heights of the proximal row of closed cells.

According to another example, ("Example 11"), further to preceding Example 10, the plurality of rows of closed cells defined by the plurality of frame members further includes an intermediate row of closed cells located intermediate the proximal row of closed cells and the distal row of closed cells, wherein each of the closed cells of the intermediate row of closed cells defines a cell height between a distal end and a proximal end of the closed cell, and further wherein the cell heights of the intermediate row of closed cells are less than the cell heights of the proximal row of closed cells and greater than the cell heights of the distal row of closed cells.

According to another example, ("Example 12"), further to any one of preceding Examples 1 to 11, the plurality of frame members define a plurality of rows of distal-facing apices, wherein each of the distal-facing apices defines an apex angle, and wherein each of the apex angles of each of the distal-facing apices of each of the rows of distal-facing apices has an apex angle that is within 10% of a common apex angle.

According to another example, ("Example 13"), further to any one of preceding Examples 1 to 12, the plurality of frame members define a plurality of rows of proximal-facing apices, wherein each of the proximal-facing apices defines an apex angle, and wherein each of the apex angles of each of the proximal-facing apices of each of the rows of proximal-facing apices has an apex angle that is within 10% of a common apex angle.

According to another example, ("Example 14"), further to any one of preceding Examples 1 to 13, the plurality of frame members defines a column of distal-facing apices and proximal-facing apices, each of the distal-facing apices and the proximal-facing apices defining apex angles within 10% of a common apex angle.

According to another example, ("Example 15"), further to any one of preceding Examples 1 to 14, each of the leaflets of the leaflet construct extends distally from a leaflet base to a free edge, each of the leaflet bases being located at a first longitudinal location along the central longitudinal axis of the support structure, the frame defining a leaflet base level diameter at the first longitudinal location, each of the leaflets being coupled to the plurality of commissure posts second longitudinal location along the central longitudinal axis of the support structure that is distal to the first longitudinal location, the frame defining a commissure level diameter at the second longitudinal location, the commissure level diameter being less than the leaflet base level diameter when the prosthetic valve is in an unloaded state and the commissure level diameter being closer in value to the leaflet base diameter when the prosthetic valve is in an operational state than in the unloaded state, the operational state including the prosthetic valve being subjected to an inward radial compressive force on at least a proximal portion of the prosthetic valve.

According to another example, ("Example 16"), further to any one of preceding Examples 1 to 15, the support structure further comprises a cover secured to the frame.

According to another example, ("Example 17"), further to any one of preceding Examples 1 to 16, the prosthetic valve further comprises a sealing cuff including a sealing member having a portion that is secured circumferentially about the support structure and a distal-facing edge, at least a portion of which is not secure to the support structure.

According to another example, ("Example 18"), further to preceding Example 17, the distal-facing edge is secured to the support structure at a plurality of locations and remains unsecured from the support structure at a plurality of locations.

According to another example, ("Example 19"), further to any one of preceding Examples 1 to 18, each of the leaflets of the leaflet construct extends distally from a leaflet base to a free edge, each of the leaflet bases being substantially flat.

According to another example, ("Example 20"), further to any one of preceding Examples 1 to 19, the prosthetic valve further comprises a plurality of constraint retainers secured to the plurality of frame members.

According to another example, ("Example 21"), further to preceding Example 20, the prosthetic valve further comprises a constraint slidably received by the plurality of constraint retainers.

According to another example, ("Example 22"), further to any one of preceding Examples 20 or 21, the plurality of constraint retainers are each formed by one or more loops of material.

According to another example, ("Example 23"), further to any one of preceding Examples 1 to 22, one or more of the plurality of frame members of the frame define at least one of a circumferentially-oriented eyelet and a radially-oriented eyelet configured to slidably receive a constraint of a delivery catheter.

According to another example, ("Example 24"), further to any one of preceding Examples 1 to 23, one or more of the plurality of commissure posts of the frame define at least one of a circumferentially-oriented eyelet and a radially-oriented eyelet configured to slidably receive a constraint of a delivery catheter.

According to another example, ("Example 25"), further to any one of preceding Examples 1 to 23, the leaflet construct includes a fold over portion including a plurality of attachment tabs passed through a portion of the support structure and secured to an outer side of the support structure.

According to another example, ("Example 26"), further to any one of preceding Examples 1 to 25, the prosthetic valve further comprises a leaflet retention feature including a plurality of struts and defining a plurality of cells between the struts, wherein the support structure includes a plurality of leaflet frame projections and the plurality of struts of the leaflet retention feature form an interference fit with the plurality of leaflet frame projections received in the plurality of cells between the struts, and further wherein the leaflet construct is secured to the support structure by the leaflet retention feature.

According to another example, ("Example 27"), further to any one of preceding Examples 1 to 26, the plurality of frame members define a distal-facing apex that defines an offset intersection location with a proximal-facing apex proximate one of the plurality of commissure posts, the offset intersection location including two diagonal frame members that define a relatively straight line extending through the offset intersection.

According to another example, ("Example 28"), a method of implanting a prosthetic valve in a body of a patient according to any one of preceding Examples 1 to 27, or according to any one of Examples 31 to 36 that follow, includes positioning a prosthetic valve at a desired treatment location within the body and securing the prosthetic valve at the desired treatment location.

According to another example, ("Example 29"), further to preceding Example 28, the desired treatment location is a native valve orifice and the method includes positioning the prosthetic valve at the native valve orifice and securing the prosthetic valve at the native valve orifice.

According to another example, ("Example 30"), further to preceding Example 29, the method further includes positioning the prosthetic valve at the desired treatment location within the body with the prosthetic valve in a diametrically compacted delivery profile and expanding the prosthetic valve in the native valve orifice such that an inward radial compressive load is applied to the prosthetic valve and the diametric taper exhibited by the prosthetic valve is reduced relative to when the prosthetic valve is in an unloaded state.

According to another example, ("Example 31"), a prosthetic valve includes a frame defining a circumference and a central longitudinal axis, a cover coupled to the frame, the cover including a constraint guide defining a tunnel extending transversely to the central longitudinal axis of the frame, the tunnel extending between a first opening and a second opening in an outer surface of the cover, and a constraint slidably received in the tunnel, the constraint passing into the tunnel through the first opening and out of the tunnel through the second opening, the constraint extending around the frame to retain the frame in a diametrically compacted, delivery configuration.

According to another example, ("Example 32"), further to preceding Example 31, the cover includes a plurality of separate constraint guides each spaced circumferentially apart from one another about the circumference of the frame, the constraint passing through each of the plurality of constraint guides.

According to another example, ("Example 33"), further to preceding Example 32, each of the plurality of separate constraint guides is circumferentially-aligned about the circumference of the frame.

According to another example, ("Example 34"), further to any one of Examples 31 to 33, the constraint guide includes an outer layer of cover material.

According to another example, ("Example 35"), further to any one of Examples 31 to 34, the cover includes a base layer and an outer layer and the constraint guide is formed by the base layer and the outer layer, the tunnel of the constraint guide being defined between the base layer and the outer layer of the cover.

According to another example, ("Example 36"), further to any one of Examples 31 to 35, the tunnel of the constraint guide extends within a thickness of the cover.

According to another example, ("Example 37"), further to any one of Examples 1 to 27 or 31 to 36, the frame includes a plurality of radially actuatable anchor members configured to anchor the prosthetic valve at a desired location in a body of a patient.

According to another example, ("Example 38"), a method of implanting a prosthetic valve according to any one of Examples 1 to 27 or Examples 31 to 36 in a body of a patient to treat valve insufficiency includes positioning the prosthetic valve at a desired treatment location within the body and securing the prosthetic valve at the desired treatment location, including expanding the prosthetic valve at the desired treatment location such that a plurality of radially actuatable anchor members of the prosthetic valve anchor the prosthetic valve at the desired treatment location in the body of the patient.

According to another example ("Example 39"), further to Example 38 the desired treatment location is a native aortic valve exhibiting aortic regurgitation and the method includes positioning the prosthetic valve at the native valve orifice and securing the prosthetic valve at the native valve orifice by engaging the radially actuable anchor members with tissue associated with the native aortic valve.

According to another example ("Example 40"), further to Examples 38 or 39 positioning the prosthetic valve at the desired treatment location within the body includes constraining the prosthetic valve in a diametrically compacted delivery profile with one or more constraints and positioning the prosthetic valve at the desired treatment location within the body with the prosthetic valve in the diametrically compacted delivery profile. Additionally, securing the prosthetic valve at the desired treatment location further includes, radially actuating the radially actuable anchor members by releasing the one or more constraints and expanding the prosthetic valve in the native valve orifice by releasing the one or more constraints such that the radially actuable anchor members engage the tissue associated with the native aortic valve. In some instances, an inward radial compressive load is applied to the prosthetic valve and a diametric taper exhibited by the prosthetic valve is reduced relative to when the prosthetic valve is in an unloaded state.

According to another example ("Example 41"), a method of treating at least one of valve insufficiency or valve stenosis includes delivering a prosthetic valve to a native valve in a body of a patient that is exhibiting at least one of valve insufficiency and valve stenosis, the prosthetic valve including a support portion, an anchor member extending from the support portion that is biased to extend radially outward from the support portion, and a leaflet construct operatively coupled to the support portion. The method also includes engaging the anchor member with tissue associated with the native valve to secure the prosthetic valve with respect to the native valve.

According to another example ("Example 42"), further to Example 41, the prosthetic valve includes a plurality of anchor members extending from the support portion that are each biased to extend radially outward from the support portion, the method further comprising engaging the plurality of anchor members with tissue associated with the native valve to secure the prosthetic valve with respect to the native valve.

According to another example ("Example 43"), further to Examples 41 or 42, the support portion includes a frame and the anchor member is biased to extend at an angle of greater than 15 degrees relative to a central longitudinal axis of the frame.

According to another example ("Example 44"), further to any of Examples 41 to 43, the frame includes a plurality of frame members the define a plurality of distal-facing apices, and further wherein the anchor member extends proximally from the frame adjacent one of the distal-facing apices.

According to another example ("Example 45"), further to Example 44, the prosthetic valve is in a diametrically compacted state including the support portion being diametrically compacted and the anchor member being constrained in a compacted configuration with the support portion during delivering of the prosthetic valve to the native valve in the body of the patient.

According to another Example ("Example 46"), further to Example 45 the anchor member is configured to be interleaved in spaces between adjacent frame members of the support portion when the prosthetic valve is in the diametrically compacted state.

According to another example ("Example 47"), further to any of Examples 41 to 46, engaging the anchor member with tissue associated with the native valve to secure the prosthetic valve with respect to the native valve includes engaging the anchor member with at least one of a base of a native leaflet and a native sinus of the native valve.

According to another example ("Example 48"), further to any of Examples 41 to 47, engaging the anchor member with tissue associated with the native valve to secure the prosthetic valve with respect to the native valve includes at least one of displacing and puncturing one or more native leaflets of the native valve such that the anchor member resides in a native sinus of a native valve structure.

According to another example ("Example 49"), further to any of Examples 41 to 48, the native valve is an aortic valve of the patient.

According to another example ("Example 50"), further to any preceding Example, the prosthetic valve includes a plurality of frame members that define a plurality of rows of closed cells, including a distal row of closed cells and a proximal row of closed cells located proximal to the distal row of closed cells, wherein each of the closed cells of the distal row of closed cells includes at least two proximal-facing apices.

According to another example ("Example 51"), further to any preceding Example, the frame of the prosthetic valve has a distal row of a plurality of rows of frame members that extends distally to define a frame member distal boundary that is proximate to, at the same level as, or distal to a commissure post distal boundary of the prosthetic valve such that the distal row of the plurality of rows of frame members provides support to the commissure posts during operation of the prosthetic valve.

According to another example ("Example 52"), further to any preceding example, each of the plurality of leaflets defines two termini at an intersection of a leaflet free edge and a leaflet attachment region, the leaflet attachment region of each leaflet being coupled to the frame at a commissure attachment region of the frame such that the leaflet attachment regions adjacent the termini of two adjacent leaflets diverge relative to each other.

According to another example ("Example 53"), further to any preceding Example, the frame defines a pair of commissure attachment regions that diverge relative to each other toward a commissure post tip, and each leaflet is coupled to one of the commissure attachment regions such that adjacent leaflets define diverging free edges adjacent the commissure attachment regions.

According to another example ("Example 54"), further to any preceding Example, the frame defines a pair of adjacent commissure attachment regions that diverge relative to each other from a location away from a commissure post tip in an outflow direction towards the commissure post tip and a pair of adjacent leaflets of the plurality of leaflets is coupled to a respective one of the pair of adjacent commissure attachment regions such that the respective leaflet free edges of the pair of adjacent leaflets diverge from another at the adjacent commissure attachment regions when the pair of adjacent leaflets are in a closed, coapted configuration.

According to another example ("Example 55"), further to any preceding Example, each leaflet is attached to the frame such that adjacent leaflet free edges at the frame diverge relative to each other.

According to another example ("Example 56"), further to any preceding Example, each leaflet is attached to the frame at a diverging region of the frame such that adjacent leaflet free edges at the frame diverge relative to each other, wherein stress within each leaflet along the diverging region is reduced more than 40% relative to a non-diverging attachment when exposed to peak closing pressures of about 135 mmHg on the outflow face of the leaflet.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 1 is an isometric view of a prosthetic valve and FIG. 2 is a side view of the prosthetic valve, according to some embodiments.

FIG. 3 is a side view of a frame of a support structure of a prosthetic valve at a first rotational orientation and FIG. 4 is a side view of the frame at a second rotational orientation, according to some embodiments.

FIG. 13 is an enlarged view of a portion of a prosthetic valve near a commissure post during assembly of a leaflet construct to the commissure post and a prosthetic valve support structure, according to some embodiments.

FIGS. 14A to 18C illustrate comparative modeling of radial inward compressive loading of prosthetic valves, according to some embodiments.

FIG. 19 show optional features of commissure posts, according to some embodiments.

FIGS. 20 to 23 show optional constraint eyelets for prosthetic valve frames, according to some embodiments.

FIGS. 32 to 34 are illustrative of distal row frame element features for prosthetic valves, according to some embodiments.

FIGS. 41 to 43 are illustrative of potential modifications for commissure attachment regions of prosthetic valves, according to some embodiments.

Figure 5:
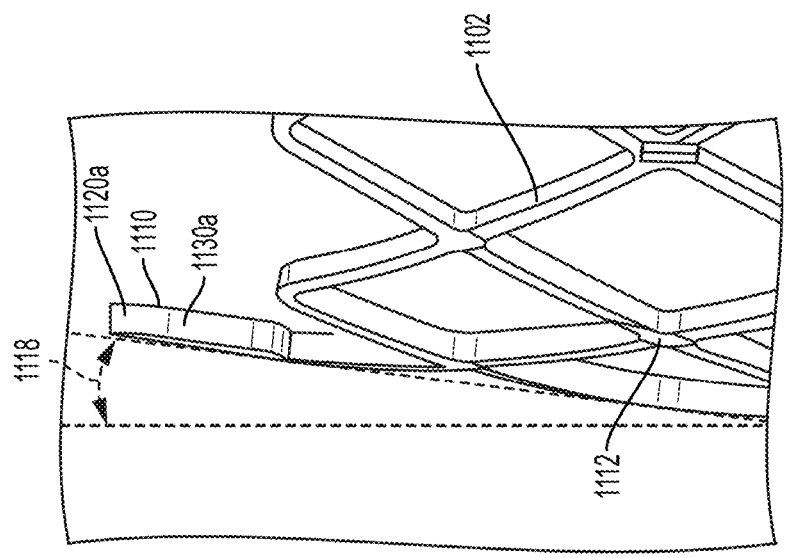
FIGS. 5 and 6 are enlarged, front and side views of a commissure post of a prosthetic valve frame, according to some embodiments.

Persons skilled in the art will readily appreciate the accompanying drawing figures referred to herein are not necessarily drawn to scale, but may be exaggerated or represented schematically to illustrate various aspects of the present disclosure, and in that regard, the drawing figures should not be construed as limiting.

DETAILED DESCRIPTION

The present disclosure relates to prosthetic valves used for cardiac valve replacement (e.g., for treating a failing or otherwise defective aortic or mitral valve) or other applications associated with native valve or other valve orifices, and related systems, methods, and apparatuses. In some associated treatment methods, the prosthetic valve is utilized to treat valve stenosis (e.g., aortic valve stenosis) and/or valve insufficiency (e.g., aortic valve insufficiency). In various examples, the prosthetic valve is operable as a one-way prosthetic valve that defines a valve orifice into which leaflets open to permit flow and close so as to block or occlude the valve orifice and partially or entirely prevent flow in response to differential fluid pressure.

In the instant disclosure, the examples are primarily described in association with transcatheter cardiac valve applications, although it should be readily appreciated features of such examples are equally applicable to prosthetic valves or mechanisms of similar structure and/or function, including surgically implanted valves. Moreover, prosthetic valves according to the instant disclosure can be applied in non-cardiac applications, such as respiratory or gastrointestinal tract applications. Implantable valve orifices include anatomical structures into which a prosthetic valve can be placed and include, but are not limited to, a location from which a cardiac valve may or may not have been surgically removed. Other anatomical structures that can receive a prosthetic valve include, but are not limited to, veins, arteries, ducts, and shunts, for example. In addition to native valve locations, a valve orifice or implant site may also refer to a location in a synthetic or biological conduit that may receive a prosthetic valve. Generally, the term "distal" is used in the disclosure to refer to the outflow end (distal end) or outflow direction of a prosthetic valve, and in turn the term "proximal" is used to refer to the inflow end of a prosthetic valve, or a direction opposite the direction of primary flow through the prosthetic valve.

FIG. 1 is an isometric view of a prosthetic valve 100 and FIG. 2 is a side view of the prosthetic valve 100, according to some embodiments. As shown, the prosthetic valve 100 includes a support structure 102 (also described as a frame assembly), a leaflet construct 104 (also described as a leaflet assembly), and a sealing construct 106 (also described as a sealing cuff). A variety of other features used with such types of prostheses, such as radiopaque marker bands (not shown), are also contemplated.

As shown, the prosthetic valve 100 defines a central longitudinal axis Xv, an inner side 108 (FIG. 1) corresponding to a central lumen and an outer side 110 (FIG. 1) corresponding to the exterior of the prosthetic valve 100 and extends from a proximal end 112 (FIG. 2) to a distal end 114 (FIG. 2). The prosthetic valve 100 also has an inflow side $I_s$ (FIG. 2) into which fluid (e.g., blood) flows and an outflow side $O_s$ (FIG. 2) out of which blood flows. In terms of basic operation, the leaflet construct 104 of the prosthetic valve 100 has free edges that flatten together (e.g., in a Y-shaped pattern in the case of three leaflets when viewed from the top), which can also be described as coaptation of the leaflet construct 104 prosthetic valve 100. In particular, as the free edges of the leaflet construct 104 come together the prosthetic valve 100 closes. The prosthetic valve 100 closes in this fashion when the pressure of the blood on the outflow side $O_s$ (FIG. 2) is greater than the pressure of the blood on the inflow side $I_s$ (FIG. 2) of the prosthetic valve 100. The free edges of leaflet construct 104 move apart to open the prosthetic valve 100 and to let blood flow through the prosthetic valve 100 from the inflow side $I_s$ when the pressure of the blood on the inflow side $I_s$ of the prosthetic valve 100 is greater than the pressure on the outflow side $O_s$ of the prosthetic valve 100.

As shown, the support structure 102 of the prosthetic valve 100 includes a frame 1102 (also described as a framework), a cover 1104 (also described as an attachment element), and a plurality of constraint retainers 1106 (also described as constraint guides). In various examples, the support structure 102 serves to operatively support the leaflet construct 104 in a desired location within a patient (not shown), provides features for securing and maintaining the prosthetic valve 100 to a delivery system (not shown), and other additional or alternative features as desired.

FIG. 3 is a side view of the frame 1102 of the support structure 102 at a first rotational orientation and FIG. 4 is a side view of the frame 1102 at a second rotational orientation, according to some embodiments. The frame 1102, and thus the support structure 102 along with the leaflet construct 104, is optionally collapsible to a reduced profile, delivery configuration and then expandable (e.g., self-expanding or expanded by the application of an internal force, such as by balloon expansion) in situ. As shown in FIG. 2, the frame 1102 is optionally annular, defining a tapered cylinder (e.g., a cone), also described as a tapered cylindrical shape, and has a central longitudinal axis Xf, which corresponds to and is coaxial with the central longitudinal axis of the prosthetic valve Xv (FIG. 2) and is described interchangeably as the central longitudinal axis Xf of the support structure 102, according to some embodiments. As will be further described, the tapered shape of the frame 1102 may be beneficial for a variety of reasons.

Although the frame 1102 generally defines a circular transverse cross-section in an unloaded state (e.g., when not under a transverse load), it should be understood that any variety of cross-sections (e.g., oval- or rectangular-shaped) are also contemplated. The frame 1102 has an inner side 1110 and an outer side 1112 opposite the inner side 1110. The inner side 1110 faces toward the central longitudinal axis Xf, and the outer side 1112 faces outwardly, or away from the central longitudinal axis Xf. The frame 1102 extends from a distal end 1114 (also described as an outflow end) to a proximal end 1116 (also described as an inflow end), the distal end 1114 having a first diameter and the proximal end 1116 having a second larger diameter such that the frame 1102 has a diametric taper of decreasing diameter in a distal direction between the distal end 1114 and the proximal end 1116, the diametric taper defining a taper angle 1118 relative to the central longitudinal axis Xf of the frame 1102 (as well as relative to a right angle cylinder) when the frame 1102, and the prosthetic valve 100, is in an unloaded state. As shown, the taper angle 1118 is relatively constant (linear), although non-constant tapers (e.g., varies with one or more curved or angled segments) are contemplated, as further described.

As shown, the frame 1102 includes a plurality of commissure posts 1120 and a plurality of frame members 1122. As shown, the plurality of commissure posts are generally located toward, and are configured to support a region of the leaflet construct 104 that coapts, or a coaptation region of the leaflet construct 104. The plurality of frame members 1122 generally define a collapsible and expandable arrangement, and also serve to support one or more portions of the leaflet construct 104 as desired.

In some embodiments, the plurality of commissure posts 1120 are spaced from one another, and arranged at desired locations around a circumference of the frame 1102. As shown, the plurality of commissure posts 1120 are angled inwardly toward the central longitudinal axis Xf, following the taper angle 1118, although other configurations (e.g., angled more inwardly, non-angled or angled outwardly from the central longitudinal axis Xf) are also contemplated. Although as best seen in FIG. 4, three commissure posts 1120 are shown, any number of commissure posts are contemplated. The plurality of commissure posts 1120 define circumferentially-adjacent ones, or simply adjacent ones of the plurality of commissure posts 1120 moving about the perimeter of the frame 1102.

Figure 6:
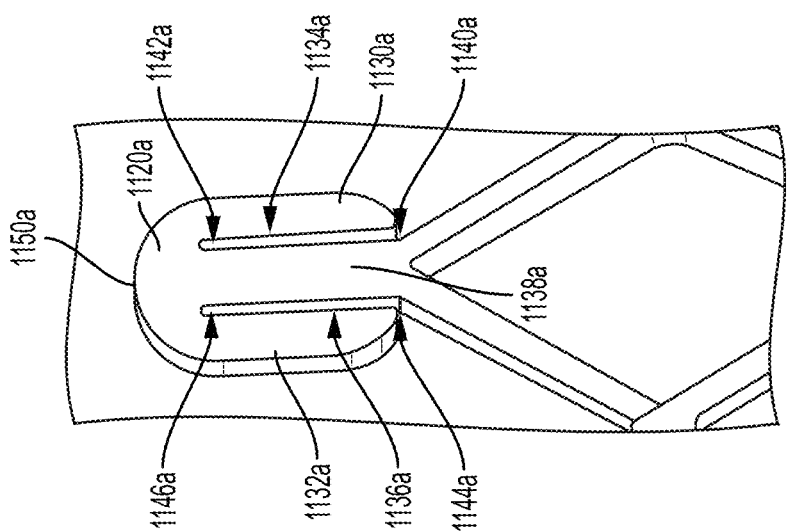

As shown, other than location and orientation, each of the commissure posts 1120 has a similar design, although examples where the commissure posts 1120 differ from one another in various respects are also contemplated. Regardless, for ease of understanding, the features of each of the commissure posts 1120 will be described in association with a first commissure post 1120a, enlarged views of which is shown in FIGS. 5 and 6. The features of the first commissure post 1120a will generally be referenced with a numeral followed by an "a." Similar features of a second commissure post may be subsequently referenced with the same numeral as the first commissure post, but followed by a "b." Similar features of a third commissure post may be subsequently referenced with the same numeral as the first commissure post 1120a, but followed by a "c." Similarly, when features of each of the plurality of commissure posts 1120 are referenced collectively, those features are referenced with the same numeral as identified for the first commissure post 1120a, but not followed by a letter.

As shown in FIG. 5, the first commissure post 1120a, includes a first leg 1130a, a second leg 1132a, a first slot 1134a, which can also be described as a first post slot, and a second slot 1136a, which can also be described as a second post slot. The first slot 1134a and the second slot 1136a are each located between the first leg 1130a and the second leg 1132a. As shown, the first commissure post 1120a also includes an intermediate leg 1138a positioned between the first leg 1130a and the second leg 1132a. The first commissure post 1120a defines the first slot 1134a between the first leg 1130a and the intermediate leg 1138a and the second slot 1136a between the second leg 1132a and the intermediate leg 1138a. The first commissure post 1120a has an outer side corresponding to the frame outer side 1112 (FIG. 3) and a post inner side corresponding to the frame inner side 1110 (FIG. 3).

As shown, the first leg 1130a and the second leg 1132a extend longitudinally, or in a longitudinal direction. As shown in FIG. 6, the first leg 1130a and the second leg 1132a (FIG. 5) extend in a longitudinal direction that is parallel to the taper angle 1118 of the frame 1102 (FIG. 3). In other examples, the first leg 1130a and the second leg 1132a extend longitudinally, but at a different angular offset relative to the central longitudinal axis Xf (e.g., parallel, more inwardly offset, or more outwardly offset).

As shown, each of the first slot 1134a and the second slot 1136a extends through a thickness of the first commissure post 1120a, from the inner side 1110 of the frame 1102 to the outer side 1112 of the frame 1102. The slots 1134a, 1136a are formed through the frame in a generally radial direction relative to a central longitudinal axis Xf (FIG. 2) of the frame 1102. In various examples, one or both of the first slot 1134a and the second slot 1136a extend in a longitudinal direction, although the first slot 1134a and the second slot 1136a generally follow the taper angle 1118. In other examples, one or both of the first slot 1134a and the second slot 1136a extend longitudinally, but at some offset relative (e.g., angularly offset relative to the taper angle 1118 and/or angularly offset transversely relative to the central longitudinal axis Xf). As shown, one or both of the first slot 1134a and the second slot 1136a are elongate in shape, with lengths, or heights, much greater than their widths (e.g., more than 2×, 5×, 10×, 20×, or 30×, although a variety of dimensions are suitable).

In some examples, the first slot 1134a extends from a first end 1140a to a second end 1142a and the second slot 1136a extends from a first end 1144a to a second end 1146a. As shown, the first ends 1140a, 1144a are open and the second ends 1142a, 1146a are closed. For example, the first ends 1140a, 1144a are "open" in the sense that it opens to a much wider area in the frame 1102 (e.g., more than 5×, 10×, or 20×), whereas the second ends 1142a, 1146a are "closed" in the sense that it terminates at the width of the first slot 1134a and the second slot 1136a. The widths of the first slot 1134a and the second slot 1136a are generally selected to allow a desired number of passes or loops of leaflet material through the first slot 1134a and the second slot 1136a, as subsequently described.

As shown in FIG. 5, in some embodiments, the first commissure post 1120a defines a distal end 1150a that is rounded and otherwise configured to be atraumatic to tissue. The plurality of commissure posts 120, and in particular the distal ends (e.g., distal end 1150a) of the plurality of commissure posts 1120 also extend distally to define a commissure post distal boundary 1152 (FIG. 4). In general terms, the commissure post distal boundary 1152 approximates a distal boundary of the leaflet construct 104, which is attached to the commissure posts 1120.

In some embodiments, the plurality of frame members 1122 define a collapsible (e.g., elastically) and expandable (e.g., self-expanding or balloon expandable) framework, and also serve to support one or more portions of the leaflet construct 104 as desired. As shown in FIG. 3, the plurality of frame members 1122 define a plurality of rows of frame members 1224 defining an undulating, alternating pattern of proximal-facing apices 242 pointing in a proximal direction and distal-facing apices 238 pointing in a distal direction. In some embodiments, the plurality of rows of frame members 1224 include a proximal row 1230 toward the proximal end 1116 of the frame 1102 a distal row 1232 toward the distal end 1114 of the frame 1102, and at least one intermediate row 1234 positioned intermediate the distal row 1232 and proximal row 1230. As shown in FIG. 3, there are four rows of frame members 1224, although greater or fewer numbers are contemplated (e.g., 2, 4, 12, 20).

As shown, the distal row 1232 of the plurality of rows of frame members 1224 extends distally to define a frame member distal boundary 1236. As shown, the commissure post distal boundary 1152 is located distal to the frame member distal boundary 1236, with the plurality of commissure posts 1120 generally extending more distally than the plurality of rows of frame members 1224. In some embodiments, such a configuration leaves portions of the leaflet construct 104 (FIG. 1) outwardly exposed between the plurality of commissure posts 120 (e.g., the coaptation region), although other features may be incorporated to transversely "cover" or protect the leaflet construct 104 from inward tissue ingress, such as one or more posts or other distal projections (e.g., such as the atraumatic posts 2120 in FIG. 23). Regardless, as shown in FIG. 2, leaflet construct 104 extends distal to the frame member distal boundary 1236. Such a feature may provide additional circumferential space for the plurality of commissure posts 120 to fit into when the prosthetic valve 100 is diametrically compacted into a reduced diameter, delivery configuration.

The plurality of rows of frame members 1224 each define an undulating pattern of distal-facing apices 238 each having an apex angle 240 and proximal-facing apices 242 each having an apex angle 244. For reference, the distal-facing apices 238 point in the distal direction and the proximal-facing apices 242 point in the proximal direction.

In various examples, each of the apex angles 240 of each of the distal-facing apices 238 has a value that is approximately the same in more than one of the plurality of rows of frame members 1224 (e.g., the same approximate value in each of the distal row of frame members 1232, the proximal row of frame members 1230, and/or the intermediate row of frame members 1234). For example, in some embodiments, each the apex angles 240 are within 10% of a common apex angle defined by the plurality of rows of distal-facing apices 238. In other embodiments, each of the apex angles is within 5%, 15%, 20%, or some other value of a common apex angle. In some examples, the common apex angle is 30 degrees, although any of a variety of common apex angles is contemplated (e.g., 10, 15, 20, 30, 40, 45, 50, 60, 90 degrees and ranges between any of those vales).

In various examples, each of the apex angles 244 of each of the proximal-facing apices 242 has a value that is approximately the same in more than one of the plurality of rows of frame members 1224 (e.g., the same approximate value in the distal row of frame members 1232, the proximal row of frame members 1230, and/or the intermediate row of frame members 1234). For example, in some embodiments, each of the apex angles 244 are within 10% of a common apex angle defined by the plurality of rows of proximal-facing apices 242. In other embodiments, each of the apex angles is within 5%, 15%, 20%, or some other value of a common apex angle. In some examples, the common apex angle is 30 degrees, although any of a variety of common apex angles is contemplated (e.g., 10, 15, 20, 30, 40, 45, 50, 60, 90 degrees and ranges between any of those values).

In some examples, the apex angles 240 and/or the apex angles 244 of one or more columns of closed cells 1238 defined by the plurality of frame members 1224 are approximately the same as another one of the columns of closed cells 1238. For example, the apex angles of one or more columns is optionally within 10% of a common apex angle defined by the one or more columns of closed cells 1238 of proximal-facing apices 242 and/or distal-facing apices 238. In other embodiments, each of the apex angles is within 5%, 15%, 20%, or some other value of a common apex angle. In some examples, the common apex angle is 30 degrees, although any of a variety of common apex angles is contemplated (e.g., 10, 15, 20, 30, 40, 45, 50, 60, 90 degrees and ranges between any of those values).

As shown in FIG. 3, the frame 1102 also includes a plurality of rows of closed cells 1240 defined by the plurality of frame members 1224. The plurality of rows of frame members 1224 generally intersect with one another at intersection locations P to define the plurality of rows of closed cells 1240. As shown in the example of FIG. 4, each of the plurality of rows of closed cells 1240 has a proximal end 1242, a distal end 1244, and a cell height 1246 between the distal end 1244 and the proximal end 1242 and a cell width 1248 perpendicular to the cell height 1246. Moreover, each of the plurality of rows of closed cells has a first lateral-facing apex 250 defining an apex angle 252 and a second lateral facing-apex 254 opposite the first lateral-facing apex 250 and defining an apex angle 256.

In a similar manner to the apex angles 240 and the apex angles 244, in various examples, each of the apex angles 252 and/or apex angles 256 of has approximately the same value between one or more of the plurality of rows of closed cells 1240 and/or columns of closed cells 1238 (e.g., within 10% of a common apex angle, although other values such as values within 5%, 15%, 20%, or some other value of a common apex angle are contemplated). In some examples, the common apex angle is 30 degrees, although any of a variety of common apex angles is contemplated (e.g., 10, 15, 20, 30, 40, 45, 50, 60, 90 degrees and ranges between any of those values).

In some examples, the apex angles 240 and/or the apex angles 244 of one or more of the plurality of columns of closed cells 1238 and/or one or more of the plurality of rows of the closed cells 1240 are approximately the same as another one of the plurality of columns of closed cells 1238 and/or the plurality of rows of the closed cells 1240 (e.g., within 10% of a common apex angle, although other values such as values within 5%, 15%, 20%, or some other value of a common apex angle are contemplated). In some examples, the common apex angle is 30 degrees, although any of a variety of common apex angles is contemplated (e.g., 10, 15, 20, 30, 40, 45, 50, 60, 90 degrees and ranges between any of those values).

As shown in FIG. 3, the plurality of rows of closed cells 1240 includes a proximal row of closed cells 1250 at the proximal end 1116 of the frame portion 1210, a distal row of closed cells 1252 toward the distal end 1114 of the frame portion 1210, and at least one intermediate row of closed cells 1253 intermediate the distal row of closed cells 1252 and the proximal row of closed cells 1250. Although three rows of closed cells 1240 are shown, greater or fewer numbers are contemplated (e.g., greater or few number of intermediate rows of closed cells 1253).

As shown, the cell heights 1246 of the distal row of closed cells 1252 are each less than the cell heights 1246 of the proximal row of closed cells 1250. Additionally, each of the cell heights 1246 of the intermediate row of closed cells 1253 are less than the cell heights 1246 of the proximal row of closed cells 1250 and greater than the cell heights 1246 of the distal row of closed cells 1252.

As shown, the cell widths 1248 of the distal row of closed cells 1252 are each less than the cell widths 1248 of the proximal row of closed cells 1250. Additionally, each of the cell widths 1248 of the intermediate row of closed cells 1253 are less than the cell widths 1248 of the proximal row of closed cells 1250 and greater than the cell widths 1248 of the distal row of closed cells 1252.

In various of the foregoing examples, by balancing the various apex angles (e.g., the apex angles 240, the apex angles 244, the apex angles 252, and/or the apex angles 256), such as by having the apex angles 240 be within 10% of one another, the apex angles 244 be within 10% of one another, the apex angles 252 be within 10% of one another, and the apex angles 256 be within about 10% of one another), while increasing the cell heights 1246 and increasing cell widths 1248 in a proximal direction helps balance compaction forces needed toward the proximal end 1116 relative to the compaction forces necessary at the distal end 1114 for diametrically compacting the prosthetic valve 100 to a compact delivery configuration. In some examples, the compaction forces required toward the proximal end 1116 are substantially the same as, or less than, the compaction forces required toward the distal end of the prosthetic valve 100.

Figure 7:
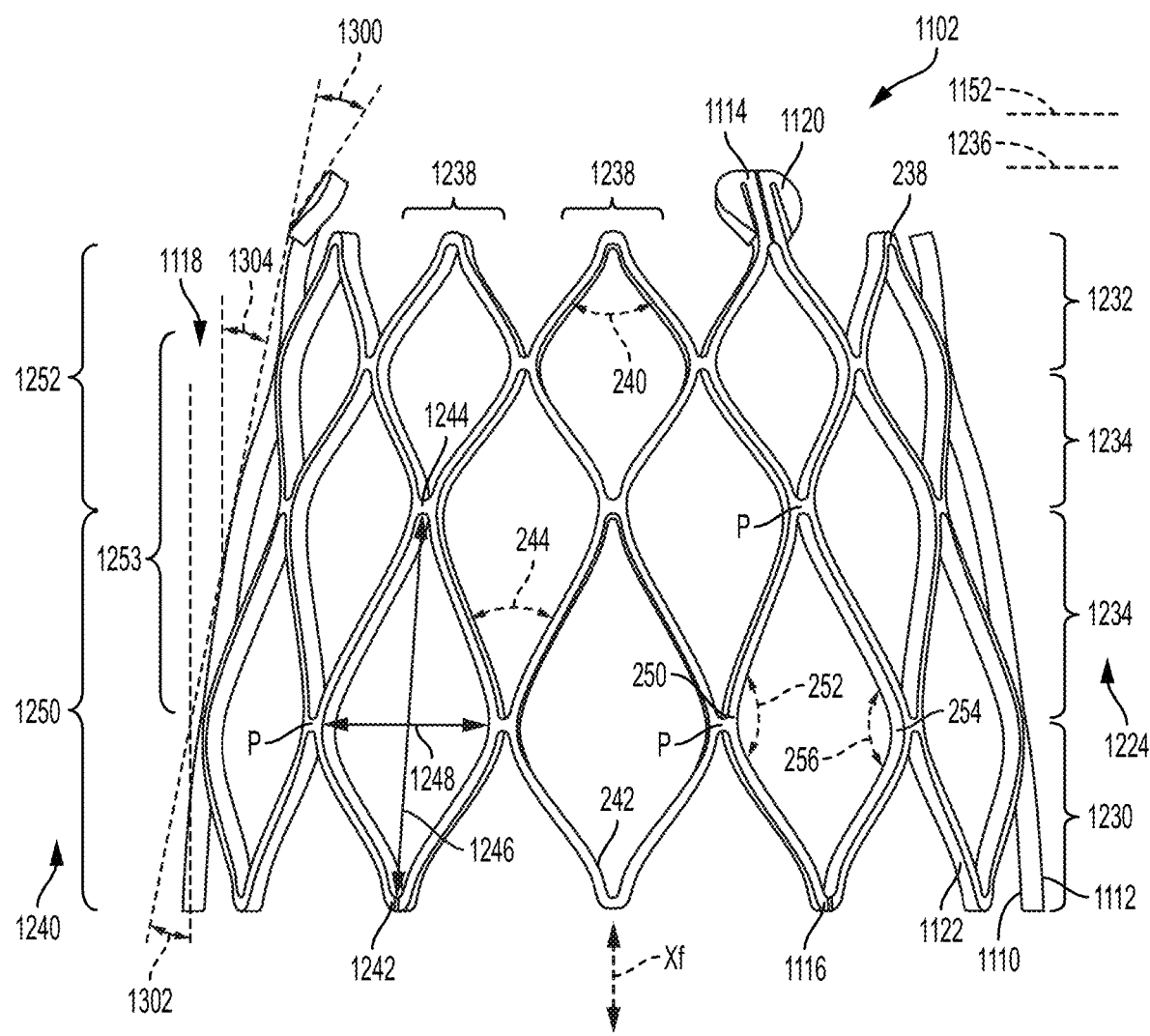
FIG. 7 shows additional features for a frame of a prosthetic valve support structure, according to some embodiments.

FIG. 7 shows additional features for the frame 1102 of the support structure 102, according to some embodiments. The foregoing description of the frame 1102 applies fully to the frame 1102 shown in FIG. 7. For reference, the additional features shown for the frame 1102 in FIG. 7 include a more curved shape for the frame members 1122 as a result of a non-linear change in the cell widths 1248 along the cell heights 1246 (e.g., as compared to the straighter pattern shown in FIGS. 3 and 4) and the diametric taper exhibited by the frame 1102, which is shown to include three, distinct tapers, as opposed to a single taper shown in FIGS. 3 and 4 for the frame 1102. From the foregoing, it should be readily understood that the previous description of the other features of the frame 1102 applies fully. For reference purposes, the apex angles 240, the apex angles 244, the apex angles 252, and the apex angles 256 are determined by drawing straight lines between the various apices of the plurality of rows of closed cells 1240.

With the foregoing in mind, as shown in FIG. 7, the frame 1102 includes a diametric taper in which the taper angle varies 1118 between the distal end 1114 and the proximal end 1116 relative to the central longitudinal axis Xf of the frame 1102 when the prosthetic valve 100 is in an unconstrained, or unloaded state. For example, the taper angle 1118 optionally includes a distal taper angle 1300 corresponding to the plurality of commissure posts 1120, a proximal taper angle 1302 corresponding to the proximal row 1230 of the plurality of rows of frame members 1224, and an intermediate taper angle 1304 between the distal taper angle 1300 and the proximal taper angle 1302 that is defined by the intermediate rows 1234 and the distal row 1232, according to some embodiments.

As shown, the distal taper angle 1300 is greater than the intermediate taper angle 1304, and the intermediate taper angle 1304 is greater than the proximal taper angle 1302. In some examples, one or more of the distal taper angle 1300, the intermediate taper angle 1304, and the proximal taper angle 1302 is the same. In some examples, the proximal taper angle is zero (e.g., parallel to the central longitudinal axis Xf of the frame 1102).

Figure 8:
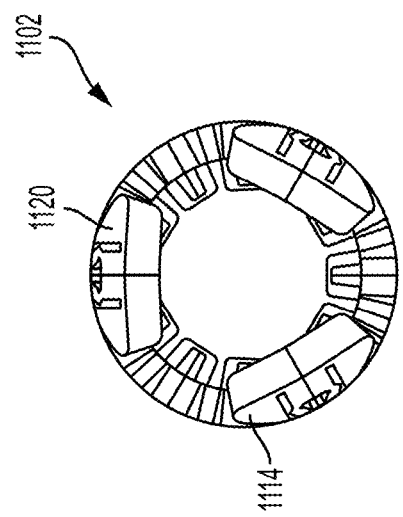
FIG. 8 is an end view of a prosthetic valve frame from a distal end and FIG. 9 is a side view of the frame, both of which show the frame in a diametrically compacted, delivery state, according to some embodiments.
Figure 9:
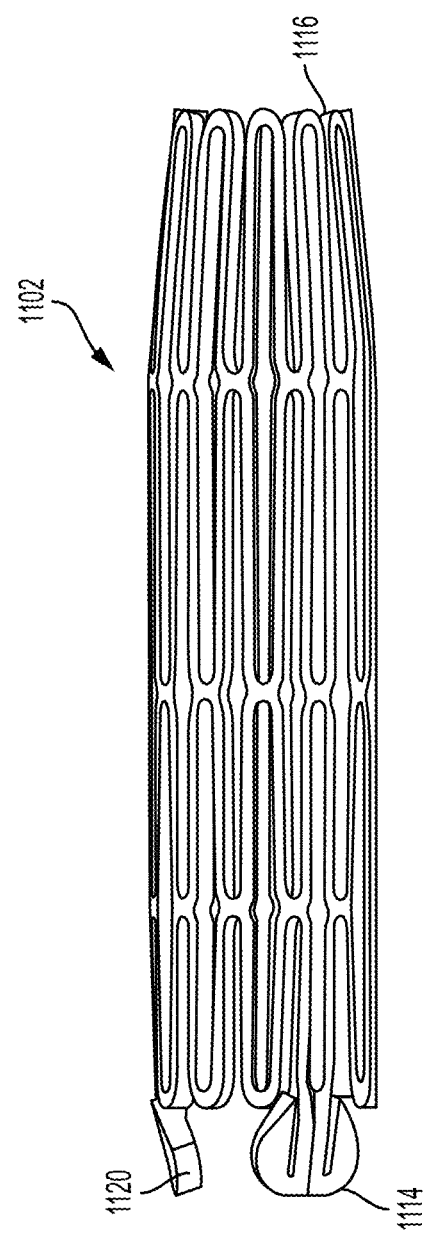

FIG. 8 is an end view of the frame 1102 from the distal end 1114 and FIG. 9 is a side view of the frame 1102, both of which show the frame 1102 in a diametrically compacted, delivery state. Although other portions of the prosthetic valve 100 are not shown, it should be understood that the configuration shown in FIGS. 8 and 9 is illustrative of compaction of the prosthetic valve 100, according to some embodiments. As shown, the taper angle 1118 (FIG. 7) includes a more inward taper angle toward the central longitudinal axis Xf at both the distal end 1114 and/or the proximal end 1116 than the intermediate portion of the diametric taper as desired. Such proximally tapering designs can be particularly helpful in delivering the prosthetic valve 100 from a delivery system (not shown) when in a diametrically compacted state (e.g., from a sheath of a delivery system or otherwise constrained on a delivery catheter), including avoiding damage to the anatomy during delivery, snagging on the anatomy and/or delivery system, facilitating repositioning or retrieval, or other advantages. Such advantages may also be present when the prosthetic valve 100 is partially or fully deployed. And, a distally tapering design may also assist with such delivery and also help with retraction and/or reorientation of the prosthetic valve 100, including when the prosthetic valve 100 is diametrically compacted and/or partially or fully deployed.

The frame 1102 can be etched, cut, laser cut, stamped, three-dimensional printed or wire wound, among other suitable processes. The frame 1102 can include any metallic or polymeric material, such as an elastically (e.g., nitinol) or plastically (e.g., stainless steel) deformable metallic or polymeric material that is generally biocompatible. Other materials suitable for the frame 1102 include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame 1102 as described herein.

The cover 1104 optionally includes one or more layers of material, such as a membrane, or film material, secured to the frame 1102. In some examples, the cover includes of one or more layers of ePTFE material, although any of a variety of other suitable materials may be employed as desired, including fluoropolymer materials such as PTFE, ePTFE, FEP, and others.

The cover 1104 optionally assists with sealing the prosthetic valve 100 to the surrounding conduit in which it is placed (e.g., valve orifice) and also with securing the leaflet construct 104 to the support structure 102, as subsequently described.

As shown in FIG. 1, in some embodiments, the cover 1104 has one or more rows of apertures 1270 for receiving one or more constraints (such as the constraint 1272 shown in broken lines in FIG. 1) associated with a transcatheter delivery system 6000 as shown in FIG. 32. Examples of suitable transcatheter delivery systems for use as the transcatheter delivery system 6000 can also be found in U.S. Provisional Application Ser. No. 62/579,756, entitled "TRANSCATHETER DEPLOYMENT SYSTEMS AND ASSOCIATED METHODS," filed by Applicant on Oct. 31, 2017, as well as U.S. Provisional Application Ser. No. 62/682,692, entitled "TRANSCATHETER DEPLOYMENT SYSTEMS AND ASSOCIATED METHODS," filed by Applicant on Jun. 8, 2018.

For reference, although only the constraint 1272 is shown, a plurality of constraints are optionally employed (e.g., as shown in FIG. 32 three constraints 1272 are generally indicated in broken lines at positions corresponding to the rows of apertures 1270 and the constraint retainers 1106 shown in FIG. 1). For reference, constraints, such as the constraint 1272, are optionally formed of a filamentary material (e.g., a filament, strand, wire, combinations thereof, and the like).

In some embodiments, as shown in FIG. 2, the prosthetic valve 100 also optionally includes one or more constraint retainers 1106 formed as a loop of material coupled to the support structure 102 (e.g., secured to one or more of the plurality of frame members 1122). In some embodiments, the constraint retainers 1106 are each formed by one or more loops of material, such as polymeric material (e.g., ePTFE fiber), metallic material (e.g., nitinol), or any other material that is biocompatible and suitable for implantation with the prosthetic valve 100. In some examples, the constraint retainers 1106 are formed of filamentary material, such as a filament, strand, or a wire (e.g., polymeric or metallic). In some examples, one or more of the constraint retainers 1106 are formed of a biocorridible or biodegradable material that biocorrodes or bioabsorbs over time following implantation. As shown, the constraint 1272 passes through the constraint retainers 1106 to help secure the constraint 1272 in place and help prevent the constraint 1272 from slipping off the distal end 1114 of the frame 1102.

Although some specific attachment examples are subsequently described, the leaflet construct 104 can be received within and coupled to the support structure 102 using any of a variety of techniques (e.g., bonding, adhering, sewing, and others). The location or position of the leaflet construct 104 along the length of the prosthetic valve 100 is referenced as a leaflet region or leaflet portion of the prosthetic valve 100. The various embodiments described herein may utilize biological, such as bovine or porcine, or synthetic leaflets, such fluoropolymer leaflet constructs. Various embodiments have been found to be advantageous for use with synthetic leaflets, such as fluoropolymer constructs, including for wash out and reduced thrombosis, secure and reliable leaflet construct attachment, and others. Some examples of suitable leaflet constructs can also be found in US 2015/0224231 to Bruchman et al., published Aug. 13, 2015.

Figure 10:
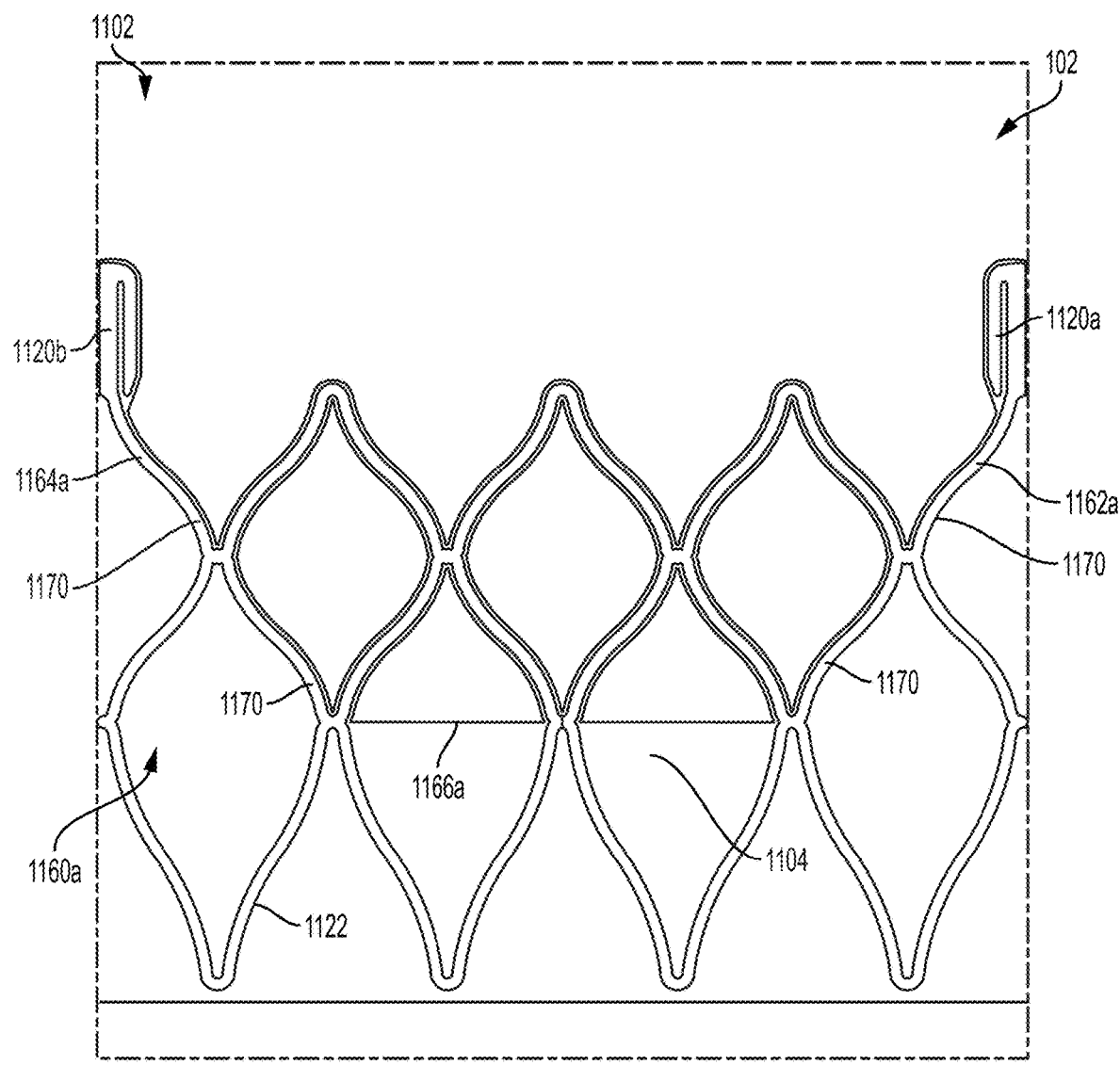
FIG. 10 is an enlarged view of a portion of a prosthetic valve support structure, according to some embodiments.

FIG. 10 is an enlarged view of a portion of the support structure 102 between two adjacent commissure posts 1120 of the frame 1102, according to some embodiments. Similar portions of the support structure 102 are defined between each of the adjacent plurality of commissure posts 1120, according to some embodiments and thus are described collectively with reference to FIG. 10. In FIG. 10, the portion of the support structure 102 is represented in a flattened form for ease of illustration, although it should be understood that the support structure 102 is three-dimensional and generally annular. As shown, the support structure 102 defines a first leaflet attachment region 1160a between the first commissure post 1120a and the second commissure post 1120b, as well as leaflet attachment regions 1160 between the remaining commissure posts 1120.

The leaflet attachment frame members 1170 and the cover 1104 are arranged to support the leaflet construct 104 and to help define a leaflet shapes of the leaflet construct 104. In some embodiments, the plurality of frame members 1122 of the frame 1102 include a plurality of leaflet attachment frame members 1170, or simply leaflet attachment elements, that together with the cover 1104 define the leaflet attachment regions of the prosthetic valve 100, including the first leaflet attachment region 1160a shown in FIG. 10. Each of the leaflet attachment regions is optionally substantially similar and thus are described collectively with regard to the first leaflet attachment region 1160a.

The first leaflet attachment region 1160a defines a first side 1162a, a second side 1164a, and a base 1166a, which is defined at least in part by the cover 1104. As referenced, similar leaflet attachment regions are defined between each of the plurality of commissure posts 1120, according to some embodiments.

According to various examples, other than location and orientation, each of the plurality of leaflets 1180 has a similar design, although examples where the leaflets differ from one another in various respects are also contemplated. Regardless, for ease of understanding, the features of each of the leaflets 1180 will be described in association with a first leaflet 1180a. The features of the first leaflet 1180a will generally be referenced with a numeral followed by an "a." Similar features of a second leaflet may be subsequently referenced with the same numeral as the first leaflet, but followed by a "b." Similar features of a third leaflet may be subsequently referenced with the same numeral as the first leaflet 1180a, but followed by a "c." Similarly, when features of each of the leaflets are referenced collectively, those features are referenced with the same numeral, but not followed by a letter. Similarly, when features of each of the leaflets 1180 are referenced collectively, those features are referenced with the same numeral, but not followed by a letter.

Figure 11:
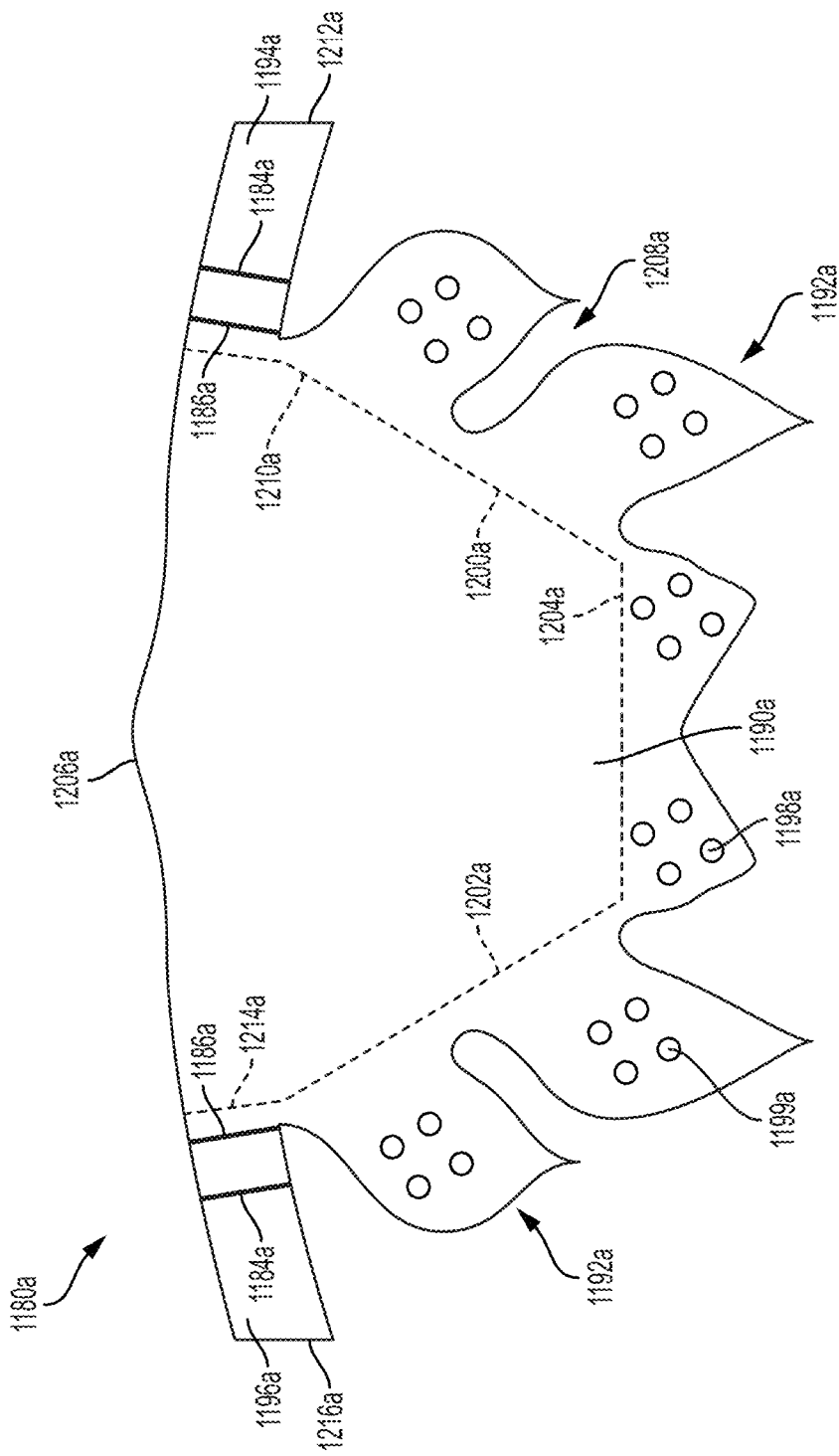
FIG. 11 shows a flattened view of a leaflet of a prosthetic valve leaflet construct, according to some embodiments.

FIG. 11 is a flat view of the first leaflet 1180a of the leaflet construct 104. The first leaflet 1180a is shown from a flattened, plan view prior to assembly with the support structure 102. This flattened plan view can also be described as a cut pattern, or simply a leaflet pattern. From FIG. 11, for example, it should be understood that the leaflet construct 104 is folded and turned into a non-planar shape following attachment to portions of the support structure 102, with each of the plurality of leaflets 1180 being attached circumferentially about the support structure 102. As should be understood from FIG. 10, the plurality of leaflets 1180 are optionally formed as separate components, which are then separately assembled to the support structure 102, although interconnected, continuous leaflet designs are also contemplated. As shown, the plurality of leaflets 1180 are spaced from one another, and arranged, or otherwise distributed at desired locations around a circumference of the leaflet construct 104.

Although three leaflets 1180 are shown in FIG. 1, any number of leaflets is contemplated. Each of the leaflets 1180 define circumferentially-adjacent ones, or simply adjacent ones of the plurality of leaflets 1180 moving about the circumference of the leaflet construct 104. The leaflet construct 104 can be formed in a variety of manners, including cutting a cylinder of polymer material into a desired shape, cutting a sheet of polymer material into a desired shape, and/or molding (e.g., compression or injection molding) the leaflet construct 104 with a desired shape.

As indicated on FIG. 11, the first leaflet 1180a optionally includes a body portion 1190a, a plurality of attachment tabs 1192a extending from the body portion 1190a, a first commissure tab 1194a extending from the body portion 1190a, and a second commissure tab 1196a extending from the body portion 1190a.

The body portion 1190a, also described as a leaflet body, is bounded in broken lines for understanding purposes. The body portion 1190a of the first leaflet 1180a is the moving portion of the first leaflet 1180a in the prosthetic valve 100 (FIG. 1). It should be appreciated that when assembled to the support structure 102, the boundaries of the body portion 1190a are defined and the body portion 1190a takes on a three dimensional shape, rather than the flat shape shown in FIG. 11. As such, the broken lines are provided for general visualization purposes of the body portion 1190a. In various examples, the shape of the body portion 1190a is generally dictated by the lines, or areas of attachment to the support structure 102. The edges of the body portion 1190a generally correspond to fold lines where the attachment tabs 1192a and first commissure tab 1194a and the second commissure tab 1196a are secured to the support structure 102. As will be described below, the leaflet construct 104 may be attached to the support structure 102 using cover 1104 (FIG. 10), which in turn, may contribute to shape defined by the leaflet attachment regions 1160 and the ultimate shape of the body portion 1190a.

As shown in FIG. 11, the body portion 1190a of the first leaflet 1180a has the general shape of an isosceles trapezoid. Regardless of the exact shape, the body portion 1190a generally has a first side 1200a, a second side 1202a, a leaflet base 1204a, and a free edge 1206a opposite the leaflet base 1204a. The body portion 1190a is configured to facilitate coaptating of the first leaflet 1180a with the other leaflets 1180. In general terms, the shape of the body portion 1190a corresponds to the sides and base of the first leaflet attachment region 1160a (FIG. 10). As shown, the two sides 1200a, 1202a diverge from the leaflet base 1204a, and the leaflet base 1204a will be substantially straight in a transverse plane relative to the central longitudinal axis Xf of the support structure 102. In different terms, leaflet base 1204a can be considered to be flat and to extend perpendicular to the central longitudinal axis Xf of the support structure 102 following assembly, although a variety of configurations are contemplated, including leaflet bases that are not flat in the transverse plane.

Although the body portion 1190a is shown to take on the general shape of an isosceles trapezoid, any number of shapes is contemplated, and the body portion 1190a need not be trapezoidal in overall appearance. For example, the body portion 1190a may include a central region that defines a shape substantially that of an isosceles trapezoid, with side regions on each side that have a shape substantially that of a triangle. In still other embodiments, the body portion 1190a may outline a shape that can be described as U-shaped or a V-shapes, depending on the geometric outline defined by the first leaflet attachment region 1160a.

The first leaflet 1180a generally defines a fold over portion 1198a, also described as a fold over region, outside of the body portion 1190a, as demarcated by the broken line in FIG. 11. The fold over portion 1198a of the first leaflet 1180a is the portion that is used to secure the first leaflet 1180a to the support structure 102, where the remaining leaflets 1180 optionally include similar features for securing to the frame 1102. The leaflet attachment frame members 1170 (FIG. 10) fit into a fold that is formed between the body portion 1190a and the fold over portion 1198a. In general terms, the margin of the body portion 1190a adjacent to the support structure 102 extends radially inward from the frame 1102 when coupled to the frame 1102. The body portion 1190a includes enough material between the commissure posts 1120 of the frame 1102 so that the leaflet free edges can come together or coapt in the interior of the prosthetic valve 100 to close the prosthetic valve 100.

As shown, the plurality of attachment tabs 1192a located in the fold over portion 1198a are positioned about a perimeter of the body portion 1190a and are separated from one another by openings 1208a for receiving frame members 1122 (e.g., leaflet attachment frame members 1170) of the frame 1102. As shown, one or more of the plurality of attachment tabs 1192a optionally includes apertures 1199a through the thickness of the attachment tabs 1192a. The apertures 1199a may assist with securing the attachment tabs 1192a to the support structure 102 (e.g., to the frame 1102 and the cover 1104) using adhesives or bonding (e.g., to provide additional surface area for adhesion/bonding), fastening elements (e.g., holes for sutures), or combinations thereof. In some examples, the apertures 1199a are used for alignment purposes, such as to help align one attachment tab (e.g., one of the attachment tabs 1192a of the first leaflet 1180a) over another attachment tab of another leaflet (e.g., one of the attachment tabs 1192b of the second leaflet 1180b) when folding the attachment tabs onto the support structure 102. Similar or additional apertures 1199a may additionally or alternatively be incorporated to reduce mass of the material forming the leaflets 1180, to increase mechanical entanglement of the material forming the leaflets 1180 and any bonding materials used to secure the leaflets 1180 to the support structure 102, or for additional or alternative purposes as desired.

In various examples, the first commissure tab 1194a and the second commissure tab 1196a assist with securing the first leaflet 1180a to the first commissure post 1120a and second commissure post 1120b (FIG. 2). As shown in FIG. 11, the first commissure tab 1194a extends from the first side 1200a of the body portion 1190a and the second commissure tab 1196a extends from a second side 1202a of the body portion 1190a. The first commissure tab 1194a extends from a first end 1210a, also described as a leaflet end, to a terminal end 1212a. Similarly, the second commissure tab 1196a extends from a first end 1214a to a terminal end 1216a. The first commissure tab 1194a and the second commissure tab 1196a are shown as generally rectangular in shape, with a constant width, although tapers (e.g., toward the terminal ends 1212a, 1216a) are also contemplated.

As shown in FIG. 11, the first leaflet 1180a includes a plurality of first retaining elements 1184a and a plurality of second retaining elements 1186a. As shown in FIG. 11, the first leaflet 1180a includes a plurality of first retaining elements 1184a, and a plurality of second retaining elements 1186a. As used herein, a retaining element includes one or more of a strand, filament, monofilament, multifilament (whether braided, woven, twisted or an otherwise associated group of filaments), a bead of material, a thread, a suture, a rolled film, a multilayer lay-up of material, a wire, an embossed or other feature providing the functionality described herein.

The first retaining elements 1184a and/or the second retaining elements 1186a can be formed from polymeric or metallic materials, fluoropolymers, one or more of FEP, PEEK, ePTFE filament(s) (mono- or multi-), nitinol, stainless steel, multiple folds or layers of material (e.g., ePTFE film), combinations thereof, or any of a variety of features configured to resist movement relative to the slot(s).

The first and second retaining elements 1184a, 1186a are optionally molded, heat bonded, or otherwise coupled to the leaflet construct 104 as desired. As used herein, couple means to join, connect, attach, adhere, affix, or bond, whether directly or indirectly, and whether permanently or temporarily.

As shown, the first leaflet 1180a includes first retaining elements 1184a that are located on each of the first commissure tab 1194a and the second commissure tab 1196a. As shown, the first leaflet 1180a also includes second retaining elements 1186a that are located on each of the first commissure tab 1194a and the second commissure tab 1196a.

In some examples, the first retaining elements 1184a are spaced apart from their adjacent second retaining elements 1186a a distance at least as wide as the thickness of a corresponding commissure post 1120 (e.g., 1120a) as measured from the inner side 1110 to the outer side 1112 of the frame 1102.

As previously referenced, the various retaining elements can take a variety of forms. In some examples, one or both of the first and second retaining elements 1184, 1186 are formed as beads of material and/or fibers (e.g., coated fibers) on the commissure tabs of the leaflets 1180. The various retaining elements are optionally bonded to the underlying material of the leaflets 1180, such as by thermal bonding.

Figure 12:
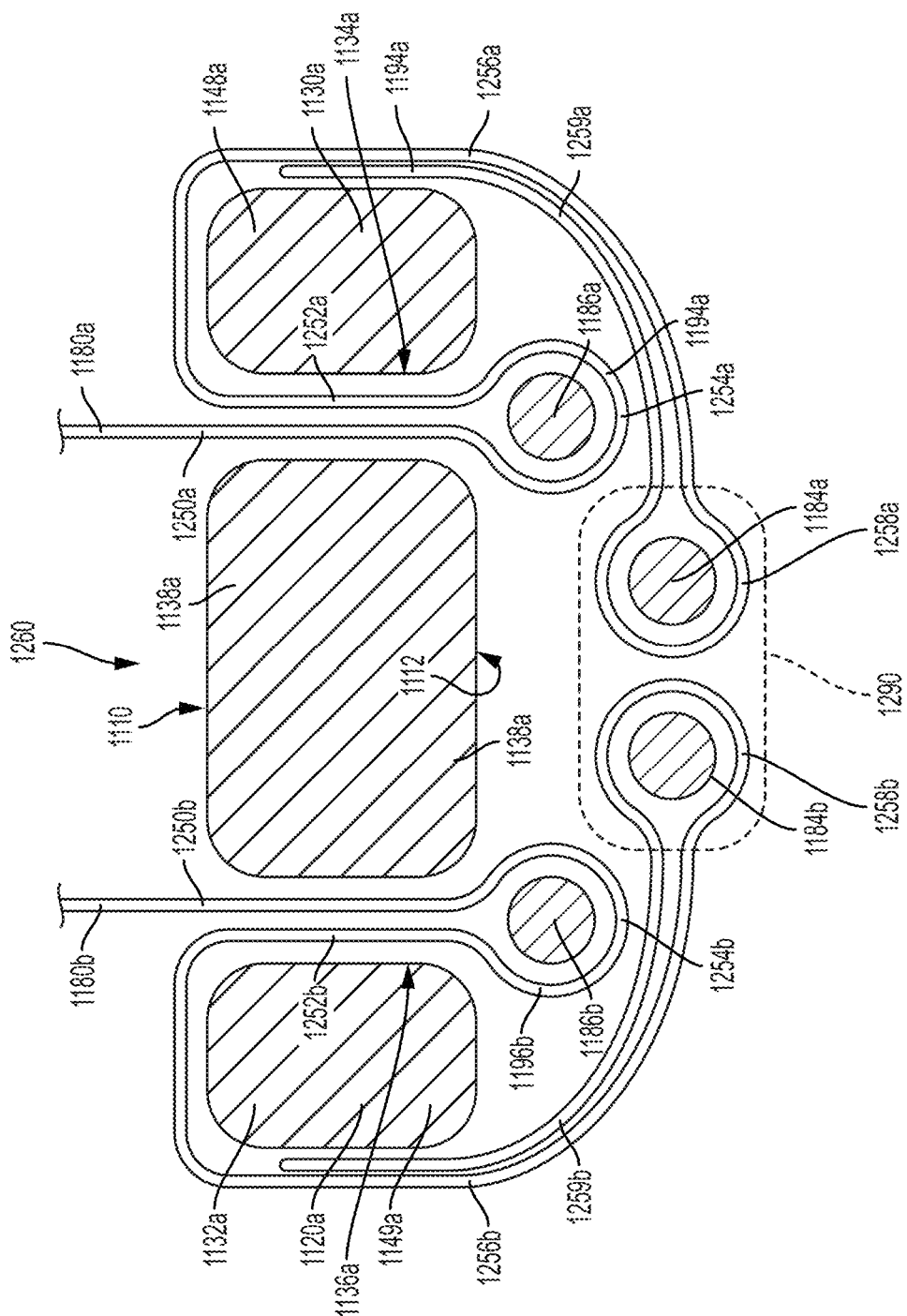
FIG. 12 is a sectional view through a prosthetic valve commissure post, according to some embodiments.

FIG. 12 is illustrative of a leaflet attachment configuration between the plurality of leaflets 1180 and the plurality of commissure posts 1120 of the prosthetic valve 100. In particular, although FIG. 12 shows the first commissure post 1120a, with one side of the first leaflet 1180a and one side of the second leaflet 1180b attached thereto, it should be understood that similar attachment methods are used to attach the remaining commissure tabs of the plurality of leaflets 1180 to respective ones of the remaining commissure posts 1120.

As shown in FIG. 12, the first commissure tab 1194a of the first leaflet 1180a extends through the first slot 1134a a plurality of times (also described as a plurality of passes) and the second commissure tab 1196b of the second leaflet 1180b extends through the second slot 1136a of the first commissure post 1120a a plurality of times (also described as a plurality of passes), with the first retaining elements 1184a, 1184b positioned on the outer side 1112 of the frame 1102, and thus on the outer side 1112 of the first commissure post 1120a.

The second retaining elements 1186a, 1186b are also positioned on the outer side 1112 of the frame 1102, and thus the outer side of the first commissure post 1120a. As shown, the second retaining elements 1186a, 1186b and the plurality of passes of the first and second commissure tabs 1194a, 1196b, respectively, resist being pulled inwardly and outwardly relative to the frame 1102. For example, the first retaining elements 1184a, 1184b and the plurality of passes of the first and second commissure tabs 1194a, 1196b, respectively, cover the second retaining elements 1186a, 1186b and help the assembly being pulled inwardly and outwardly relative to the frame 1102.

As shown, the first commissure tab 1194a of the first leaflet 1180a defines a first pass 1250a through the first slot 1134a (inside-out relative to the first commissure post 1120a) and a second pass 1252a through the first slot 1134a (outside-in relative to the first commissure post 1120a) to define a first loop 1254a through the first slot 1134a. The second retaining element 1186a is positioned within the first loop 1254a to encircle the second retaining element 1186a and form a widened cross-section for the first loop 1254a on the outer side 1112 of the frame 1102. The width of the first loop 1254a is selected to resist, or be restrained from, pulling through the first slot 1134a.

The first commissure tab 1194a of the first leaflet 1180a defines a third pass 1256a around the outside of the first commissure post 1120a, from the inner side 1110 around the first side 1148a to the outer side 1112 and then back from the outer side 1112 to the first side 1148a to define a fourth pass 1259a, the third and fourth passes 1256a, 1259a defining a second loop 1258a passing outside the first commissure post 1120a on the first side 1148a. The first retaining element 1184a is positioned within the second loop 1258a to encircle the first retaining element 1184a and form a widened cross-section for the second loop 1258a on the outer side 1112 of the frame 1102. The width of the second loop 1258a is selected as desired (e.g., to fit against the outer side 1112 between the first leaflet 1180a and the second leaflet 1180b. As shown, the first pass 1250a is positioned adjacent, and opposite the second pass 1252a, and the third pass 1256a and fourth pass 1259a are positioned adjacent each other.

The second commissure tab 1196b defines a similar set of features to those of the first commissure tab 1194a, which are labeled on FIG. 12 for reference. As shown, the second commissure tab 1196b of the second leaflet 1180b defines a first pass 1250b through the second slot 1136a (inside-out relative to the first commissure post 1120a) and a second pass 1252b through the second slot 1136a (outside-in relative to the first commissure post 1120a) to define a first loop 1254b through the second slot 1136a. The second retaining element 1186b is positioned within the first loop 1254b to encircle the second retaining element 1186b and form a widened cross-section for the first loop 1254b on the outer side 1112 of the frame 1102. The width of the first loop 1254b is selected to resist, or be restrained from, pulling through the second slot 1136a.

The second commissure tab 1196b of the second leaflet 1180b defines a third pass 1256b around the outside of the first commissure post 1120a, from the inner side 1110 around the second side 1149a to the outer side 1112 and then back from the outer side 1112 to the second side 1149a to define a fourth pass 1259b, the third and fourth passes 1256b, 1259b defining a second loop 1258b passing outside the first commissure post 1120a on the second side 1149a. The first retaining element 1184a is positioned within the second loop 1258a to encircle the first retaining element 1184a and form a widened cross-section for the second loop 1258b on the outer side 1112 of the frame 1102. The width of the second loop 1258b is selected as desired (e.g., to fit against the outer side 1112 between the first leaflet 1180a and the second leaflet 1180b).

As shown, the second retaining elements 1186a, 1186b, and thus the second loops 1258a, 1258b are secured together (e.g., with an adhesive or one or more fasteners, such as sutures or staples). For example, as shown on or more sutures or other filaments are optionally used to secure the second loops 1258a, 1258b together. In FIG. 12, a secondary coupler 1290 is shown in broken lines secured around the second retaining elements 1186a, 1186b.

As shown, the secondary coupler 1290 is a filament, such as a suture or staple, for securing the second retaining elements 1184a, 1184b together. In other examples, the secondary coupler 1290 includes coating(s) or layer(s) of material over molded or otherwise disposed on the exterior and/or interior side of the frame 1102 to help couple the first loops 1254 and the second loops 1258 to one another and the frame 1102. Similarly, any of the other loop and post arrangements may be coupled with one or more secondary couplers (e.g., by one or more sutures, filaments, layers, and/or coatings). For example, one or more layers of tape may be overwrapped onto first loops 1254 and/or second loops 1258, one or more jackets or covers of material may be placed over and secured to the first loops 1254 and/or second loops 1258, or other techniques may be employed. Generally, such materials may be selected not only to secure the first loops 1254 and the second loops 1258 in place, but may also be employed to form a continuous surface without cracks or other defects, which may help avoid tissue ingrowth and/or thrombus formation where such avoidance is desirable. Similarly, any of the other loop and post arrangements provided in this disclosure may be coupled with one or more secondary couplers (e.g., by one or more sutures, filaments, layers, and/or coatings). With the arrangement shown the second loops 1258a, 1258b can help prevent the first loops 1254a, 1254b from pulling outwardly (radial outward) from the first commissure post 1120a.

The first loops 1254a,b, are optionally described as outer loops and the second loops 1258a,b are also optionally described as outer loops. In some examples, one or more of the passes 1250a,b, 1252a,b, 1256a,b, 1259a,b are coupled to one another (e.g., by heat seating, adhesives, sutures, or other means). Whether bonded or unbonded, the passes can be inserted into the first slot 1134a and second slot 1136a, respectively, with the first retaining elements 1184a,b on the outer side 1112 of the frame 1102 and the second retaining elements 1186a,b on the outer side of the frame 2102 by sliding the first and second commissure tabs 1194a, 1196b into the first slot 1134a and the second slot 1136a through open ends of the slots (not shown, but see the first commissure post 1120a for an example).

In some other examples, the first and second commissure tabs 1194a, 1196b are threaded through the slots 1134a, 1136a and around the sides 1148a, 1149a (e.g., rather than being slid up into the slots 1134a, 1136a and around the first and second legs 1130a, 1132a). Although the described number of passes are shown for each of the commissure tabs in FIG. 12, fewer or greater passes are also contemplated.

With the arrangement shown in FIG. 12, none of the first retaining elements 1184, second retaining elements 1186, first loops 1254, or second loops 1258 resides on the inner side 1110 of the frame 1102. Thus, those features are outside of the flow field and generally do not interfere with blood flow through the prosthetic valve 100.

The remaining commissure tabs of the leaflets 1180 are secured to and supported from the remaining commissure posts 1120. The relatively smooth turns and reinforcement provided by the first and second retaining elements 1184, 1186 reduce stress concentrations at the commissure posts 1120 due to transverse loading of the leaflet construct 104 and help to reduce axial stress concentrations at the attachment interfaces between the commissure posts 1120 and the leaflets 1180.

Also, as shown, the first leaflet 1180a and the second leaflet 1180b are spaced from one another at the inner side 1110 of the frame 1102, which can be described as the leaflets defining a commissure gap 1260 at the first commissure post 1120a. In some embodiments, the prosthetic valve (e.g., prosthetic valve 100) defines similar commissure gaps between each, circumferentially-adjacent leaflets 1180 of the prosthetic valve 100. The commissure gap 1260 helps provide a limited amount of flow to pass between the first and second leaflets 1180a, 1180b near the frame 1102 to help avoid thrombus formation at that location (e.g., whereas a lack of a gap such as the commissure gap 1260 may create a dead flow region susceptible to such thrombosis formation).

FIG. 13 shows an overlay of portions of the prosthetic valve 100 illustrating parts of the frame 1102, the cover 1104, the first leaflet 1180a and the second leaflet 1180b of the leaflet construct 104 in an area of the first commissure post 1120a, for understanding of assembly thereof, where similar concepts apply in assembling the remaining leaflets 1180 to the support structure 102. As referenced above, the leaflet construct 104 (FIG. 11) is attached to the support structure 102 using fold over portions, such as the fold over portion 1198a (FIG. 11) of the first leaflet 1180a. Attachment tabs, such as the attachment tabs 1192a, 1192b of the first leaflet 1180a and the second leaflet 1180b are received through the plurality of rows of closed cells 1240 over portions of the frame 1102 and the cover 1104 and attached over the outer side 1112 of the frame 1102 and the cover 1104 to attach the leaflet construct 104 to the support structure 102.

As should be understood, the attachment tabs 1192a, 1192b are passed through the frame 1102 and folded onto the cover 1104. For example, the lowermost attachment tab(s) 1192a may be folded to a relatively flat area defined by the cover 1104 (e.g., the base 1166a shown in FIG. 10), to define the leaflet base 1204a shown for the body portion 1190a in FIG. 11. In particular, in the case of the first leaflet 1180a, the various attachment tabs are folded over at the first leaflet attachment region 1160a, including the first side 1162a, the second side 1164a, and the base 1166a (FIG. 10). The fold over portions of each of the plurality of leaflets 1180 are then secured to the support structure 102 at each of the leaflet attachment regions 1160 between each of the plurality of commissure posts 1120. The fold over portions can be secured in place using adhesives, sutures, sintering, or by other methods as desired. In some examples, apertures, such as the apertures 1199a are used to assist with bonding (e.g., adhering) and/or to assist with aligning the attachment tabs at their proper positions. In some examples, the shapes of the fold over portions generally correspond to shapes of the plurality of rows of closed cells 1240 (FIG. 7) to assist with proper visual alignment of the leaflet construct 104 onto the support structure.

As shown in FIGS. 1 and 2, the sealing construct 106 includes a sealing member 1500 having a secured portion 1510 that is coupled to the support structure 102 (e.g., to the cover 1104) and an unsecured portion 1512 that is not coupled to the support structure 102. The sealing member 1500 is optionally in the form of a continuous band of material extending about the circumference of the support structure 102. For ease of illustration, the sealing construct 106 is not shown to extend fully to the proximal end 112 of the device, although it should be understood that the sealing construct 106 optionally extends along a desired portion of the prosthetic valve 100, including to the proximal end 112.

The secured portion 1510 optionally includes a proximal region 1520 that is adhered, bonded or otherwise secured to the support structure 102. As referenced above, the proximal region 1520 optionally extends proximally a desired amount, including to the proximal end 112 of the prosthetic valve 100 as desired. As indicated by the broken line, the proximal region 1520 (FIG. 2) is optionally continuous and uninterrupted (e.g., a ring) around a circumference of the support structure 102 (e.g., forming a continuous area of attachment. In other examples, the proximal region 1520 is discontinuous. The secured portion 1510 also optionally includes one or more discrete regions 1522 (FIG. 2) that are bonded, adhered, or otherwise secured to the support structure 102. Moreover, the secured portion 1510 also optionally includes one or more securing tabs 1524 (FIG. 2) that are secured to the support structure 102 and extend longitudinally (e.g., distally) from a distal-facing edge 1532 of the sealing member 1500.

The unsecured portion 1512 optionally includes a distal region 1530 (FIG. 2) of the sealing member which extends to a distal-facing edge 1532 (FIG. 2), at least a portion of which is not secured to the support structure 102. In use, the distal-facing edge 1532 is free to billow, or deflect outwardly a limited amount (e.g., under positive blood pressure) to help the sealing member 1500 positively engage adjacent tissue. This feature may assist with the sealing function of the sealing member 1500 with adjacent tissue, including blocking blood flow and/or facilitating tissue ingrowth, for example. The discrete regions 1522, securing tabs 1524, or other additional or alternative features are optionally employed to help prevent the sealing member 1500 from inverting during deployment and/or in vivo during operation of the prosthetic valve 100. In some examples, the distal-facing edge 1532 is secured to the support structure 102 at a plurality of locations (e.g., at the securing tabs 1524) and remains unsecured from the support structure 102 at a plurality of locations where the distal-facing edge 1532 is free to billow, or deflect outwardly.

FIGS. 14 to 18 show by way of example some of the advantages that are achieved with the tapered diametric profiles described above for the frame 1102, and thus the prosthetic valve 100. With reference to FIG. 2, the leaflet bases of the leaflet construct 104 (e.g., such as the leaflet base 1204a shown in FIG. 11), are located at a first longitudinal location 1600 along the central longitudinal axis Xf of the support structure 102, the frame 1102 defining a leaflet base level diameter at the first longitudinal location 1600. In turn, each the leaflet construct 104 is coupled to the plurality of commissure posts 1120 at a second longitudinal location 1650 along the central longitudinal axis Xf of the support structure 102 that is distal to the first longitudinal location, the frame 1102 defining a commissure level diameter at the second longitudinal location 1650. For reference, the prosthetic valve 100 generally defines a proximal portion 1660 proximal to the first longitudinal location 1600 and that proximal portion 1660 typically encounters a larger amount of the inward radial compressive load (e.g., a majority of the inward radial compressive load) when the prosthetic valve 100 is implanted in a native valve orifice, such as an aortic valve orifice.

As illustrated in FIGS. 14 to 18, the commissure level diameter is less than the leaflet base level diameter when the frame 1102, and thus the prosthetic valve 100, is in an unloaded state. The commissure level diameter is closer in value to the leaflet base diameter when the prosthetic valve 100 is in an operational state (e.g., under an inward radial compressive load) than when the prosthetic valve 100 is in the unloaded state. In particular, the operational state of the prosthetic valve 100 (e.g., following implantation at a native valve orifice) includes the prosthetic valve 100 being subjected to an inward radial compressive force on at least the proximal portion 1660 of the prosthetic valve 100.

Figure 14A:
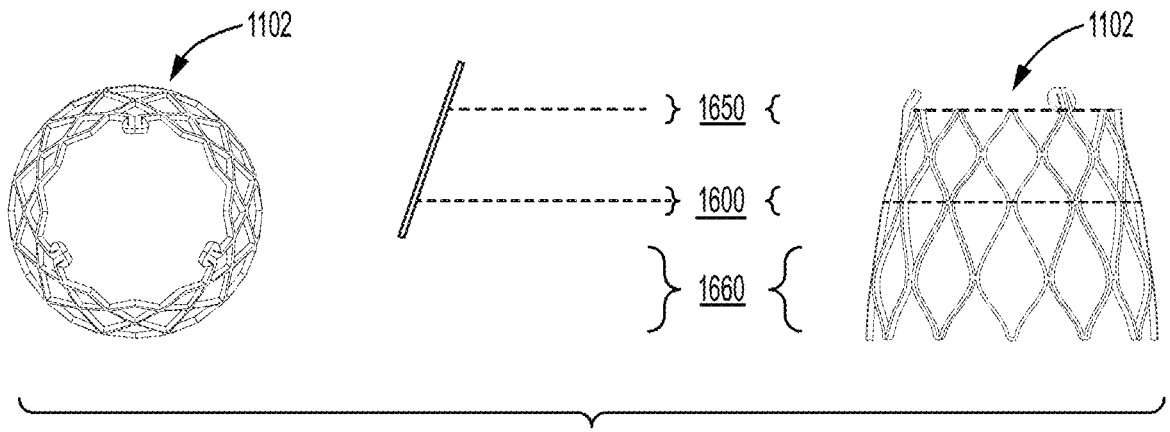
Figure 14B:
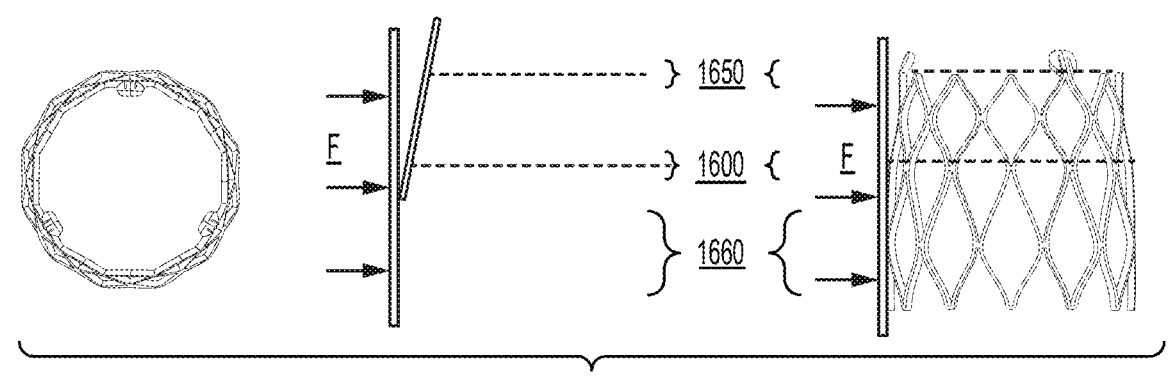
Figure 14C:
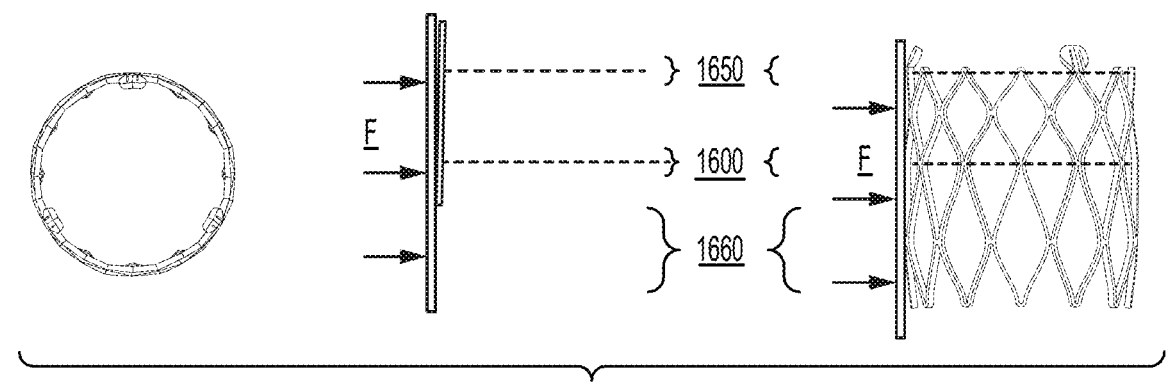

FIG. 14 shows a deformation model for the frame 1102 under an inward radial compressive load F. In general terms, the load is modeled as a compressive force applied in the form of a right cylinder applied equally around an entire circumference of the frame 1102 along the entire length of the frame 1102. FIG. 14A shows the frame 1102 in an unloaded condition. FIG. 14B shows the frame 1102 in a partially loaded condition under the inward radial compressive load F. FIG. 14C shows the frame 1102 under a fully loaded condition (e.g., as would be expected during operation following implantation). As shown, the commissure level diameter is closer in value to the leaflet base diameter after the prosthetic valve 100 is placed under full loading. FIGS. 15 and 16 help illustrate some advantages of this feature, for example when compared to a prosthetic valve with a frame that has the shape of a simple, right cylinder.

FIG. 15A shows an example of a prosthetic valve 2000 with a frame 2002 having the shape of a right cylinder, FIG. 15B shows deformation of that prosthetic valve 2000 when placed under a simulated load corresponding to a native valve orifice (e.g., with a majority placed on a proximal portion of the prosthetic valve 2000), and FIG. 15C shows the resulting performance of a leaflet construct 2004 of the prosthetic valve 2000 when placed under that inward radial compressive load. As shown, the leaflet construct 2004 shows wrinkling and less than optimal opening conditions as a result of the leaflet base diameter of the prosthetic valve 2000 being compressed inwardly a large amount so that it is relatively less than the commissure level diameter.

FIG. 16 shows expected performance of the prosthetic valve 100 under similar conditions to those described above with regard to the prosthetic valve 2000 of FIG. 15. FIG. 16A shows the model of the prosthetic valve 100 with the diametric taper previously described. FIG. 16B shows the modeled performance of the prosthetic valve 100 under the same simulated load as FIG. 15B. As shown in FIG. 16B, the model shows the prosthetic valve 100 to take on a much less tapered, cylindrical shape under a similar operational state. As shown in FIG. 16C, the model shows the prosthetic valve 100 to have a relatively wrinkle-free, optimal opening profile under the simulated inward radial compressive load. This enhanced operational performance may be attributed, at least in part, to the leaflet base diameter of the prosthetic valve 100 being compressed inwardly a lesser amount and the leaflet base diameter being relatively closer to the commissure level diameter when the prosthetic valve 100 is in the simulated, operational state.

FIGS. 17 and 18 provide further visualization of potential advantages achieved by the tapered diametric profiles described herein. FIG. 17 shows the prosthetic valve 2000 of FIG. 15 in a modeled aortic orifice. As shown, when subjected to the simulated forces encountered in the modeled aortic orifice, the prosthetic valve 2000 takes on an irregular diametric shape as shown in FIG. 17A and a relatively large proximal taper is imparted as shown in FIGS. 17B and 17C. In turn, FIG. 18 shows a modeled deformation of the prosthetic valve 100 when subjected to the simulated forces encountered in the same modeled aortic orifice. As shown, the prosthetic valve 100 has taken on a relatively regular, cylindrical shape with a reduced taper and a relatively circular diametric profile. It should be understood that this more regular, diametric profile is desirable for optimal valve performance, resulting in a more regular opening through the prosthetic valve 100 when transitioned to the open state.

FIG. 19 shows the frame 1102 of the prosthetic valve 100 (FIG. 1) with a constant diametric taper and commissure posts 1120 with modified features. In particular, the commissure post 1120 have been modified for attachment of leaflet construct 104 (not shown) to the frame 1102 by adhering and/or wrapping one or more portions of the leaflet construct to the commissure posts 1120, for example. As shown in FIG. 19, the commissure posts 1120 also have a rounded, atraumatic design.

FIG. 20 shows another possible modification for the frame 1102 of the prosthetic valve 100 (FIG. 1). As shown, one or more of the plurality of frame members 1122 may be modified with features for the frame 1102 usable for securing the constraints 1272 (FIG. 1) to the prosthetic valve 100. As shown in FIG. 20, one or more of the plurality of rows of frame members 1224 (e.g., the proximal row 1230 and/or the distal row 1232 shown in FIGS. 3 and 7) and/or one or more of the plurality of commissure posts 1120 (FIGS. 3 and 7) optionally includes a plurality of circumferentially-oriented eyelets 2024A. In some examples, the plurality of circumferentially-oriented eyelets 2024A are formed one or more of the plurality of rows of frame members (e.g., at one or more of the apices previously described). Again, these features can additionally or alternatively be located elsewhere in the frame design. Various methods are usable to form the plurality of circumferentially-oriented eyelets 2024A. For example, the plurality of circumferentially-oriented eyelets 2024A are optionally formed using a circumferential lasing process, a circumferential drilling process, a casting process, combinations thereof and other technique as desired.

FIGS. 21 and 22 are illustrative of formation of the plurality of circumferentially-oriented eyelets 2024A using a further technique and show formation of one of the plurality of circumferentially-oriented eyelets 2024A according to FIG. 20. For example, as shown, the plurality of circumferentially-oriented eyelets 2024A can optionally be formed by first forming a radially-oriented eyelet 2024R in a radial direction (FIG. 21) and then twisting the frame 1102 to re-orient the radially-oriented eyelet 2024R circumferentially to define one of the plurality of circumferentially-oriented eyelets 2024A (FIG. 22). This, twisted form may be heat set, set by cold working, or set by any of a variety of methods as desired depending upon application and material used.

FIG. 23 shows a plurality of radially-oriented eyelets 2024R formed in the commissure posts 1120. As shown, the radially-oriented eyelets 2024R have smoothed edges (e.g., via electro polishing). In some examples, the constraint 1272 (FIG. 1) is able to be woven through the radially-oriented eyelets to help provide guide for the constraint 1272 (FIG. 1) as it extends about the frame 1102. The radially-oriented eyelets 2024R are optionally formed via lasing, or other manufacturing option as desired. FIG. 23 also illustrates an additional, optional feature. In particular, the frame 1102 is shown with a plurality of atraumatic posts 2120 between the plurality of commissure posts 1120. The atraumatic posts 2120 are optionally employed to help protect the leaflet construct 104, and in particular portions that extend above the frame member distal boundary 1236 (FIG. 2). As shown, the atraumatic posts 2120 are relatively narrow, and fit well within the space between adjacent ones of the plurality of commissure posts 1120 to facilitate diametric compaction of the frame 1102.

Various advantages may be realized by securing one or more of the plurality of constraints 1272 using the circumferentially-oriented eyelets 2024A and/or the radially-oriented eyelets 2024R. For example, tension forces may be reduced via a reduction in friction forces (e.g., by reducing the amount of surface area contacted by a particular constraint). Moreover, surface profile may be reduced and reliability in deployment and compaction increased. Additionally or alternatively, either the circumferentially-oriented eyelets 2024A or the radially-oriented eyelets 2024R may be polished, or otherwise formed for reduced friction and may additionally or alternatively be treated with coatings or surface modifications to reduce friction.

Figure 25:
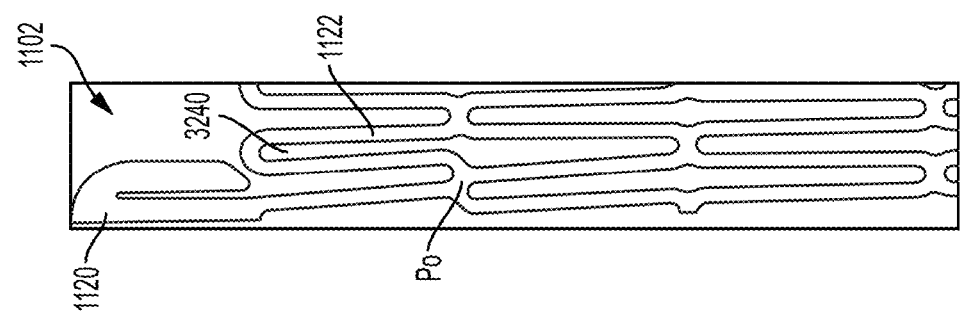
FIGS. 24 to 27 are illustrative of offset intersection locations on prosthetic valve frames, according to some embodiments.
Figure 24:
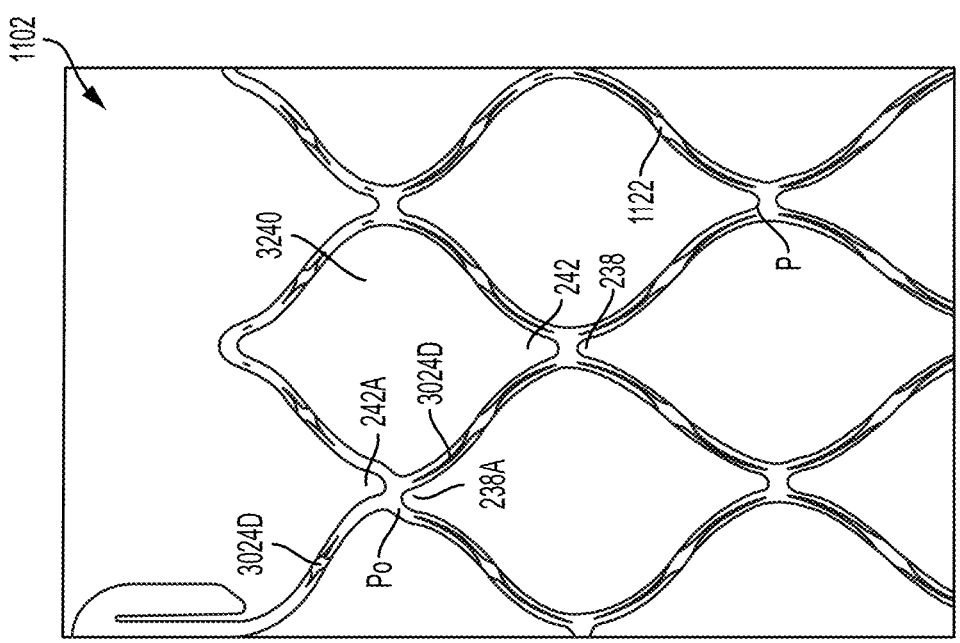
Figure 27:
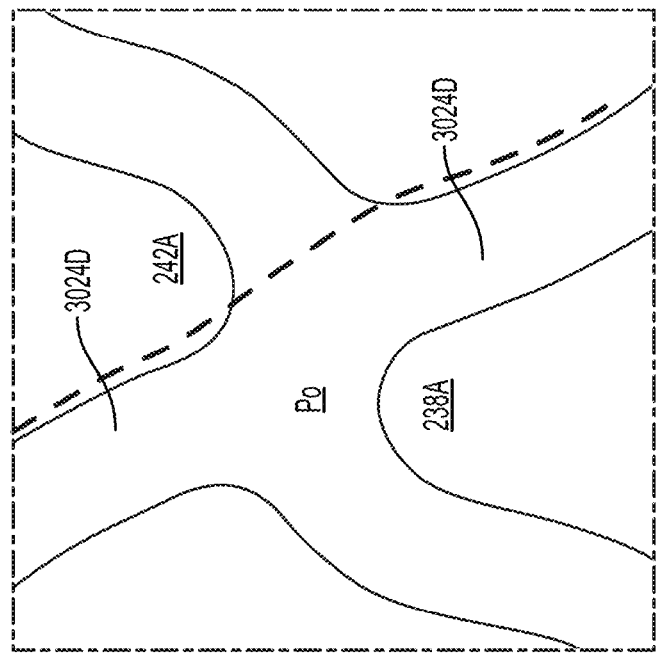

FIGS. 24 and 25 are illustrative of another possible feature for the frame 1102 of the prosthetic valve 100. As shown, a distal-facing apex 238A of one of the plurality of rows of distal-facing apices 238 defines an offset intersection location Po with a proximal-facing apex 242A of one of the plurality of proximal-facing apices 242. As shown, the offset intersection location Po is proximate one of the plurality of commissure posts 1120. The offset intersection location Po results in two diagonal frame members 3024D of the plurality of frame members 1122 defining a relatively straight line extending through the offset intersection location Po as illustrated by the relative comparison between FIG. 26 (not offset, intersection location P) and FIG. 27 (offset intersection location Po). As shown in FIG. 25, the offset intersection location Po results in a closed cell 3240 adjacent the commissure post 1120, and in particular the frame members 1122 defining the closed cell 3240, to fold laterally and also proximally to fit under the commissure post 1120 (e.g., to effect a more efficient packing profile as shown in FIG. 25) when the frame 1102 is diametrically compacted. Similar offset intersections Po are optionally employed next to each of the commissure posts 1120 of the frame 1102 as desired.

Figure 29:
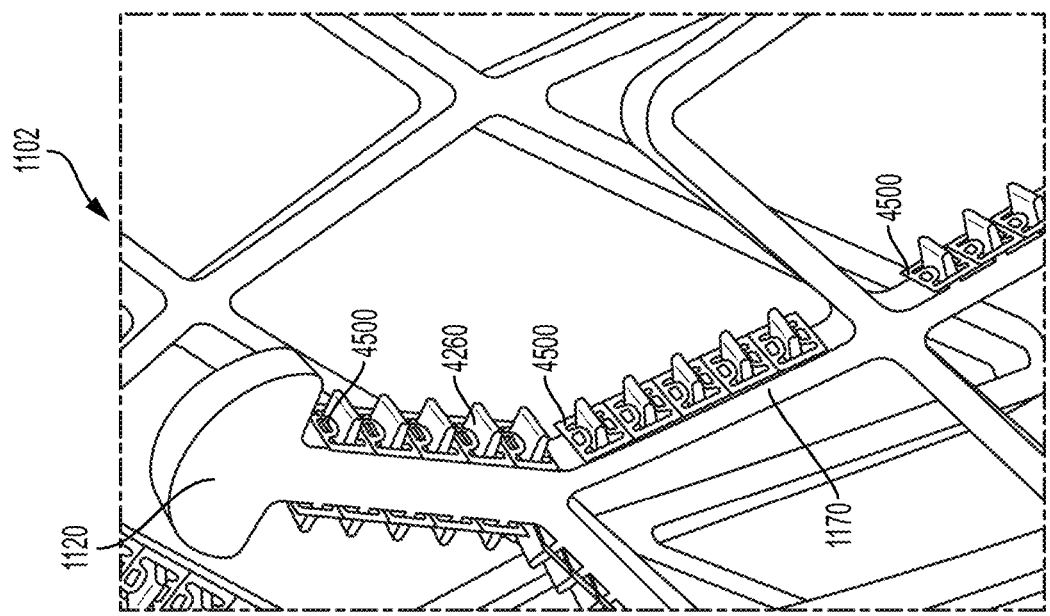
FIGS. 28 to 31 are illustrative of attachment features for prosthetic valves, according to some embodiments.
Figure 28:
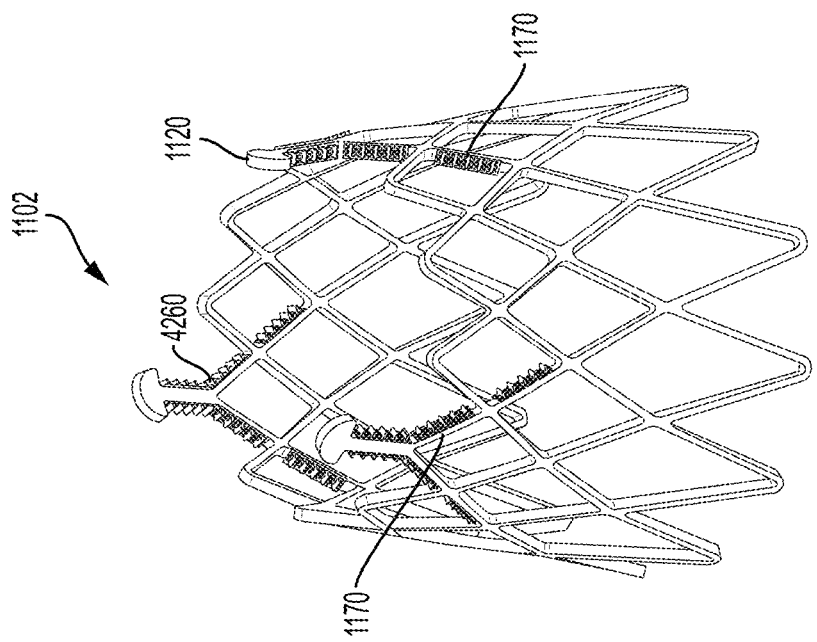

FIG. 28 shows another modification for the frame 1102 for attaching the leaflet construct (FIG. 1) to the frame 1102 and FIG. 29 is an enlarged view of a portion of FIG. 28. As shown in FIGS. 28 and 29, the frame 1102 is modified with a plurality of leaflet frame projections 4260 for securing the leaflet construct 104 to the frame 1102. As shown, the leaflet frame projections are disposed on the sides of the plurality of commissure posts 1120 as well as the leaflet attachment frame members 1170 (FIG. 11).

Figure 30:
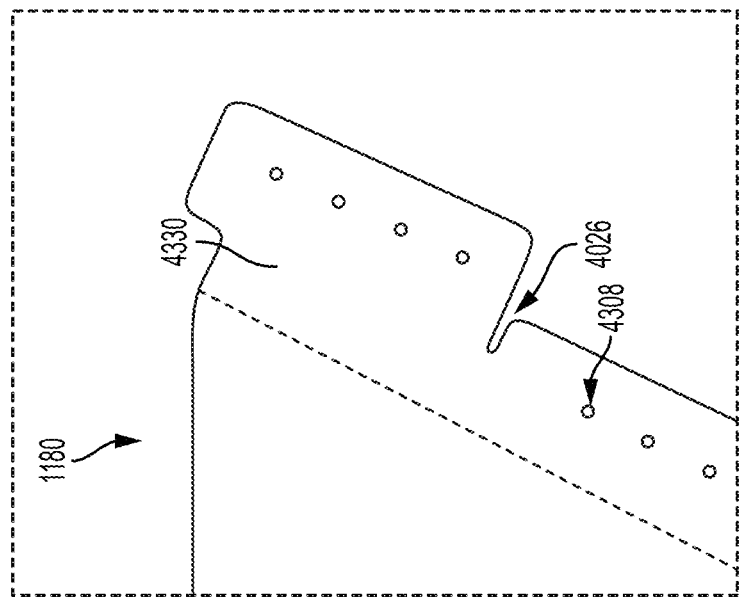

FIG. 30 shows a modification used for the plurality of leaflets 1180, where each leaflet generally includes a plurality of leaflet apertures 4308 disposed about a leaflet attachment region 4330 (e.g., corresponding generally to the locations of the commissure tab(s) and/or attachment tab(s) previously described. In use, the leaflet attachment region 4330 is folded over or otherwise wrapped and/or wound about a portion of the frame 1102 with the plurality of leaflet apertures 4308 received over the plurality of leaflet frame projections 4260.

Figure 31:
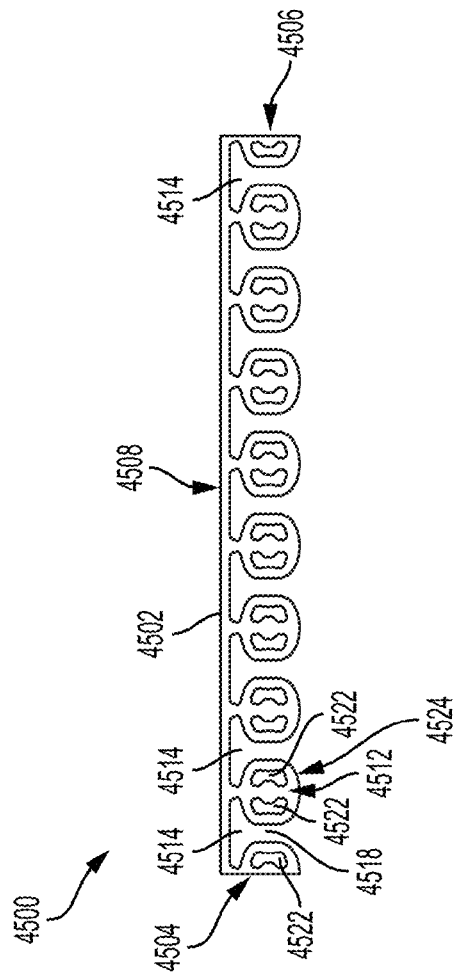

FIG. 31 is a top view of a leaflet retention feature 4500. The leaflet retention feature 4500 includes a plurality of struts 4512. As shown, the leaflet retention feature 4500 includes a body 4502, a first end 4504, a second end 4506 opposite the first end 4504 and a first side 4508 extending between the first and second ends 4504, 4506. The plurality of struts 4512 extend opposite from the first side 4508. As shown in FIG. 30, each of the plurality of struts 4512 include a free end 4524 that projects away from where the struts are coupled to the body 4502. The leaflet retention feature 4500 includes a plurality of cells 4514. As shown, a plurality of regions 4518 are defined between adjacently situated ones of the struts 4512, each if which is laterally exposed or not otherwise enclosed (e.g., in the instance the leaflet retention feature 4500 is secured to the leaflet frame projections 4260 by sliding the leaflet frame projections 4260 laterally through the plurality of regions 4518.

As shown in FIG. 29, each of the leaflet retention features 4500 is configured to be coupled onto (e.g., slidingly received onto) the leaflet frame projections 4260 such that the leaflet frame projections 4260 extend through gaps defined by cells 4514 between adjacent ones of the plurality of struts 4512. In different terms, the leaflet frame projections 4260 extend into the cells 4514 of the leaflet retention feature 4500. In various examples, the cells 4514 are narrower than the leaflet frame projections 4260, such that the leaflet retention feature 4500, and in particular the plurality of struts 4512, is configured to form an interference fit with the leaflet frame projections 4260 that are each received in one of the plurality of cells 4514.

In some examples, the leaflet attachment region 4330 (FIG. 30) is optionally placed onto, folded over, or wrapped and/or wound, about, or otherwise engaged with a portion of the frame 1102 including the leaflet frame projections 4260 with the plurality of leaflet apertures 4308 received over the plurality of leaflet frame projections 4260. The leaflet retention feature 4500 is advanced along the leaflet frame projections 4260 toward the surface from which the leaflet frame projections 4260 extends to form an interference fit that secures the leaflet attachment region 4330 to the frame. Generally, the leaflet retention feature 4500 is advanced until the leaflet retention feature 4500 contacts the leaflet 1180, and/or until the leaflet retention feature 4500 is advanced to a designated position to secure the leaflet retention feature 4500 over the leaflet 1180 to secure the leaflet 1180 to the frame 1102.

In some examples, the leaflet attachment region 4330 (whether wrapped about or otherwise engaged with the frame) is simply covered by the leaflet retention feature 4500 to secure the leaflet attachment region 4330 in place. Additionally or alternatively, as part of the attachment process, the leaflet attachment region 4330 is optionally placed over or under the leaflet retention feature 4500 and/or folded around the leaflet retention feature 4500 a desired number of times (e.g., such that the leaflet retention feature 4500 resides between one or more folds of the leaflet attachment region 4330). In some examples, the leaflet retention feature 4500 is bonded to the leaflet attachment region 4330 prior to, or after the leaflet retention feature 4500 is secured to the leaflet frame projections 4260.

It should also be understood that multiple leaflet retention features similar to the leaflet retention feature 4500 are secured over the leaflet frame projections 4260 around portions of the frame 1102 to which the leaflet construct 104 is secured, with a similar process being repeated for each of the plurality of leaflets 1180. Additionally, although the slots, and associated wrapping technique described in association with FIG. 12 is not shown, it should be understood that a combination of methods (e.g., wrapping through the first and second slots 1134, 1136 and/or using retaining elements such as the first and second retaining elements 1184, 1186) are optionally employed. Additional examples of suitable attachment methods similar to those described above can also be found in U.S. patent application Ser. No. 14/973,589, published as U.S. Pub. 2016/0175096, filed Dec. 17, 2015, entitled "PROSTHETIC VALVES WITH MECHANICALLY COUPLED LEAFLETS," filed by the Applicant hereof on even date herewith.

Figure 34:
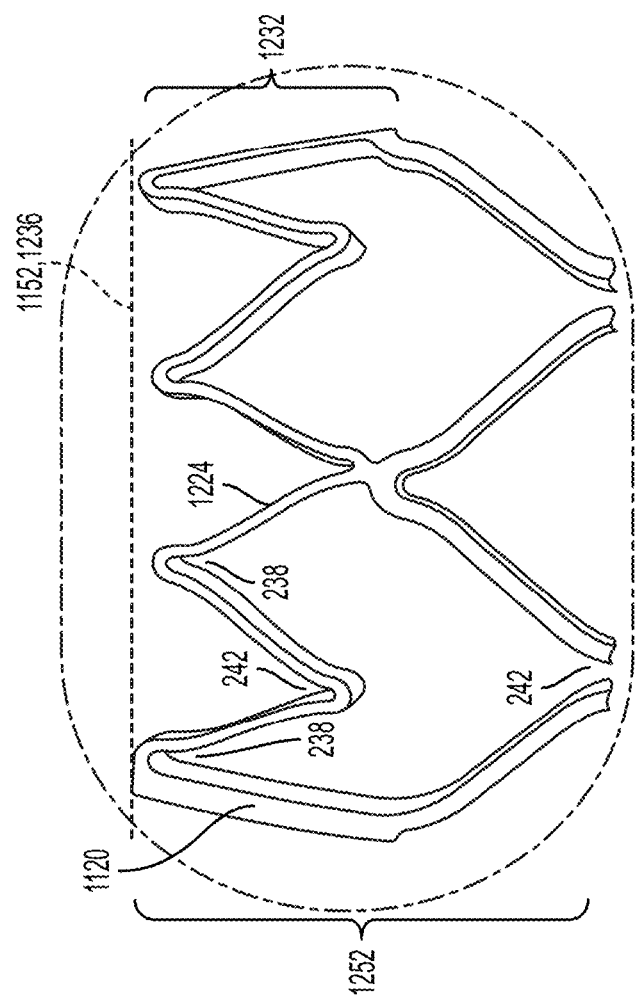
Figure 33:
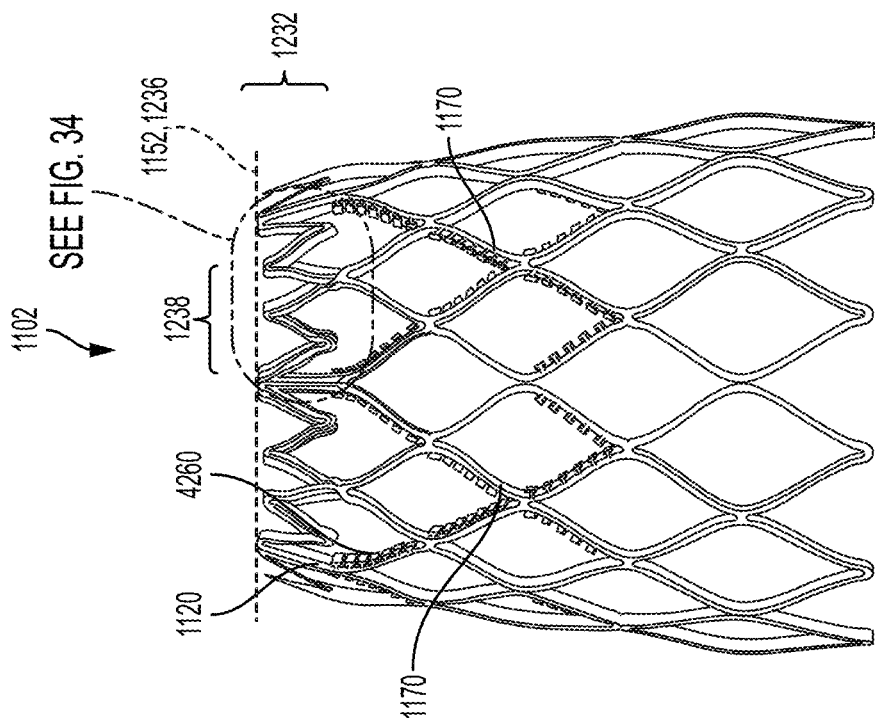

FIGS. 32 to 34 show variations of the frame 1102 in which the distal row 1232 of the plurality of rows of frame members 1224 extends distally to define the frame member distal boundary 1236 either proximate to, at the same level as, or distal to the commissure post distal boundary 1152. In these variations, the plurality of commissure posts 1120 do not extend beyond the frame member distal boundary 1236. In further variations (not shown), the plurality of commissure posts do not extend as far beyond the frame member distal boundary 1236 as other variations (e.g., FIG. 7). In various examples, the distal row 1232 provides additional support to the commissure posts 1120, and helps to reduce strain levels exhibited by flexing of the commissure posts 1120. This feature may improve overall reliability and performance by reducing stress/strain concentrations in the frame 1102 (e.g., maximum alternating strains).

In the examples of FIGS. 32 to 34, the attachment mechanism at the commissure posts 1120 can include T-shaped barbs or other retention features, such as the features shown in FIGS. 28 and 29 (leaflet frame projections 4260). Namely, the frame 1102 is modified with a plurality of leaflet frame projections for securing the leaflet construct 104 to the frame 1102. In the examples of FIGS. 32 to 34, leaflet frame projections are not shown on the sides of the plurality of commissure posts 1120 and the leaflet attachment frame members 1170 for ease of illustration and so that the features of the distal row 1232 of the plurality of rows of frame members 1224 may be more easily visualized.

According to the example shown in FIG. 32, the distal row 1232 of frame members 1224 projects distally beyond the commissure post distal boundary 1152 to define a frame member distal boundary 1236 that is also distal the commissure post distal boundary 1152.

The examples of FIGS. 32A to 32C utilize an alternative, inverted distal row approach to provide the additional structural support to the commissure posts 1120 while minimizing any increase in overall height of the frame 1102, and thus the prosthetic valve 100. For example, in FIG. 32A one or more closed cells (e.g., each closed cell) of the distal row of closed cells 1252 has two distal-facing apices 238, as does the example of FIG. 32B. In the example of FIG. 32C, one or more closed cells (e.g., each closed cell) of the distal row of closed cells 1252 has three distal-facing apices 238. These reversed, or inverted apex configurations facilitate enhanced rigidity at the distal row 1232, and assist with reinforcing the commissure posts 1120 against stress/strain due to leaflet pressurization.

FIGS. 33 and 34 show a similar arrangement to that of FIG. 32*b*, with offset intersections to assist with packing density of the frame and/or manufacturing considerations. In any of the foregoing examples, the distal row 1232 of the plurality of rows of frame members 1224 may include relatively thinner frame members 1224 (see, e.g., FIG. 34), which may assist with compacting the frame 1102 into a diametrically smaller delivery configuration while still achieving the reinforcing characteristic for the commissure posts 1120. From the foregoing, it should be understood that the inverted, or reverse distal row 1232 configurations may be applied to any of the examples of the frame 1102 shown and/or described.

Figure 35:
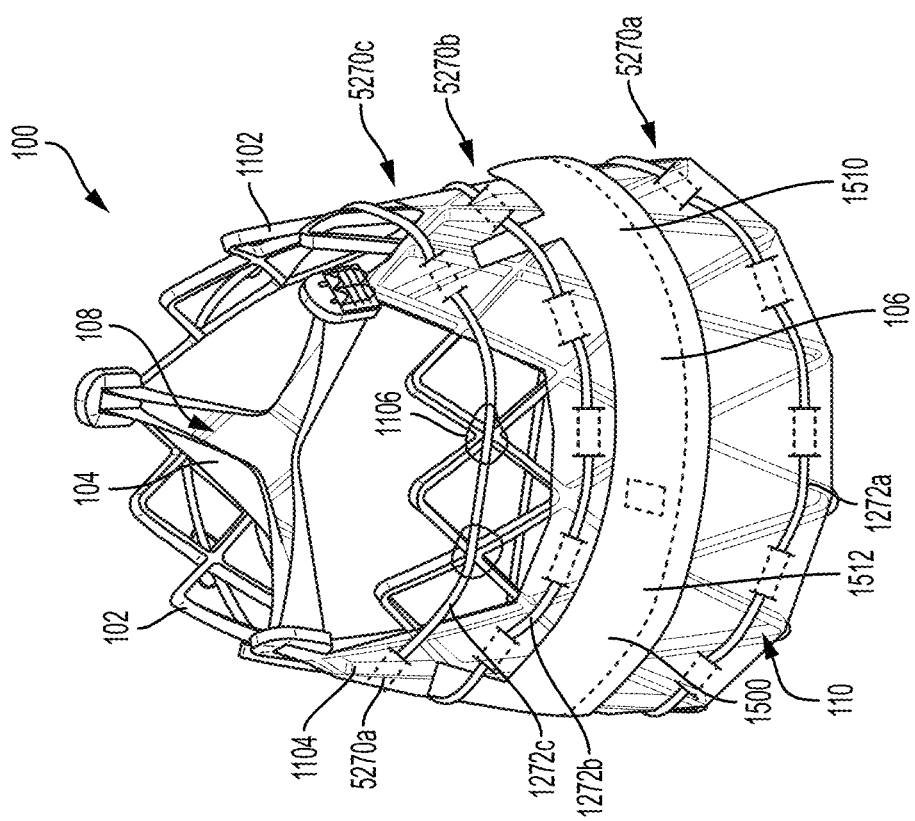

FIGS. 35 and 36 illustrate constraint retention features for the prosthetic valve 100 that can be provided in addition to or as an alternative to the rows of apertures 1270 and constraint retainers 1106, according to some examples. For example, as shown in FIG. 35, the prosthetic valve 100 optionally includes a plurality of constraint guides 5270, which may operate similarly to the constraint retainers 1106 to receive constraints 1272 for prosthetic valve 100 delivery and deployment. It should also be understood that any combination of constraint retention features is employed as desired and, as shown in FIG. 35, the prosthetic valve 100 also optionally includes one or more constraint retainers 1106 formed as loops of material coupled to the support structure 102 (e.g., secured to one or more of the plurality of frame members 1122) as previously described.

Like the constraint retainers 1106, the constraint guides 5270 help retain and guide one or more of the constraints 1272 to pass around the prosthetic valve 100 and not disengage or slip off (e.g., they are able to move axially, but are generally restrained in a longitudinal direction of the prosthetic valve 16). The constraint guides 5270 can be described as tunnels, external bands, or belt loops, through which the constraints 1272 are able to be slidably or otherwise received. As shown, the constraint guides 5270 are formed by bands or layers of material that define spaces, gaps, or tunnels between layers of material (e.g., between layers of the cover 1104). The constraints 1272 pass through these gaps and are retained between the layers of material. This type of arrangement can be contrasted to those in which constraint 1272 is threaded in-and-out of the rows of apertures 1270, from the interior to the exterior of the prosthetic valve 100. In different terms, as shown in FIG. 35 the constraint guides 5270 do not result in the constraint 1272 passing behind the cover 1104 into the interior of the prosthetic valve 100.

Generally, the approach implemented by the constraint guides 5270 is to embed, or retain the constraint 1272 within portions of the cover 1104, rather than having the constraint 1272 simply wrapped around the periphery of the prosthetic valve 100 or laced through an interior and exterior path of the prosthetic valve 100 through the rows of aperture 1270.

The constraint guides 5270 can provide a variety of desirable features, including one of more of the following: reduced perivalvular leakage due to elimination of biopsies (e.g., openings or apertures) through the cover 1104 of prosthetic valve 100 (e.g., in contrast to some examples using the apertures 1270); improved durability of the prosthetic valve 100 due to less perforations; improved deployment reliability (e.g., release and/or tensioning of the constraint 1272) due to reduced friction between constraint 1272 and the prosthetic valve 100; improved prosthetic valve 100 compatibility and reliability due to reduction of interference/interaction of vessel walls with the constraint 1272; reduced likelihood of snagging/pinching the constraint 1272 as the constraint 1272 is not captured or otherwise trapped between portions of the frame 1102 (e.g., as can happen when the constraint 1272 is threaded in-and-out of the apertures 1270 and/or the frame 1102); and improved durability of the constraint 1272, due to less wear from the frame 1102 engaging the constraint 1272 (e.g., pinching the constraint 1272) when the prosthetic valve 100 is compressed, or diametrically compacted. These are just a few examples of optional advantages according to various embodiments.

Generally, the constraint guides 5270 receive (e.g., slidingly) one or more constraints 1272 that pass into and out of the constraint guides 5270 in a circumferential path extending around the frame 1102. The one or more constraints 1272 are thus able to be used for retaining the frame 1102, and thus the prosthetic valve 100, in a diametrically compacted, delivery configuration and then permitting the prosthetic valve 100 to be transitioned to a diametrically enlarged, deployed configuration upon releasing tension in the one or more constraints 1272 using an associated delivery system (such as those previously or subsequently described).

As shown in FIG. 35, the prosthetic valve 100 includes a plurality of rows of the constraint guides 5270, such as a proximal row of constraint guides 5270a, one or more intermediate rows of constraint guides 5270b, and a distal row of constraint guides 5270c. Each of the rows of constraint guides 5270 is positioned as desired for a corresponding constraint 1272 to form a loop at a desired level along the prosthetic valve 100. For example, the cover 1104 optionally includes a plurality of separate constraint guides 5270 each spaced circumferentially apart from one another about the circumference of the frame 1102 in a row, with one of the constraints 1272 passing through each of the plurality of constraint guides 5270 in a circumferentially-aligned row. Although, in some examples, each of a plurality of separate constraint guides 5270 in a row is circumferentially-aligned about the circumference of the frame 1102, in other examples a row is not circumferentially-aligned, but instead is helically aligned, or defines another path about the circumference of the frame 1102 as desired.

Generally, the proximal row of constraint guides 5270a slidably receive a proximal constraint 1272a that is passed through the proximal row of constraint guides 5270a and which can be tensioned to collapse, or radially compress, the prosthetic valve 100 onto a delivery catheter as previously described. Similarly, the intermediate row of constraint guides 5270b and the distal row of constraint guides 5270c each slidably receive an intermediate constraint 1272b and a distal constraint 1272c, respectively, that are each is passed through the constraint guides 5270 and which can be tensioned to collapse, or radially compress, the prosthetic valve 100. As shown, the proximal constraint 1272a is optionally passed through constraint retainers 1106 associated with the frame 1102, for example. For reference, a single row (whether circumferential and parallel, helical, or otherwise) may include multiple constraint guide designs, such as designs consistent with constraint guide 5270, constraint retainer 1106, or apertures 1270.

Figure 36A:
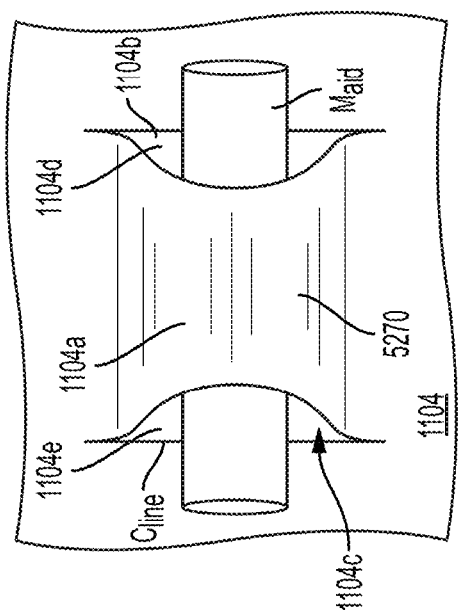
FIGS. 35 to 36C are illustrative of constraint guide features for prosthetic valves, according to some embodiments.

FIG. 36A is an enlarged view of a portion of the prosthetic valve 100 including one of the constraint guides 5270. As shown in FIG. 36A, a manufacturing aid Maid is inserted through the constraint guide 5270. Each of the constraint guides 5270 is optionally formed similarly to the constraint guide 5270 shown in FIG. 36A. As shown in FIG. 36A, the constraint guide 5270 includes an outer layer 1104a of material and base layer 1104b of material that combine to form a loop and define a tunnel 1104c, or gap, extending between the outer layer 1104a and the base layer 1104b within a thickness of the cover 1104. The tunnel 1104c extends between a first opening 1104d and a second opening 1104e in the outer surface of the cover 1104.

As described below, the outer layer 1104a and the base layer 1104b are optionally formed as layers of the cover 1104, where some methods of forming the constraint guides 5270 include making cut lines Cline through the outer layer 1104a on either side of the tunnel 1104c. In other embodiments, the outer layer 1104a is formed as a discrete flap, or piece of material that is subsequently secured to the cover 1104 to define the tunnel 1104c, as well as a portion of the outer surface of the cover 1104.

With additional reference to FIG. 35, the frame 1102 generally defines a circumference extending along a transverse path around the central longitudinal axis Xf of the frame 1102. As previously referenced, the cover 1104 is coupled to the frame 1102 and includes a plurality of constraint guides 5270. In some examples, each constraint guide 5270 defines a tunnel 1104c, such as that shown in FIG. 36A, that extends transversely to the central longitudinal axis Xf of the frame 1102 between the first opening 1104d and second opening 1104e in the outer surface of the cover 1104.

Figure 36B:
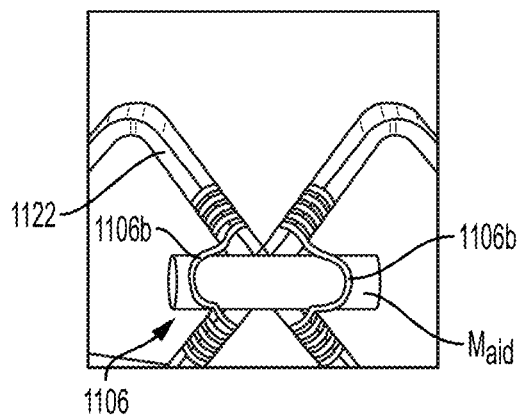

FIG. 36B illustrates two of the constraint retainers 1106 which have been formed by wrapping filaments around the frame members 1122 a plurality of times to secure the filaments to the frame members 1122 and to form one or more loops 1106b suitable for receiving one of the constraints 1272. As previously described, the filaments of the constraint retainers 1106 can be metallic (e.g., nitinol) polymeric (e.g., ePTFE) or any other biocompatible material. In some examples, the filaments are formed of biocompatible, biocorrodible/biodegradable material such that the filaments degrade and are absorbed or pass out of the body after a desired time frame. If desired, the constraint retainers 1106 can also be bonded (e.g., in addition or as an alternative to the wrapping securement mechanism) to specific points on the frame members 1122 using a suitable adhesive or other bonding agent, for example.

Figure 26:
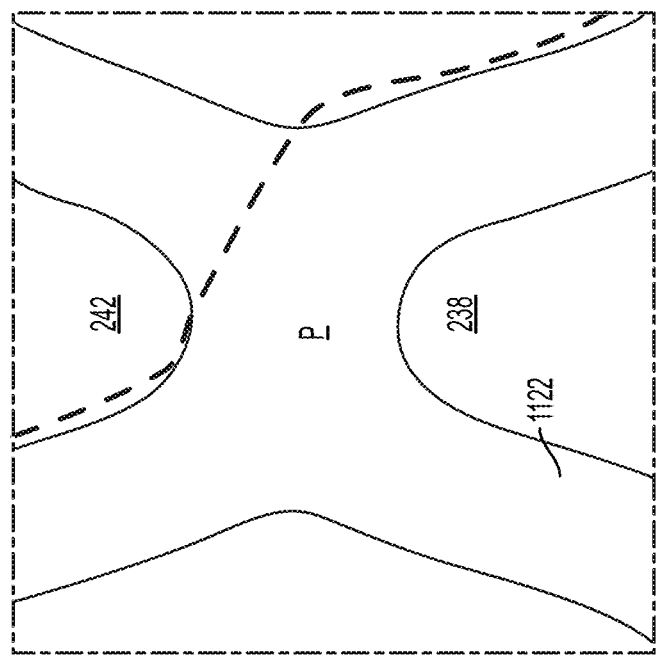
Figure 36C:
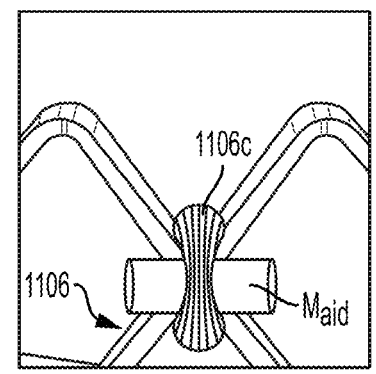

FIG. 36C illustrates a constraint retainer 1106 formed by wrapping a filament around an intersection location of the frame members 1122, such as the intersection location P (FIG. 26). The constraint retainer 1106 is formed by wrapping a filament around the frame members 1122 at the intersection P one or more times to secure the filament to the frame members 1122 and to form one or more loops 1106c suitable for receiving one of the constraints 1272. As previously described, the filaments of the constraint retainer 1106 can be metallic (e.g., nitinol) polymeric (e.g., ePTFE)

or other material. In some examples, the filaments are formed of biocompatible, biocorrodible/biodegradable material such that the filaments degrade and are absorbed or pass out of the body after a desired time frame. If desired, the constraint retainers 1106 can be wrapped and bonded to specific points on the frame members 1122 (e.g., in addition or as an alternative to the wrapping securement mechanism) using a suitable adhesive or other bonding agent, for example.

Some methods of forming the prosthetic valve 100 with constraint guides 5270 include one or more of the following steps:

Applying one or more layers of inner cover material to form the base layer 1104b onto a mandrel, where the inner cover material includes an outwardly-facing adhesive;

Positioning the frame 1102 over the base layer 1104b;

Preparing one or more layers of outer cover material to form the outer layer 1104a, where the outer cover material optionally includes an inwardly facing adhesive;

Cutting the outer layer 1104a along the cut lines Cline on either side of the tunnel 1104c that will be formed at locations corresponding to each constraint guide 5270;

Positioning the outer layer 1104a over the frame 1102, the base layer 1104b and the outer layer 1104a combining to form the cover 1104, where the cut lines Cline, or holes through the outer layer 1104a are positioned at the desired locations for the constraint guides 5270;

Obtaining a manufacturing aid Maid for placement through each of the tunnels 1104c (i.e., through the cut lines Cline on either side of the tunnels 1104c), where the manufacturing aid Maid should have a desired diameter to achieve an appropriate level of interference of the constraint 1272 with the constraint guide 5270 upon removal of the manufacturing aid Maid, may have a length corresponding to that of individual tunnels 1104c or be longer, continuous element for placement through multiple tunnels 1104c, should be able to withstand bonding temperatures of the base layer 1104b and the outer layer 1104a, and should not bond to the base layer 1104b and/or outer layer 1104a, or should otherwise be configured such that the manufacturing aid Maid is able to be effectively removed from the tunnel 1104c (e.g., a potential manufacturing aid Maid may be a PEEK rod);

Threading the manufacturing aid Maid through the tunnels 1104c between the base layer 1104b and the outer layer 1104a;

Preparing the frame 1102, base layer 1104b, outer layer 1104a, and manufacturing aid $M_{aid}$ for bonding and bonding one or more of the foregoing (e.g., by overwrapping with a sacrificial compression layer and heating in an oven to reflow the adhesive(s) and/or sinter layer(s)); and Removing the manufacturing aid $M_{aid}$ from the tunnel 1104c. In some examples, the manufacturing aid $M_{aid}$ may be loosened or freed from the tunnel 1104c by using a slender rod (or needle) to trace the outer diameter of the manufacturing aid $M_{aid}$ to break the manufacturing aid $M_{aid}$ free from the base layer 1104b and/or outer layer 1104a prior to pulling the manufacturing aid $M_{aid}$ out of the tunnel 1104c (e.g., with a tweezers). Generally, the same process may be used to form any number of the tunnels 1104c as desired.

In some examples, a method of forming a prosthetic valve with the constraint retainers 1106 includes the following steps:

Obtaining a manufacturing aid $M_{aid}$ for placement through each of the loops 1106B or 1106C, where the manufacturing aid $M_{aid}$ should have a desired diameter to achieve an appropriate level of interference of the constraint 1272 with the constraint retainer 1106 upon removal of the manufacturing aid $M_{aid}$, should be able to withstand bonding temperatures for any bonding agent used with the filament forming the loops 1106b or 1106c, and should not bond to the material forming the loops 1106b or 1106c, or should otherwise be configured such that the manufacturing aid $M_{aid}$ is able to be effectively removed from the loops 1106b or 1106c (e.g., a potential manufacturing aid $M_{aid}$ may be a PEEK rod);

Wrapping a filament around the frame members 1122 one or more times to secure the filament to the frame members 1122 and to form the loop 1106B or 1106C over the manufacturing aid $M_{aid}$;

Preparing the frame 1102, filament, and manufacturing aid $M_{aid}$ for optional bonding (e.g., by heating in an oven to reflow the adhesive(s) and/or sinter filament winding(s); and Removing the manufacturing aid $M_{aid}$ from the loop 1106b or 1106c. In some examples, the manufacturing aid $M_{aid}$ may be loosened or freed from the loops 1106b or 1106c by using a slender rod (or needle) to trace the outer diameters of the manufacturing aid $M_{aid}$ to break the manufacturing aid $M_{aid}$ free from the filament prior to pulling the manufacturing aid $M_{aid}$ out of the loops 1106b or 1106c (e.g., with a tweezers). Generally, the same process may be used to form any number of the loops 1106b or 1106c as desired.

Figure 37:
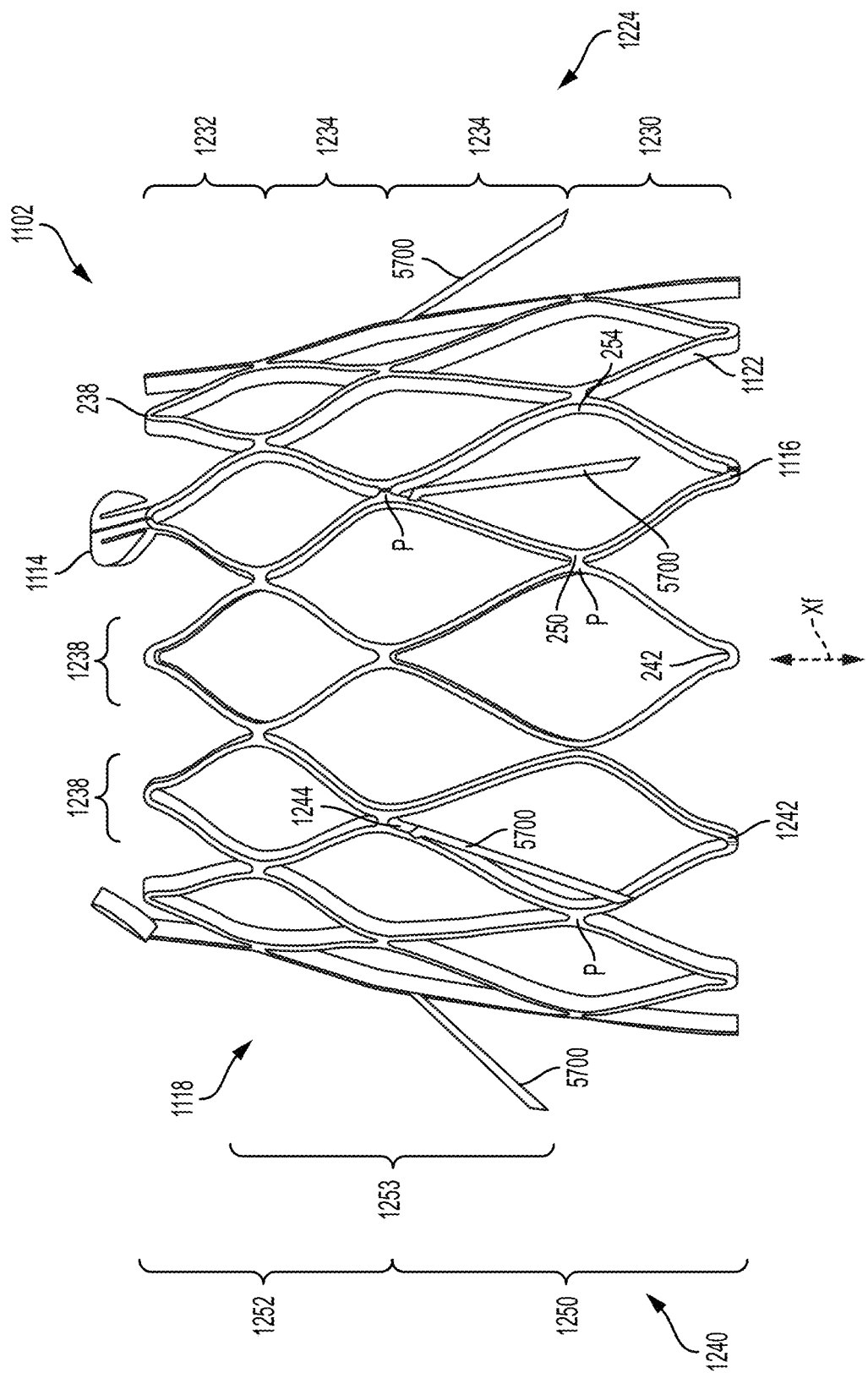
FIGS. 37 to 40 are illustrative of anchor member features for prosthetic valves, according to some embodiments.

FIG. 37 shows additional, optional anchor member features of the frame 1102 of the prosthetic valve 100. As shown, the frame 1102 includes a plurality of anchor members 5700 that project radially outward from the frame 1102. In some examples, the plurality of anchor members 5700 are formed of the same material as the frame 1102 (e.g., by laser cutting the anchors from the same material as the remainder of the frame 1102).

Each of the anchor members 5700 is optionally biased (e.g., by shape memory) to extend radially outward, and thus to be radially actuable, to a desired angle from the frame (e.g., at an angle of greater than 15 degrees, 20 degrees, 45 degrees, or more) relative to the central longitudinal axis Xf of the frame 1102. Any number of anchor members 5700 is contemplated at any of a variety of positions on the frame 1102. As shown in the example of FIG. 37, one of the anchor members 5700 extends from a location on one of the frame members 1122 that is proximate to every other distal-facing apice 238 of the proximal row of closed cells 1250.

Figure 38:
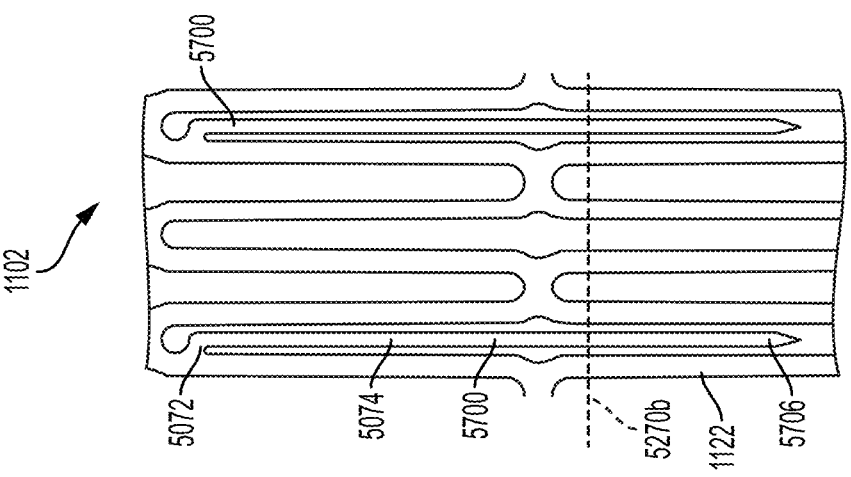

FIG. 38 shows an example of a possible compacted frame design for the frame 1102 including the anchor members 5700. As shown in FIG. 38, each of the anchor members 5700 includes a base 5702 where each of the anchor members 5700 extends from the frame 1102, a body 5704 that projects radially outward from the frame 1102 upon deployment of the prosthetic valve 100, and a tip 5706 that may be configured to penetration tissue. In various examples, the position for the intermediate constraint 1272b corresponds to a location that would extend across the anchor members 5700 when the frame 1102, and the prosthetic valve 100 more generally, is in the diametrically compacted state. In this manner, the intermediate constraint 1272b is optionally used to constrain the anchor members 5700 until the intermediate constraint 1272b is released. Additionally, as shown, the anchor members 5700 are optionally configured to be interleaved in the spaces between adjacent frame members 1122 to facilitate a more compact design.

In some examples, the anchor members 5700 are located to engage the base of the native leaflets and the native sinuses of a native valve. The anchor members 5700 may also be located at a position on the prosthetic valve 100 to displace or puncture native leaflets and reside in the native sinuses of a native valve structure. Finally, the anchor members 5700 are generally positioned and configured not to interfere with leaflet operation of the prosthetic valve 100 or other operational valve features according to various designs.

Figure 39:
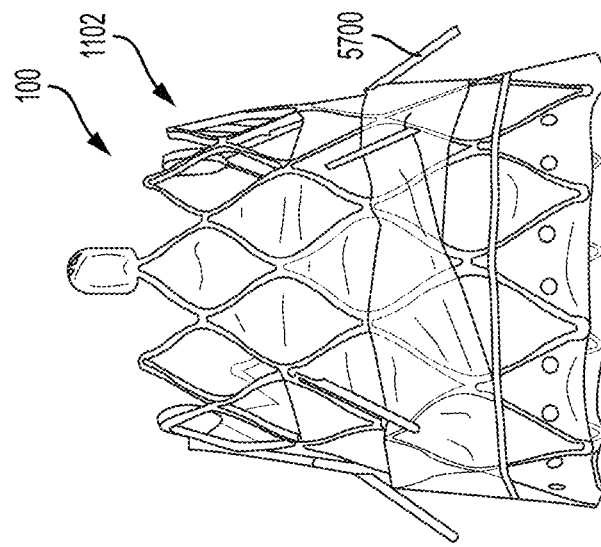

FIG. 39 is an example of the assembled prosthetic valve 100 with the anchor members 5700. As shown, the anchor members 5700 are free from the cover 1104 and are free to project outwardly and to radially actuate upon expansion of the prosthetic valve 100 from a diametrically compacted state (e.g., FIG. 38) to the diametrically expanded, delivery state shown in FIG. 39. For reference, the design of the frame 1102 in FIG. 39 includes an extra row of closed cells (e.g., in comparison to the examples for the frame 1102 shown in FIGS. 37 and 19).

Figure 40:
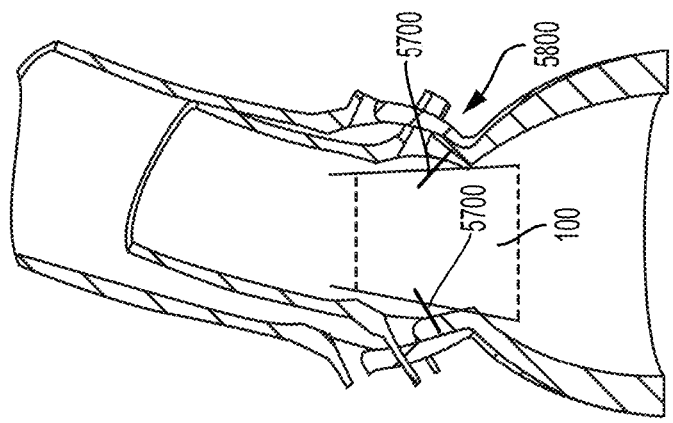

The anchor members 5700 are optionally positioned at locations on the prosthetic valve 100 that correspond to a desirable anchoring site in the anatomy. As shown schematically in FIG. 40, upon deployment, the anchor members 5700 are optionally employed to help anchor or retain the prosthetic valve 100 at a location in the anatomy of a patient, including a valve orifice 5800, such as a human or porcine native valve orifice (e.g., aortic valve orifice or a mitral valve orifice). Although the anchor members 5700 are shown in an intermediate position on the prosthetic valve 100, alternative or additional locations for the anchor members 5700 (e.g., more proximally- or distally-located positions on the frame 1102 of the prosthetic valve 100) are contemplated.

In some associated methods of treatment, the anchor members 5700 assist with securing the prosthetic valve 100 in a native valve orifice that is exhibiting valve insufficiency (e.g., aortic or mitral valve insufficiency, for example). Valve insufficiency and associated regurgitation through the valve may be a result of weakened tissue associated with the valve. In such instances, the anchor members 5700 may be particularly useful for securing the prosthetic valve 100 in place. Some methods of treatment of valve insufficiency include positioning the prosthetic valve 100 at a desired treatment location within the body and securing the prosthetic valve 100 at the desired treatment location, including expanding the prosthetic valve at the desired treatment location such that the anchor members 5700 of the prosthetic valve 100 anchor the prosthetic valve 100 at the desired treatment location.

In some examples, the desired treatment location can be a native aortic valve exhibiting aortic regurgitation and the method can include positioning the prosthetic valve at the native valve orifice and securing the prosthetic valve at the native valve orifice by engaging the anchor members 5700 with tissue associated with the native aortic valve. Positioning the prosthetic valve at the desired treatment location within the body can include constraining the prosthetic valve 100 in a diametrically compacted delivery profile with one or more of the constraints 1272 and positioning the prosthetic valve 100 at the desired treatment location within the body with the prosthetic valve 100 in the diametrically compacted delivery profile. The method can include radially actuating the anchor members 5700 by releasing one or more of the constraints 1272 and expanding the prosthetic valve 100 in the native valve orifice by releasing the one or more constraints 1272 such that the anchor members 5700 engage the tissue associated with the native aortic valve. Similarly to various embodiments, an inward radial compressive load may be applied to the prosthetic valve by the native valve orifice or associated tissue and the diametric taper exhibited by the prosthetic valve 100 may be reduced relative to when the prosthetic valve 100 is in an unloaded state.

Prosthetic valve leaflets detaching from a support structure, or frame, constitute a high risk to a patient into which it is placed. One factor contributing to leaflet detachment can be peak stress in the leaflet at the commissure region when the prosthetic valve is closed and under fluid backpressure. FIGS. 41 and 42 show a commissure attachment region variation and associated leaflet closing profile at the outflow end that can be employed in any of the embodiments and examples previously described. Adjacent, diverging leaflet attachment regions, may provide beneficial overall stress profiles in the leaflet adjacent the commissure regions of the leaflets.

As shown in FIG. 41, the commissure attachment regions 1134a, 1136a (which correspond to a modified version of the slots 1134a, 1136a of FIG. 5) of commissure post 1120a are modified to provide means by which to preserve, if not shorten, prosthetic valve height with the capability of reducing the peak commissure stress in the leaflet at the commissure post without altering the leaflet material properties.

FIG. 42 is illustrative of the leaflets 1180 of prosthetic valve 100 in a closed state with the diverging commissure attachment region modification. As shown, and as will be subsequently described, the diverging commissure attachment regions result in a closed profile with the leaflets 1180 having diverging free edges at the frame 1102.

As shown in FIG. 41, the upper most portion of adjacent commissure attachment regions near the second ends 1142a, 1146a have been modified from being non-divergent (e.g., parallel as shown in FIG. 5) to being divergent. The adjacent commissure attachment regions of the commissure post 1120a terminates by extending away from a middle axis Yf positioned centrally between each of the adjacent commissure attachment regions 1134a, 1136a, the pair diverging from a location below the commissure post tip (the distal end 1150a) in the outflow direction. The adjacent commissure attachment regions 1134a, 1136a may diverge along their entire heights, or as shown may have base portions toward the first ends 1140a, 1144a that are parallel or otherwise non-diverging and terminal portions toward the second ends 1142a, 1146a that are diverging as shown. Each of the commissure posts 1120 may be similarly configured, resulting in a diverging leaflet profile as illustrated generally in FIG. 42.

Figure 43:
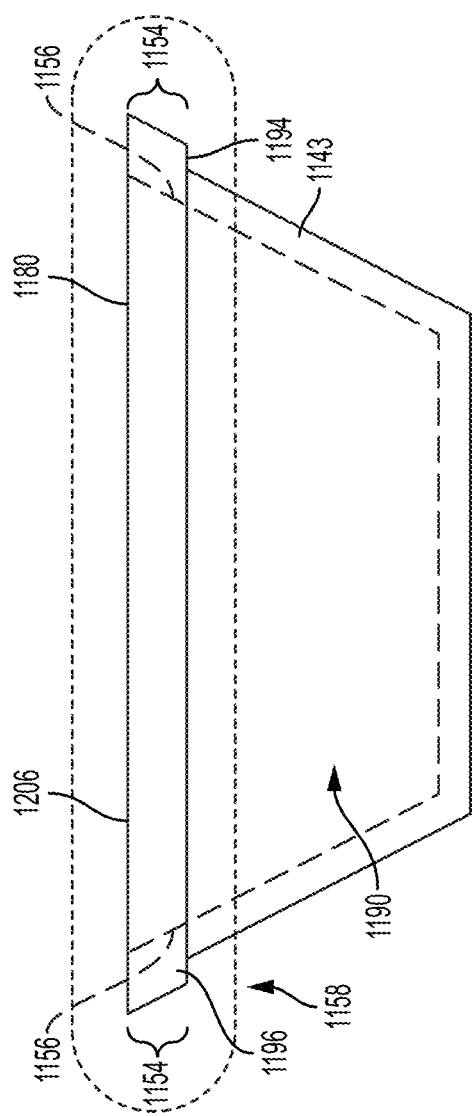

FIG. 43 is a schematic view of one of the plurality of leaflets 1180 which can be referenced for further discussion of leaflet effects achieved using the diverging free-edge concept. As shown in the example of FIG. 43, the leaflet 1180 has body portion 1190 (also described as a cusp), free edge 1206, and commissure regions 1154. The free edge 1206 extends to two termini 1156. The two termini 1156 are defined at an intersection of the leaflet free edge 1206 and the leaflet attachment region 1143. The leaflet attachment regions 1143 of adjacent leaflets 1180 are configured to be coupled to the commissure posts 1120 at locations on the adjacent leaflets 1180 that are adjacent the termini 1156 of the adjacent leaflets 1180. According to some examples (e.g., FIG. 11), the leaflet attachment region 1143 is at the outer margin of the leaflet 1180 and corresponds to the plurality of attachment tabs 1192a, the first commissure tab 1194a, and the second commissure tab 1196a, where the first and second commissure tabs 1194a, 1196a correspond to the portion of the leaflet attachment region 1143 coupled to the commissure post 1120. In other examples (e.g., FIG. 30), the leaflet attachment regions 4330 corresponds to the correspond to the portion of the leaflet attachment region 1143 coupled to the commissure post 1120. In those other examples, the diverging commissure post slots 1134, 1136 are substituted with diverging leaflet frame projections 4260 for securing the leaflet construct 104 to the frame 1102 as previously described.

As illustrated schematically in FIG. 43, a (dashed) fold line defines an outer margin of the body portion 1190 and commissure regions 1154 used to secure the leaflet 1180 to the frame 1102. A free edge region 1158 is that location of the leaflet 1180 including and adjacent to the leaflet free edge 1206. The outer margin or leaflet attachment region 1143 of each leaflet 1180 is coupled to the frame 1102, and the free edge 1206 of the leaflet 1180 extends across a cylindrical region defined by the frame 1102.

In various examples, the commissure regions 1154 of adjacent ones of the leaflets 1180 are operable to pass through the adjacent commissure attachment regions 1134, 1136 (slots) in a side-by-side relationship (or be attached to diverging leaflet frame projections 4260 in a side-by-side relationship as previously referenced). Because the commissure post 1120 defines diverging commissure attachment regions 1134, 1136 that diverge in the outflow direction towards the commissure post tip the commissure regions 1134, 1136 of adjacent, respective leaflets 1180 will also diverge from a location away from the commissure post tip in the outflow direction when adjacent leaflets 1180 are in a closed, coapted position.

Non-diverging commissure attachment regions (e.g., FIG. 5) may have a maximal stress at the region corresponding to the terminus 1156 when a leaflet is in the closed position. It turn, use of diverging commissure attachment regions (e.g., as shown in FIG. 41), may help translate the region of maximal stress away from the termini 1156 of adjacent leaflets 1180, to be distributed over a larger area, and to also have a reduced magnitude. For example, stress force vectors within the leaflets 1180 along diverging regions proximate the termini 1156 may be reduced relative to the same basic frame and leaflet arrangement but with non-diverging commissure attachment regions by a reduction of 41% of peak stress in the leaflets 1180 in the free edges 1206 at the termini 1156 for a given frame length. The stress within the leaflets 1180 along the diverging region (e.g., in the free edges 1206 at the termini 1156) may be reduced more than 40% relative to a non-diverging attachment when exposed to peak closing pressures of about 135 mm Hg on the outflow faces (or distal faces) of the leaflets fora given frame length. It has been demonstrated that the location of maximum loaded stress can be moved to a predetermined and more favorable location and the magnitude and distribution of stress that a given region of the leaflet 1180 experiences can be changed by changing the geometry where the leaflets 1180 attach to the frame 1102, and in particular by using diverging attachment regions for adjacent leaflets. Similar results are expected by modifying the divergence and curvature of the slots 1134, 1136 of commissure posts 1120 or by modifying the divergence and curvature of the projections 4260 for securing the leaflet construct 104 to the frame 1102.

Although some examples have been provided, it should be understood that similar diverging attachment regions may be implemented with cut tube, wire frame, or any other type of frame (or frame material) as desired to achieve reduced, and more distributed stresses from the leaflet termini. The attachment configurations described above can be particularly advantageous when employed with polymeric (e.g., ePTFE-based) leaflets, although any of a variety of leaflet materials are contemplated.

Transcatheter Delivery System

Figure 44:
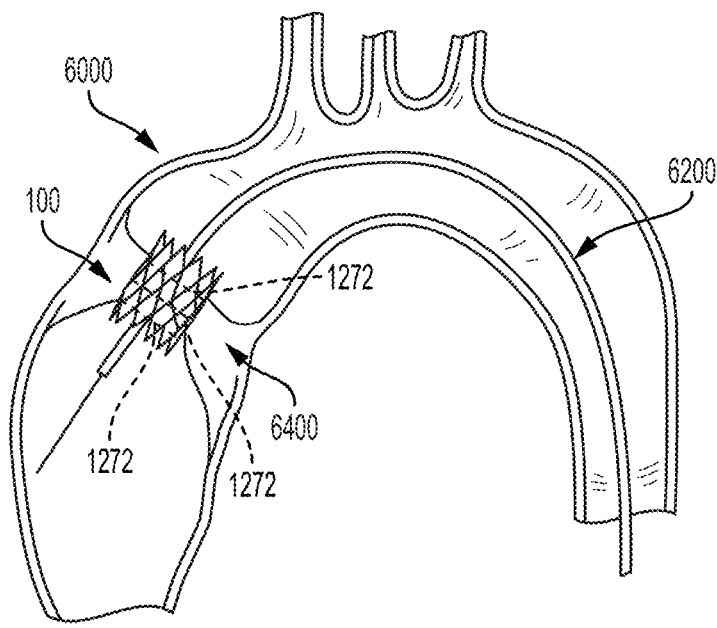
FIGS. 44 and 45 are illustrative of methods of delivering prosthetic valves to treatment locations, according to some embodiments.

In some embodiments, with reference to FIG. 44, a transcatheter delivery system 6000 comprises a prosthetic valve 6100 (according to any of the examples previously described) having a diametrically compacted, or collapsed configuration, and an expanded operational configuration (as shown) and a delivery catheter 6200, configured to deploy the prosthetic valve 6100. The prosthetic valve 6100 can be mounted to an end of the delivery catheter 6200 for delivery through the vasculature and maintained in a collapsed state by a plurality of the constraints 1272 which are then released to permit expansion of the prosthetic valve 6100. In order to hold the prosthetic valve 6100 in a collapsed configuration on the delivery catheter 6200, the transcatheter delivery system 6000 may further comprise a removable sheath (not shown) or other type of constraint to closely fit over the prosthetic valve 100.

Some methods of delivery include the steps of radially compressing the prosthetic valve 100 (according to any of the examples previously described) into its collapsed configuration onto the end of the delivery catheter 6200; delivering the prosthetic valve 100 to a desired treatment location, including a tissue orifice 6400, such as a native valve orifice (e.g., aortic valve orifice or a mitral valve orifice), via a transfemoral or transapical route, and expanding the prosthetic valve 100 into the tissue orifice 6400. The prosthetic valve 100 can be self-expanding and/or expansion can also be facilitated by expanding a balloon (not shown). In some examples, the method includes releasing the constraints 1272, which are passed through one or more of the more rows of apertures 1270, the plurality of constraint retainers 1106, the circumferentially-oriented eyelets 2024A, and/or the radially-oriented eyelets 2024R as previously described.

Surgical Embodiments

Figure 45:
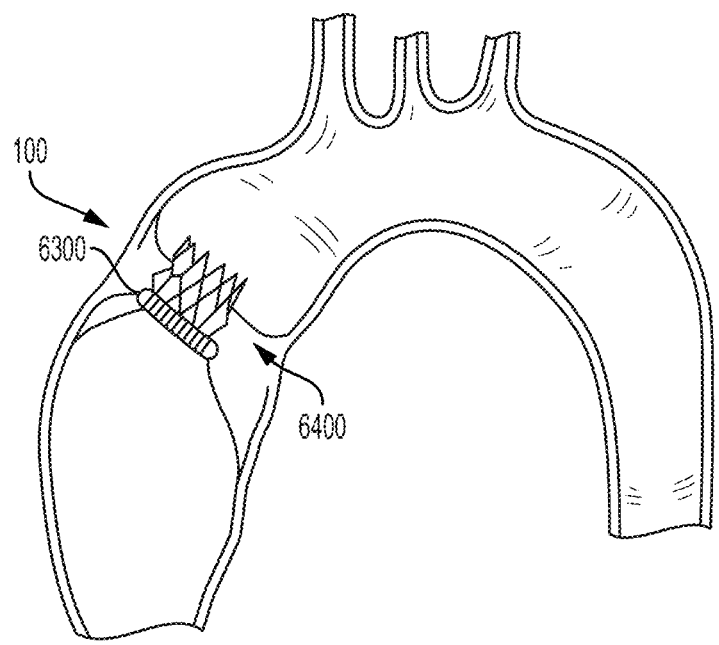

It is appreciated that the prosthetic valve 100 (according to any of the examples previously described) may be surgically implanted rather than using transcatheter techniques. As shown in FIG. 45, the prosthetic valve 100 (according to any of the examples previously described) may have a sewing cuff 6300 adjacent to the frame outer side. The sewing cuff 6300, which may be of a type known in the art, is operable to provide structure that receives suture for coupling the prosthetic valve 100 to an implant site, such as the tissue orifice 6400. The sewing cuff may comprise any suitable material, such as, but not limited to, double velour polyester. The sewing 6300 cuff may be located circumferentially around the frame of the prosthetic valve 100, for example.

Leaflet Materials

In various examples, the leaflet construct 104 is formed of a biocompatible, synthetic material (e.g., including ePTFE and ePTFE composites, or other materials as desired). In other examples, the leaflet construct 104 is formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet further comprises a layer of an elastomer and/or an elastomeric material and/or a non-elastomeric material on the composite material. In accordance with examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkylvinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

Some examples of suitable leaflet materials may be found in U.S. Pat. No. 8,961,599 to Bruchman et al. ("Durable High Strength Polymer Composite Suitable for Implant and Articles Produced Therefrom"); U.S. Pat. No. 8,945,212 to Bruchman et al. ("Durable Multi-Layer High Strength Polymer Composite Suitable for Implant and Articles Produced Therefrom"); U.S. Pat. No. 9,554,900 to Bruchman et al. ("Durable High Strength Polymer Composites Suitable for Implant and Articles Produced Therefrom"); and U.S. Pat. App. Pub. 2015/0224231 to Bruchman et al. ("Coherent Single Layer High Strength Synthetic Polymer Composites for Prosthetic Valves").

Frame Materials

The frames can be etched, cut, laser cut, stamped, three-dimensional printed or wire wound, among other suitable processes. The frames can be self-expanding or balloon expandable (e.g., when configured for transcatheter implantation) or non-expandable (e.g., when configured for surgical implantation). The various frames can comprise materials, such as, but not limited to, any metallic or polymeric material, such as an elastically (e.g., nitinol) or plastically (e.g., stainless steel) deformable metallic or polymeric material that is generally biocompatible. Other materials suitable for any of the frames described herein include, but are not limited to, other titanium alloys, stainless steel, cobalt-nickel alloy, polypropylene, acetyl homopolymer, acetyl copolymer, a drawn filled tube (e.g., nitinol wire with a platinum core), other alloys or polymers, or any other material that is generally biocompatible having adequate physical and mechanical properties to function as a frame as described herein.

Methods of Making

Various methods of making prosthetic valves are contemplated for the various prosthetic valves described herein. Generally, the methods include providing a frame and a leaflet construct according to any of the above-described embodiments and securing the leaflet construct to the frame.

In some methods of making prosthetic valves, the leaflet construct is at least partially coupled to the frame by a looped structure. For example, in some methods the commissure tabs of the leaflet construct define one or more loops that are passed through slots in the commissure posts of the frames, such as the commissure posts according to any of the frame embodiments previously described. In some examples, inner retaining elements pass through one or more of the loops to help widen the loops and help prevent the loop(s), or passes of material, from pulling outwardly through the slots in the commissure posts. Outer retaining elements additionally or alternatively help prevent the loop(s), or passes of material, from pulling inwardly through the slots in the commissure posts. In various examples, the loop(s) of material are optionally coupled to one another and/or to the frame (e.g., bonded or adhered by an outer wrap of film, sutured, or otherwise secured) to help secure the commissure tabs to the commissure posts. In various examples, the body portions of the leaflets are optionally attached to the frame using attachment tabs secured through and folded over the outer side of the frame and/or cover. In some methods, leaflet retention features are coupled onto (e.g., slidingly received onto) leaflet frame projections to secure the leaflets to the frame. These and other methods should be apparent from the foregoing disclosure.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A prosthetic valve configured to be diametrically collapsible into a compact delivery configuration, the prosthetic valve comprising:
    a support structure having an outer side and an inner side and a central longitudinal axis and including a frame including a plurality of frame members and a plurality of commissure posts, the frame extending from a distal end to a proximal end, the distal end having a first diameter and the proximal end having a second larger diameter such that the frame has a diametric taper defining a decrease in diameter in a distal direction between the distal end and the proximal end, the diametric taper including a proximal taper, a distal taper, and an intermediate taper between the distal taper and the proximal taper, the proximal taper defining a proximal taper angle relative to the central longitudinal axis of the frame when the prosthetic valve is in an unloaded state, the intermediate taper defining an intermediate taper angle relative to the central longitudinal axis of the frame when the prosthetic valve is in an unloaded state, and the distal taper defining a distal taper angle relative to the central longitudinal axis of the frame when the prosthetic valve is in an unloaded state, the proximal taper angle being different from the intermediate taper angle and the distal taper angle being different than the intermediate taper angle; and
    a leaflet construct including a plurality of leaflets spaced circumferentially about the leaflet construct, the plurality of leaflets being operatively coupled to the frame;
    wherein the distal taper angle is greater than the intermediate taper angle when the prosthetic valve is in an unloaded state.

2. The prosthetic valve of claim 1, wherein the plurality of commissure posts defines the distal taper of the diametric taper.

3. The prosthetic valve of claim 1, wherein the plurality of frame members extend distally to a frame member distal boundary and the plurality of commissure posts extend distally to a commissure post distal boundary, and further wherein the commissure post distal boundary is located distal to the frame member distal boundary.

4. The prosthetic valve of claim 1, wherein the plurality of frame members extend distally to a frame member distal boundary and the plurality of leaflets extend distal to the frame member distal boundary.

5. The prosthetic valve of claim 1, wherein the plurality of frame members define a plurality of rows of closed cells, including a distal row of closed cells and a proximal row of closed cells located proximal to the distal row of closed cells, wherein each of the closed cells of the distal row of closed cells defines a cell height between a distal end and a proximal end of the closed cell, wherein each of the closed cells of the proximal row of closed cells defines a cell height between a distal end and a proximal end of the closed cell, and further wherein the cell heights of the distal row of closed cells are each less than the cell heights of the proximal row of closed cells.

6. The prosthetic valve of claim 5, wherein the plurality of rows of closed cells defined by the plurality of frame members further includes an intermediate row of closed cells located intermediate the proximal row of closed cells and the distal row of closed cells, wherein each of the closed cells of the intermediate row of closed cells defines a cell height between a distal end and a proximal end of the closed cell, and further wherein the cell heights of the intermediate row of closed cells are less than the cell heights of the proximal row of closed cells and greater than the cell heights of the distal row of closed cells.

7. The prosthetic valve of claim 1, wherein the plurality of frame members define a plurality of rows of closed cells, including a distal row of closed cells and a proximal row of closed cells located proximal to the distal row of closed cells, wherein each of the closed cells of the distal row of closed cells includes at least two proximal-facing apices.

8. The prosthetic valve of claim 1, wherein the plurality of frame members define a plurality of rows of distal-facing apices, wherein each of the distal-facing apices defines an apex angle, and wherein each of the apex angles of each of the distal-facing apices of each of the rows of distal-facing apices has an apex angle that is within 10% of a common apex angle.

9. The prosthetic valve of claim 1, wherein the plurality of frame members define a plurality of rows of proximal-facing apices, wherein each of the proximal-facing apices defines an apex angle, and wherein each of the apex angles of each of the proximal-facing apices of each of the rows of proximal-facing apices has an apex angle that is within 10% of a common apex angle.

10. The prosthetic valve of claim 1, wherein the plurality of frame members defines a column of distal-facing apices and proximal-facing apices, each of the distal-facing apices and the proximal-facing apices defining apex angles within 10% of a common apex angle.

11. The prosthetic valve of claim 1, wherein each of the leaflets of the leaflet construct extends distally from a leaflet base to a free edge, each of the leaflet bases being located at a first longitudinal location along the central longitudinal axis of the support structure, the frame defining a leaflet base level diameter at the first longitudinal location, each of the leaflets being coupled to the plurality of commissure posts at a second longitudinal location along the central longitudinal axis of the support structure that is distal to the first longitudinal location, the frame defining a commissure level diameter at the second longitudinal location, the commissure level diameter being less than the leaflet base level diameter when the prosthetic valve is in an unloaded state and the commissure level diameter being closer in value to the leaflet base diameter when the prosthetic valve is in an operational state than in the unloaded state, the operational state including the prosthetic valve being subjected to an inward radial compressive force on at least a proximal portion of the prosthetic valve.

12. The prosthetic valve of claim 1, wherein the support structure further comprises a cover secured to the frame.

13. The prosthetic valve of claim 1, further comprising a sealing cuff including a sealing member having a portion that is secured circumferentially about the support structure and a distal-facing edge, at least a portion of which is not secured to the support structure.

14. The prosthetic valve of claim 13, wherein the distal-facing edge is secured to the support structure at a plurality of locations and remains unsecured from the support structure at a plurality of locations.

15. The prosthetic valve of claim 1, wherein each of the leaflets of the leaflet construct extends distally from a leaflet base to a free edge, each of the leaflet bases being substantially flat.

16. The prosthetic valve of claim 1, further comprising a plurality of constraint retainers secured to the plurality of frame members.

17. The prosthetic valve of claim 16, further comprising a constraint slidably received by the plurality of constraint retainers.

18. A prosthetic valve configured to be diametrically collapsible into a compact delivery configuration, the prosthetic valve comprising:
- a support structure having an outer side and an inner side and a central longitudinal axis and including a frame including a plurality of frame members and a plurality of commissure posts, the frame extending from a distal end to a proximal end, the distal end having a first diameter and the proximal end having a second larger diameter such that the frame has a diametric taper defining a decrease in diameter in a distal direction between the distal end and the proximal end, the diametric taper including a proximal taper, a distal taper, and an intermediate taper between the distal taper and the proximal taper, the proximal taper defining a proximal taper angle relative to the central longitudinal axis of the frame when the prosthetic valve is in an unloaded state, the intermediate taper defining an intermediate taper angle relative to the central longitudinal axis of the frame when the prosthetic valve is in an unloaded state, and the distal taper defining a distal taper angle relative to the central longitudinal axis of the frame when the prosthetic valve is in an unloaded state, the proximal taper angle being different from the intermediate taper angle and the distal taper angle being different than the intermediate taper angle; and
- a leaflet construct including a plurality of leaflets spaced circumferentially about the leaflet construct, the plurality of leaflets being operatively coupled to the frame;
- wherein the distal taper angle is greater than the proximal taper angle when the prosthetic valve is in an unloaded state.

* * * * *